US010950326B2

(12) United States Patent
Kim et al.

(10) Patent No.: US 10,950,326 B2
(45) Date of Patent: Mar. 16, 2021

(54) METHOD FOR PERSONALIZED SELECTION OF A DRUG FOR A SUBJECT

(71) Applicant: CIPHEROME, INC., Cupertino, CA (US)

(72) Inventors: Ju Han Kim, Seoul (KR); Su Yeon Baik, Pyeongtaek-si (KR); Soo Youn Lee, Gwacheon-si (KR)

(73) Assignee: Cipherome, Inc., Cupertino, CA (US)

( * ) Notice: Subject to any disclaimer, the term of this patent is extended or adjusted under 35 U.S.C. 154(b) by 1119 days.

(21) Appl. No.: 14/912,397

(22) PCT Filed: Aug. 19, 2014

(86) PCT No.: PCT/KR2014/007685
§ 371 (c)(1),
(2) Date: Feb. 16, 2016

(87) PCT Pub. No.: WO2015/026135
PCT Pub. Date: Feb. 26, 2015

(65) Prior Publication Data
US 2016/0210401 A1 Jul. 21, 2016

(30) Foreign Application Priority Data
Aug. 19, 2013 (KR) .................. 10-2013-0097651

(51) Int. Cl.
*G16B 20/00* (2019.01)
*C12Q 1/6883* (2018.01)
*G16C 20/30* (2019.01)
*G16B 40/00* (2019.01)
*G16B 20/20* (2019.01)

(52) U.S. Cl.
CPC .......... *G16B 20/00* (2019.02); *C12Q 1/6883* (2013.01); *G16C 20/30* (2019.02); *C12Q 2600/106* (2013.01); *C12Q 2600/156* (2013.01); *G16B 20/20* (2019.02); *G16B 40/00* (2019.02)

(58) Field of Classification Search
None
See application file for complete search history.

(56) References Cited

U.S. PATENT DOCUMENTS

| 2007/0299646 | A1 | 12/2007 | Chemama et al. |
| 2011/0230360 | A1 | 9/2011 | Dietrich et al. |
| 2012/0016594 | A1 | 1/2012 | Christman et al. |
| 2012/0136583 | A1 | 5/2012 | Lazar et al. |
| 2013/0184999 | A1 | 7/2013 | Ding |

FOREIGN PATENT DOCUMENTS

| CN | 102473202 A | 5/2012 |
| JP | 2009-538631 A | 11/2009 |
| JP | 2012-533103 A | 12/2012 |
| KR | 10-2004-0103514 A | 12/2004 |
| WO | WO 2012/155148 A2 | 11/2012 |
| WO | WO 2012/174723 A1 | 12/2012 |

OTHER PUBLICATIONS

Baek et al. (MedCassandra, Seoul University, Master's degree thesis, Feb. 2013, pp. 1-36) (Year: 2013).*
European Extended Search Report, European Application No. 14838351.6, dated Feb. 24, 2017, 8 pages.
Baik et al., "MedCassandra: Personalized Drug and ADR Ranking Forecast System based on Personal Genome Variations," Graduate School Master's Degree Thesis, Seoul National University, Feb. 2013, pp. 1-29.
European Examination Report, European Application No. 14838351.6, dated Feb. 12, 2018, 4 pages.
PCT International Search Report and Written Opinion, PCT Application No. PCT/KR2016/001632, dated May 12, 2016, 15 pages.
Japanese Office Action, Japanese Application No. 2016-536029, dated Jun. 27, 2017, 9 pages.
PCT International Search Report, PCT/KR2014/007685, dated Nov. 21, 2014, 4 pages.
Baek, Su Yeon, "MedCassandra: Personalized Drug and ADR Ranking Forecast System Based on Personal Genome Variations," The Department of Biomedical Sciences, Seoul National University College of Medicine, Graduate School Master's degree thesis, Feb. 2013.
Kim, I. K., et al., "Clinical Pharmacogenomics of Drug Metabolizing Enzymes and its Clinical Application," 2006, Kor. J. Clin, Pharm., vol. 16, No. 2. (with English Abstract).
Adzhubei, I. et al., "A method and server for predicting damaging missense mutations," Nature Methods, Apr. 1, 2010, pp. 248-249, vol. 7, No. 4.
China National Intellectual Property Administration, Notification of the First Office Action, CN Patent Application No. 201480046187.7, dated Mar. 5, 2019, 76 pages.
European Patent Office, Extended European Search Report and Opinion, European Patent Application 19153339.7, Apr. 4, 2019, 9 pages.

* cited by examiner

*Primary Examiner* — Pablo S Whaley
(74) *Attorney, Agent, or Firm* — Fenwick & West LLP

(57) ABSTRACT

The present invention relates to a method and a system for selecting a drug customized on the basis of individual protein information by using individual genome sequences. The method and the system of the present invention can predict the individual side effects or danger of a certain drug by analyzing the sequence of the exon region of a gene encoding various proteins involved in the pharmacokinetics or pharmacodynamics of a predetermined drug or drug group, and have high reliability and are widely applicable and universal.

13 Claims, 12 Drawing Sheets

METHOD FOR PERSONALIZED SELECTION OF A DRUG FOR A SUBJECT

TECHNICAL FIELD

The present invention relates to a method and a system for personalizing drug selection on the basis of individual deleterious protein sequence variation by using individual genome sequence analysis.

BACKGROUND ART

With the advancement of biotechnology, at present, it is possible to predict a disease of each individual and provide personalized prevention and treatment of disease by analyzing whole genome sequence of human.

Recently, as a result of comparison of individual genome sequences, it was found that different bases may be present at the same position in chromosomes. Accordingly, such a difference in a sequence has been used to predict an individual difference in drug response. For example, drug metabolism may be slow or rapid depending on a specific individual genome sequence information, and, thus, each individual may have different therapeutic effects or side effects of drug.

Accordingly, there has been an increase in a demand for personalizing drug selection which is capable of selecting a drug and a dose suitable for a patient by using a difference of the individual genome sequence. Also, pharmacogenetics or pharmacogenomics, which uses genomic information, for example, single nucleotide polymorphism (SNP), as a marker and correlation between the marker and drug response/drug side effect, has emerged.

Pharmacogenetics is the study of predicting differences in metabolism of drugs or chemicals and response thereto in a general population or between individuals by genetic analysis. Some individuals may show unexpected drug responses. Such drug side effects may be due to severity of a disease under treatment, drug interaction, ages, nutritive conditions, liver and kidney functions of patients, and environmental factors such as weather or nourishment. However, they may be also caused by drug metabolism-related genetic differences, for example, polymorphism of drug metabolizing enzyme gene. Therefore, the study thereof has been conducted.

For example, Korean Patent Laid-open Publication No. 2007-0111475 discloses a technology relating to biomarkers for identifying efficacy of tegaserod in patients with chronic constipation, and uses pharmacogenetics to evaluate the effect of polymorphisms in selecting candidate genes on the response of patients with chronic constipation to tegaserod (Zelmac®/Zelnorm®).

Meanwhile, it is not easy to find a disease predicting marker by using statistics on investigating correlation between an individual genome sequence variation and a disease. This is because most of the single nucleotide polymorphisms showing statistical significance have an insignificant effect on development of disease (odds ratio of 1.1 to 1.5) and are positioned in introns and intergenic regions, and, thus, it is difficult to deduce a functional correlation thereof (Hindorff et al., Proc. Natl. Acad. Sci. 2009; 106(23):9362 to 9367).

Accordingly, beyond a method based on a result of population observational studys using a marker such as single nucleotide polymorphism, a method for providing personalized drug selection information which is more useful and reliable by directly using individual genome sequence variation information and conducting theoretical deduction on protein damage caused thereby and biological effect thereof strongly needs to be introduced.

DISCLOSURE

Technical Problem

The present invention conceived in view of the foregoing is directed to providing a method and a system for providing information for personalizing drug selection by analyzing individual genome sequence variation information, calculating an individual protein damage score from gene sequence variation information involved in the pharmacodynamics or pharmacokinetics of a predetermined drug or drug group, and then associating the score with a drug-protein relation to thereby calculate an individual drug score.

Technical Solution

One aspect of the present invention provides a method for providing information for personalizing drug selection using individual genome sequence variations, including: determining one or more gene sequence variation information involved in the pharmacodynamics or pharmacokinetics of a predetermined drug or drug group on the basis of individual genome sequence information; calculating an individual protein damage score by using the gene sequence variation information; and associating the individual protein damage score with a drug-protein relation to thereby calculate an individual drug score.

In another aspect, the present invention provides a system for personalizing drug selection using individual genome sequence variations, the system including: a database from which information relevant to a gene or protein related to a drug or drug group applicable to an individual can be searched or extracted; a communication unit accessible to the database; a first calculation module configured to calculate one or more gene sequence variation information involved in the pharmacodynamics or pharmacokinetics of the drug or drug group on the basis of the information; a second calculation module configured to calculate an individual protein damage score by using the gene sequence variation information; a third calculation module configured to calculate an individual drug score by associating the individual protein damage score with a drug-protein relation; and a display unit configured to display the values calculated by the calculation modules.

In another aspect, the present invention provides a computer-readable medium including an execution module for executing a processor that performs an operation including: acquiring gene sequence variation information involved in the pharmacodynamics or pharmacokinetics of a predetermined drug or drug group from individual genome sequence information; calculating an individual protein damage score by using the gene sequence variation information; and associating the individual protein damage score with a drug-protein relation to thereby calculate an individual drug score.

Advantageous Effects

A method and a system for personalizing drug selection on the basis of individual genome sequence variation information of the present invention can predict the individual responsiveness to a specific drug by analyzing the sequence of the exon region of a gene encoding various proteins involved in the pharmacodynamics or pharmacokinetics of a predetermined drug or drug group, and have high reliability and are widely applicable to a whole range of drugs and universal. That is, the method and the system of the present invention are universal technologies applicable to a whole range of drugs from which protein information involved in the pharmacodynamics or pharmacokinetics can be acquired with respect to metabolism, effects or side effects of drugs.

Further, conventionally, while a pharmacogenomics study needs to be conducted on each drug-gene pair, it is practically impossible to study all of the numerous drug-gene pairs because the number of pairs increases in proportion to the multiple of the number of drugs and the number of gene markers. Thus, sufficient supporting data have not yet been generated, and selection of study subjects and a difference between population groups lead to a high statistical error. However, according to the method of the present invention, results of study and analysis at a molecular level are directly applied to personalized drug treatment, and, thus, grounds of almost all of drug-gene pairs can be acquired and the method can be applied without being significantly affected by a difference between population groups.

If the method and the system of the present invention are used, it is possible to effectively personalize drug selection among one selected drug, two or more drugs in need of selection, or various comparable drugs belonging to the same drug group which can be used in a specific medical condition, and also possible to predict side effects or risks of drugs. Therefore, the method and the system of the present invention can be used to determine the order of priorities among drugs applicable to an individual or to determine whether or not to use the drugs.

Further, if new information about a drug-protein relation is found or provided, it can be easily added and applied to the method of the present invention. Thus, it is possible to provide an improved personalized drug treatment method according to further accumulation of information as results of studies.

MODES OF THE INVENTION

Figure 1:
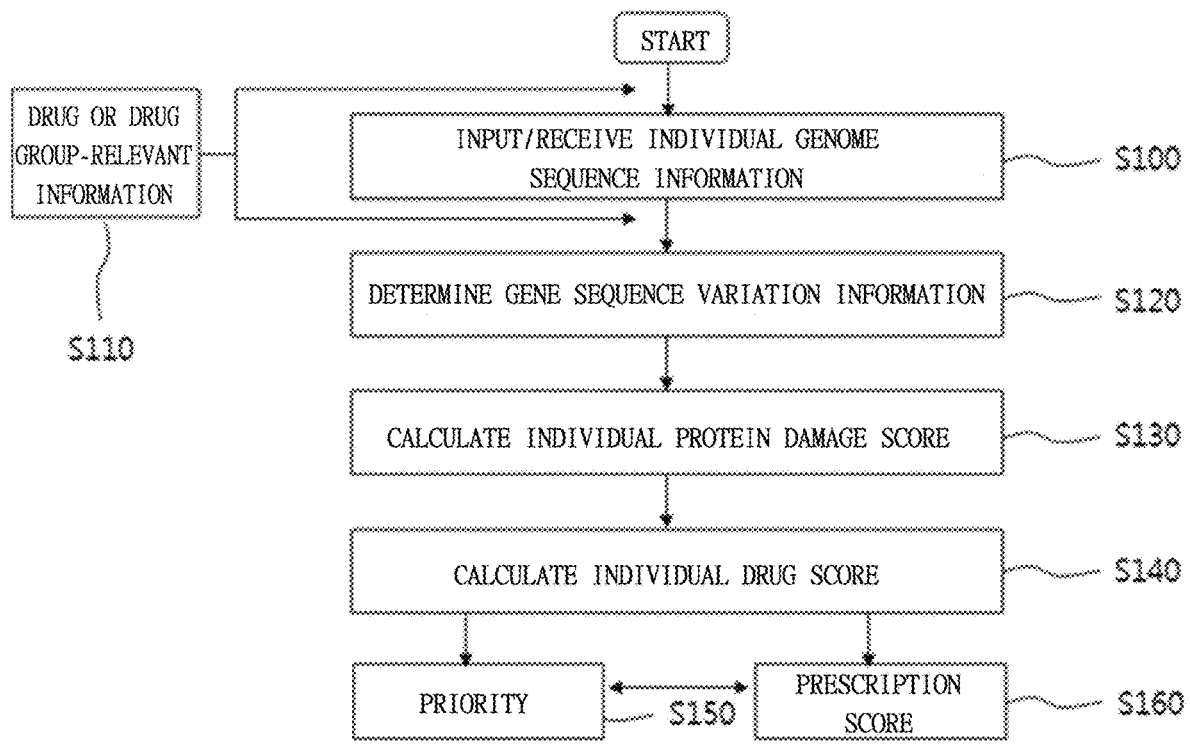
FIG. 1 is a flowchart illustrating each step of a method for providing information for personalizing drug selection using individual genome sequence variations according to an exemplary embodiment of the present invention.

The present invention is based on the finding that it is possible to select a highly safe drug and dose/usage individually in a drug treatment for treating a specific disease by analyzing individual genome sequence variation information.

One aspect of the present invention provides a method for providing information for personalizing drug selection using individual genome sequence variations, including: determining one or more gene sequence variation information involved in the pharmacodynamics or pharmacokinetics of a predetermined drug or drug group on the basis of individual genome sequence information; calculating an individual protein damage score by using the gene sequence variation information; and associating the individual protein damage score with a drug-protein relation to thereby calculate an individual drug score.

The gene sequence variation used as information in the method of the present invention refers to an individual gene sequence variation or polymorphism. In the present invention, the gene sequence variation or polymorphism occurs particularly in an exon region of a gene encoding proteins involved in the pharmacodynamics or pharmacokinetics of a predetermined drug or drug group, but is not limited thereto.

The term "sequence variation information" used herein means information about substitution, addition, or deletion of a base constituting an exon of a gene. Such substitution, addition, or deletion of the base may result from various causes, for example, structural differences including mutation, breakage, deletion, duplication, inversion, and/or translocation of a chromosome.

In another aspect, a polymorphism of a sequence refers to individual differences in a sequence present in a genome. In the polymorphism of a sequence, single nucleotide polymorphisms (SNPs) are in the majority. The single nucleotide polymorphism refers to individual differences in one base of a sequence consisting of A, T, C, and G bases. The sequence polymorphism including the SNP can be expressed as a SNV (Single Nucleotide Variation), STRP (short tandem repeat polymorphism), or a polyalleic variation including VNTR (various number of tandem repeat) and CNV (Copy number variation).

In the method of the present invention, sequence variation or polymorphism information found in an individual genome is collected in association with a protein involved in the pharmacodynamics or pharmacokinetics of a predetermined drug or drug group. That is, the sequence variation information used in the present invention is variation information found particularly in an exon region of one or more genes involved in the pharmacodynamics or pharmacokinetics of a drug or drug group effective in treating a specific disease, for example, genes encoding a target protein relevant to a drug, an enzyme protein involved in drug metabolism, a transporter protein, and a carrier protein, among the obtained individual genome sequence information, but is not limited thereto.

The term "pharmacokinetics (pk) or pharmacokinetic parameters" used herein refers to characteristics of a drug involved in absorption, migration, distribution, conversion, and excretion of the drug in the body for a predetermined time period, and includes a volume of distribution (Vd), a clearance rate (CL), bioavailability (F) and absorption rate coefficient (ka) of a drug, or a maximum plasma concentration (Cmax), a time point of maximum plasma concentration (Tmax), an area under the curve (AUC) regarding a change in plasma concentration for a certain time period, and so on.

The term "pharmacodynamics or pharmacodynamic parameters" used herein refers to characteristics involved in physiological and biochemical behaviors of a drug with respect to the body and mechanisms thereof, i.e., responses or effects in the body caused by the drug.

A list of genes involved in the pharmacodynamics or pharmacokinetics of a predetermined drug or drug group is provided in the following Table 1 to Table 15. To be more specific, among 920 drugs extracted by mapping top 15 frequently prescribed drug classes during 2005 to 2008 in the United States provided in a report (Health, United States, 2011, Centers for Disease Control and Prevention (CDC)) issued from the CDC with ATC codes as the standard drug classification codes, 395 drugs, of which at least one gene involved in the pharmacodynamics or pharmacokinetics is known, provided from DrugBank ver 3.0 and KEGG Drug database and pairs of the drugs and genes are listed in the following Table 1 to Table 15. In the following Table 1 to Table 15, genes/proteins are expressed according to the HGNC (HUGO Gene Nomenclature Committee) nomenclature (Gray K A, Daugherty L C, Gordon S M, Seal R L, Wright M W, Bruford E A. genenames.org: the HGNC resources in 2013. Nucleic Acids Res. 2013 January; 41 (Database issue): D545-52. doi: 10.1093/nar/gks1066. Epub 2012 Nov. 17 PMID:23161694).

Further, gene/protein information involved in the pharmacodynamics or pharmacokinetics of a predetermined drug or drug group can be acquired from the database such as DrugBank (http://www.drugbank.ca/), KEGG Drug http://www.genome.jp/kegg/drug/), or PharmGKB (https://www.pharmgkb.org/). The following Table 1 to Table 15 are just examples, but the present invention is not limited thereto.

TABLE 1

ACE inhibitors [C09A]

| Drugs | Target protein | Enzyme protein | Carrier protein | Transporter protein |
|---|---|---|---|---|
| Benazepril | ACE | MTHFR | SLC15A1, SLC15A2 | |
| Captopril | ACE, MMP2 | CYP2D6 | ABCB1, SLC15A1, SLC15A2, SLC22A6 | ALB |
| Cilazapril | ACE | | ABCB1, SLC15A1, SLC15A2 | |
| Enalapril | ACE | CYP3A4 | ABCB1, SLC15A1, SLC15A2, SLC22A6, SLC22A7, SLC22A8, SLCO1A2 | |
| Fosinopril | ACE | | SLC15A1, SLC15A2 | |
| Lisinopril | ACE, ACE2 | | ABCB1, SLC15A1 | |
| Moexipril | ACE, ACE2 | | SLC15A1, SLC15A2 | |
| Perindopril | ACE | | ABCB1, SLC15A1, SLC15A2 | |
| Quinapril | ACE | | SLC15A1, SLC15A2 | |
| Ramipril | ACE | | SLC15A1, SLC15A2 | |
| Spirapril | ACE | | SLC15A1, SLC15A2 | |
| Trandolapril | ACE | | SLC15A1, SLC15A2 | |
| Bupropion | CHRNA3, SLC6A2, SLC6A3 | CYP1A2, CYP2A6, CYP2B6, CYP2C8, CYP2C9, CYP2D6, CYP2E1, CYP3A4 | | ORM1 |

TABLE 2

Analgesics [N02]

| Drugs | Target protein | Enzyme protein | Carrier protein | Transporter protein |
|---|---|---|---|---|
| Acetaminophen | PTGS1, PTGS2 | CYP1A1, CYP1A2, CYP2A6, CYP2C8, CYP2C9, CYP2D6, CYP2E1, CYP3A4 | ABCB1, SLC22A6 | |

TABLE 2-continued

Analgesics [N02]

| Drugs | Target protein | Enzyme protein | Carrier protein | Transporter protein |
|---|---|---|---|---|
| Acetylsalicylic acid | AKR1C1, PTGS1, PTGS2 | CYP2C19, CYP2C8, CYP2C9 | ABCB1, SLC16A1, SLC22A10, SLC22A11, SLC22A6, SLC22A7, SLC22A8, SLCO2B1 | ALB |
| Almotriptan | HTR1B, HTR1D | CYP1A2, CYP2C19, CYP2C8, CYP2D6, CYP2E1, CYP3A4, FMO3, MAOA | | |
| Aminophenazone | | CYP17A1, CYP1A2, CYP2C18, CYP2C19, CYP2C8, CYP2C9, CYP2D6, CYP3A4, CYP3A7 | SLC22A6 | |
| Antipyrine | PTGS1, PTGS2 | CYP1A2, CYP2A6, CYP2B6, CYP2C18, CYP2C19, CYP2C8, CYP2C9, CYP2D6, CYP2E1, CYP3A4 | SLC22A6 | |
| Buprenorphine | OPRD1, OPRK1, OPRM1 | CYP1A2, CYP2A6, CYP2C18, CYP2C19, CYP2C8, CYP2C9, CYP2D6, CYP3A4, CYP3A5, CYP3A7, UGT1A9 | ABCB1, ABCG2 | |
| Butorphanol | OPRD1, OPRK1, OPRM1 | | | |
| Dezocine | OPRK1, OPRM1 | | | |
| Diflunisal | PTGS1, PTGS2 | | SLC22A6 | ALB, TTR |
| Dihydroergotamine | ADRA1A, ADRA1B, ADRA1D, ADRA2A, DRD1, DRD2, GABRA1, HTR1A, HTR1B, HTR1D, HTR2A, HTR2B | CYP3A4 | ABCB1 | |
| Dipyrone | PTGS1 | CYP2B6, CYP3A4 | | |
| Eletriptan | HTR1A, HTR1B, HTR1D, HTR1E, HTR1F, HTR2B, HTR7 | CYP2A6, CYP2C19, CYP2C9, CYP2D6, CYP3A4, PTGS1 | ABCB1 | |
| Ergotamine | ADRA1A, ADRA1B, ADRA1D, ADRA2A, ADRA2B, DRD2, HTR1A, HTR1B, HTR1D, HTR2A, SLC6A2 | CYP1A2, CYP3A4 | ABCB1 | |
| Fentanyl | OPRD1, OPRK1, OPRM1 | CYP3A4, CYP3A5, CYP3A7 | ABCB1 | |
| Frovatriptan | HTR1B, HTR1D | CYP1A2 | | |
| Heroin | OPRD1, OPRK1, OPRM1 | CYP2C8, CYP2D6, CYP3A4, UGT1A1, UGT1A3, UGT1A8, UGT2B4, UGT2B7 | ABCB1 | |
| Hydromorphone | OPRD1, OPRK1, OPRM1 | CYP2C9, CYP2D6, CYP3A4, PTGS1, UGT1A9 | | |
| Lisuride | ADRA2A, ADRA2B, ADRA2C, DRD1, DRD2, DRD3, DRD4, DRD5, HTR1A, HTR1B, HTR1D, HTR2A, HTR2B, HTR2C | CYP2D6, CYP3A4 | | |

TABLE 2-continued

| | Analgesics [N02] | | | |
|---|---|---|---|---|
| Drugs | Target protein | Enzyme protein | Carrier protein | Transporter protein |
| Meperidine | GRIN1, GRIN2A, GRIN2B, GRIN2C, GRIN2D, OPRK1, OPRM1 | CYP2B6, CYP2C19, CYP2D6, CYP3A4 | | ALB, ORM1 |
| Methoxyflurane | ATP2C1, ATP5D, GABRA1, GLRA1, GRIA1, KCNA1 | CYP1A2, CYP2A6, CYP2B6, CYP2C9, CYP2D6, CYP2E1, CYP3A4 | | |
| Methysergide | HTR1A, HTR1B, HTR1D, HTR2A, HTR2B, HTR2C, HTR7 | | | |
| Nalbuphine | OPRD1, OPRK1, OPRM1 | | | |
| Naratriptan | HTR1A, HTR1B, HTR1D, HTR1F | | | |
| Oxycodone | OPRD1, OPRK1, OPRM1 | CYP2D6, CYP3A4, CYP3A5, CYP3A7 | | |
| Pentazocine | OPRK1, OPRM1, SIGMAR1 | | | |
| Phenacetin | PTGS1 | CYP1A1, CYP1A2, CYP2A13, CYP2A6, CYP2C19, CYP2C9, CYP2D6, CYP2E1, CYP3A4 | SLC22A6 | |
| Propoxyphene | OPRD1, OPRK1, OPRM1 | CYP2C8, CYP2C9, CYP2D6, CYP3A4, CYP3A7 | | |
| Rizatriptan | HTR1B, HTR1D, HTR1F | CYP1A2, MAOA | | |
| Salicylamide | PTGS1, PTGS2 | | | |
| Salsalate | PTGS1, PTGS2 | | | |
| Sumatriptan | HTR1A, HTR1B, HTR1D, HTR1F | MAOA | ABCB1, ABCG2, SLCO1A2, SLCO1B1 | |
| Tramadol | CHRFAM7A, CHRM3, GRIN3A, HTR2C, OPRD1, OPRK1, OPRM1, SLC6A2, SLC6A4 | CYP2B6, CYP2D6, CYP3A4 | | |
| Ziconotide | CACNA1B | | | |
| Zolmitriptan | HTR1A, HTR1B, HTR1D, HTR1F | CYP1A2, MAOA | | |
| Clonidine | ADRA2A, ADRA2B, ADRA2C | CYP1A1, CYP1A2, CYP2D6, CYP3A4, CYP3A5 | ABCB1, SLC22A1, SLC22A3, SLC22A4, SLC22A5 | |

TABLE 3

| | Anti-diabetes [A10] | | | |
|---|---|---|---|---|
| Drugs | Target protein | Enzyme protein | Carrier protein | Transporter protein |
| Acarbose | AMY2A, AMY2B, GAA, GANC, MGAM, SI | | | |
| Acetohexamide | ABCC8, ABCC9, KCNJ1 | CBR1 | | |
| Buformin | PRKAA1, PRKAA2 | | | SLC22A1 |

TABLE 3-continued

Anti-diabetes [A10]

| Drugs | Target protein | Enzyme protein | Carrier protein | Transporter protein |
|---|---|---|---|---|
| Chlorpropamide | ABCC8, ABCC9 | CYP2C19, CYP2C9, PTGS1 | ABCB1, SLC15A1, SLC15A2, SLC22A6 | |
| Exenatide | GLP1R | | | |
| Gliclazide | ABCC8, ABCC9, VEGFA | CYP2C19, CYP2C9 | | ALB |
| Glimepiride | ABCC8, ABCC9, KCNJ1, KCNJ11 | CYP2C9 | | |
| Glipizide | ABCC8, ABCC9, PPARG | CYP2C9, CYP3A4 | | |
| Gliquidone | ABCC8, ABCC9, KCNJ8 | | | |
| Glisoxepide | ABCC8, ABCC9, KCNJ8 | | | |
| Glyburide | ABCA1, ABCB11, ABCC8, ABCC9, CFTR, KCNJ1, KCNJ11, KCNJ5 | CYP2C19, CYP2C9, CYP3A4 | ABCB1, ABCB11, ABCC1, ABCC2, ABCC3, ABCG2, SLC15A1, SLC15A2, SLC22A6, SLC22A7, SLCO1A2, SLCO2B1 | ALB |
| Glycodiazine | ABCC8, ABCC9, KCNJ1 | | | |
| Insulin Aspart | INSR | CYP1A2 | | |
| Insulin Detemir | INSR | CYP1A2 | | ALB |
| Insulin Glargine | IGF1R, INSR | CYP1A2 | | |
| Insulin Glulisine | INSR | CYP1A2 | | |
| Insulin Lispro | IGF1R, INSR | CYP1A2 | | |
| Insulin aspart (genetical recombination) | INSR | | | |
| Insulin detemir (genetical recombination) | INSR | | | |
| Insulin glargine (genetical recombination) | INSR | | | |
| Insulin lispro (genetical recombination) | INSR | | | |
| Liraglutide | GLP1R | | | |
| Liraglutide (genetical recombination) | GLP1R | | | |
| Metformin | PRKAA1, PRKAA2, PRKAB1 | | SLC22A1, SLC22A2, SLC47A1, SLC47A2 | |
| Miglitol | GAA, GANC, MGAM | AMY2A | | |
| Mitiglinide | ABCC8, ABCC9, PPARG | UGT1A3, UGT1A9, UGT2B7 | | |
| Nateglinide | ABCC8, ABCC9, PPARG | CYP2C9, CYP2D6, CYP3A4, CYP3A5, CYP3A7, PTGS1, UGT1A9 | ABCC4, SLC15A1, SLC15A2, SLC16A1, SLC22A6 | ALB, ORM1 |
| Phenformin | KCNJ8, PRKAA1 | CYP2D6 | SLC22A1, SLC22A2 | |

TABLE 3-continued

Anti-diabetes [A10]

| Drugs | Target protein | Enzyme protein | Carrier protein | Transporter protein |
|---|---|---|---|---|
| Pioglitazone | PPARG | CYP2C19, CYP2C8, CYP2C9, CYP2D6, CYP3A4, PTGS1 | SLCO1B1, SLCO1B3 | |
| Pramlintide | CALCR, RAMP1, RAMP2, RAMP3 | | | |
| Repaglinide | ABCC8, ABCC9, PPARG | CYP2C8, CYP3A4 | SLCO1B1 | ALB |
| Rosiglitazone | ACSL4, PPARG | CYP1A2, CYP2A6, CYP2C19, CYP2C8, CYP2C9, CYP2D6, PTGS1 | SLCO1B1 | |
| Saxagliptin | DPP4 | CYP3A4, CYP3A5 | | |
| Sitagliptin | DPP4 | CYP2C8, CYP3A4 | ABCB1 | |
| Tolazamide | ABCC8, ABCC9, KCNJ1 | | | |
| Tolbutamide | ABCC8, KCNJ1 | CYP2C18, CYP2C19, CYP2C8, CYP2C9 | SLC15A1, SLC15A2, SLC22A6, SLCO1A2, SLCO2B1 | |
| Troglitazone | ACSL4, CYP2C8, ESRRA, ESRRG, PPARG, SERPINE1, SLC29A1 | CYP19A1, CYP1A1, CYP2B6, CYP2C19, CYP2C8, CYP2C9, CYP3A4, CYP3A5, CYP3A7, UGT1A1, UGT1A10, UGT1A3, UGT1A4, UGT1A8, UGT1A9, UGT2B7 | ABCB11, SLCO1B1 | FABP4 |
| Vildagliptin | DPP4 | | | |
| Voglibose | GAA, GANC, MGAM | | | |

TABLE 4

Antidepressants [N06A]

| Drugs | Target protein | Enzyme protein | Carrier protein | Transporter protein |
|---|---|---|---|---|
| Amineptine | SLC6A2, SLC6A4 | | | |
| Amitriptyline | ADRA1A, ADRA1D, ADRA2A, CHRM1, CHRM2, CHRM3, CHRM4, CHRM5, HRH1, HTR1A, HTR2A, KCNA1, KCND2, KCND3, KCNQ2, NTRK1, NTRK2, OPRD1, OPRK1, SLC6A2, SLC6A4 | CYP1A2, CYP2B6, CYP2C19, CYP2C8, CYP2C9, CYP2D6, CYP2E1, CYP3A4, CYP3A5 | ABCB1 | ALB, ORM1 |
| Amoxapine | ADRA1A, ADRA2A, CHRM1, DRD1, DRD2, | CYP2D6 | | ORM1 |

TABLE 4-continued

| Antidepressants [N06A] | | | | |
|---|---|---|---|---|
| Drugs | Target protein | Enzyme protein | Carrier protein | Transporter protein |
| Citalopram | GABRA1, SLC6A2, SLC6A4 ADRA1A, CHRM1, HRH1, SLC6A2, SLC6A3, SLC6A4 | CYP1A2, CYP2B6, CYP2C19, CYP2D6, CYP2E1, CYP3A4 | ABCB1 | |
| Clomipramine | GSTP1, HTR2A, HTR2B, HTR2C, SLC6A2, SLC6A4 | CYP1A2, CYP2C19, CYP2D6, CYP3A4 | ABCB1 | |
| Desipramine | ADRA1A, ADRB1, ADRB2, CHRM1, CHRM2, CHRM3, CHRM4, CHRM5, HRH1, HTR2A, SLC6A2, SLC6A4, SMPD1 | CYP1A2, CYP2A6, CYP2B6, CYP2C18, CYP2C19, CYP2D6, CYP2E1, CYP3A4 | ABCB1, SLC22A1, SLC22A2, SLC22A3, SLC22A4, SLC22A5 | ORM1 |
| Desvenlafaxine | SLC6A2, SLC6A4 | CYP3A4 | | |
| Doxepin | ADRA1A, ADRA1B, ADRA1D, ADRA2A, ADRA2B, ADRA2C, CHRM1, CHRM2, CHRM3, CHRM4, CHRM5, DRD2, HRH1, HRH2, HTR1A, HTR2A, HTR2B, HTR2C, SLC6A2, SLC6A4 | CYP1A2, CYP2C19, CYP2C9, CYP2D6 | ABCB1 | ORM1 |
| Duloxetine | SLC6A2, SLC6A3, SLC6A4 | CYP1A2, CYP2D6 | | |
| Fluoxetine | HTR2A, SLC6A4 | CYP1A2, CYP2B6, CYP2C19, CYP2C9, CYP2D6, CYP2E1, CYP3A4 | ABCB1 | |
| Fluvoxamine | SLC6A4 | CYP1A1, CYP1A2, CYP2B6, CYP2C19, CYP2C9, CYP2D6, CYP2E1, CYP3A4, CYP3A5, CYP3A7 | ABCB1 | |
| Imipramine | ADRA1A, ADRA1D, CHRM1, CHRM2, CHRM3, CHRM4, CHRM5, HRH1, HTR2A, KCND2, KCND3, SLC6A2, SLC6A4 | CYP1A2, CYP2B6, CYP2C18, CYP2C19, CYP2D6, CYP2E1, CYP3A4, CYP3A7 | ABCB1, SLC22A1, SLC22A2, SLC22A3, SLC22A4 | ORM1 |
| Iproniazid | MAOA, MAOB | MAOB | | |
| Isocarboxazid | MAOA, MAOB | | | |
| L-Citrulline | ASS1, DDAH1, DDAH2, NOS1, NOS2, NOS3, OTC, PADI1, | | | |

TABLE 4-continued

Antidepressants [N06A]

| Drugs | Target protein | Enzyme protein | Carrier protein | Transporter protein |
|---|---|---|---|---|
| L-Tryptophan | PADI2, PADI3, PADI4, PADI6 WARS, WARS2 | DDC, IDO1, TDO2, TPH1, TPH2, WARS, WARS2 | SLC16A10, SLC16A2 | |
| Maprotiline | ADRA1A, CHRM1, CHRM2, CHRM3, CHRM4, CHRM5, HRH1, SLC6A2 | CYP1A2, CYP2D6 | ABCB1 | ORM1 |
| Mianserin | ADRA1A, ADRA1B, ADRA1D, ADRA2A, ADRA2B, ADRA2C, HRH1, HTR1A, HTR1B, HTR1D, HTR1E, HTR1F, HTR2A, HTR2B, HTR2C, SLC6A2, SLC6A4 | CYP1A2, CYP2B6, CYP2C19, CYP2D6, CYP3A4 | | |
| Milnacipran | SLC6A2, SLC6A4 | | | |
| Minaprine | ACHE, CHRM1, DRD1, DRD2, HTR2A, HTR2B, HTR2C, MAOA, SLC6A4 | CYP2D6 | | |
| Mirtazapine | ADRA2A, ADRA2B, ADRA2C, HRH1, HTR2A, HTR2B, HTR2C, HTR3A, HTR3B, HTR3C, HTR3D, HTR3E, OPRK1 | CYP1A2, CYP2C8, CYP2C9, CYP2D6, CYP3A4 | | |
| Moclobemide | MAOA | CYP1A2, CYP2C19, CYP2C9, CYP2D6, MAOA, MAOB | | |
| Nefazodone | ADRA1A, ADRA1B, ADRA2A, HTR1A, HTR2A, HTR2C, SLC6A2, SLC6A3, SLC6A4 | CYP2B6, CYP2D6, CYP3A4, CYP3A5, CYP3A7 | ABCB1 | |
| Nialamide | MAOA, MAOB | | | |
| Nomifensine | SLC6A2, SLC6A3 | | | ORM1 |
| Nortriptyline | ADRA1A, ADRA1D, CHRM1, CHRM2, CHRM3, CHRM4, CHRM5, HRH1, HTR1A, HTR2A, SLC6A2, SLC6A4 | CYP1A2, CYP2C19, CYP2C9, CYP2D6, CYP2E1, CYP3A4, CYP3A5, PTGS1 | | ALB, ORM1 |
| Paroxetine | CHRM1, CHRM2, CHRM3, | CYP2B6, CYP2C8, CYP2C9, CYP2D6 | ABCB1 | |

TABLE 4-continued

Antidepressants [N06A]

| Drugs | Target protein | Enzyme protein | Carrier protein | Transporter protein |
|---|---|---|---|---|
| | CHRM4, CHRM5, HTR2A, SLC6A2, SLC6A4 | | | |
| Phenelzine | ABAT, AOC3, GAD2, GPT, GPT2, MAOA, MAOB | CYP2C19, CYP2C8, CYP2E1, CYP3A4, CYP3A43, CYP3A5, CYP3A7, MAOA, MAOB | | |
| Protriptyline | SLC6A2, SLC6A4 | CYP2D6 | ABCB1 | |
| Reboxetine | SLC6A2 | CYP2D6, CYP3A4 | ABCB1 | |
| Sertraline | SLC6A3, SLC6A4 | CYP1A2, CYP2B6, CYP2C19, CYP2C9, CYP2D6, CYP3A4, MAOA, MAOB | ABCB1 | |
| Tranylcypromine | MAOA, MAOB | CYP1A2, CYP2A6, CYP2C19, CYP2C9, CYP2D6, CYP2E1, CYP3A4 | | |
| Trazodone | ADRA1A, ADRA2A, HRH1, HTR1A, HTR2A, HTR2C, SLC6A4 | CYP2D6, CYP3A4, CYP3A5, CYP3A7 | ABCB1 | ORM1 |
| Trimipramine | ADRA1A, ADRA1B, ADRA2B, DRD1, DRD2, HRH1, HTR1A, HTR2A, SLC6A2, SLC6A3, SLC6A4 | CYP2C19, CYP2C9, CYP2D6, CYP3A4 | ABCB1 | |
| Venlafaxine | SLC6A2, SLC6A3, SLC6A4 | CYP2B6, CYP2C19, CYP2C9, CYP2D6, CYP3A4 | ABCB1 | |
| Vilazodone | HTR1A, SLC6A4 | CYP2C18, CYP2D6, CYP3A4 | | |
| Zimelidine | SLC6A4 | | ABCB1 | |

TABLE 5

Antihistamines for systemic use [R06]

| Drugs | Target protein | Enzyme protein | Carrier protein | Transporter protein |
|---|---|---|---|---|
| Antazoline | HRH1 | | | |
| Astemizole | HRH1, KCNH2 | CYP2D6, CYP2J2, CYP3A4, CYP3A5, CYP3A7 | ABCB1 | |
| Azatadine | HRH1 | CYP3A4 | | |
| Azelastine | HRH1 | CYP1A1, CYP1A2, CYP2A6, CYP2B6, CYP2C19, CYP2C8, CYP2C9, CYP2D6, CYP2E1, CYP3A4, CYP3A5 | ABCB1 | |
| Bromodiphenhydramine | HRH1 | | SLC22A6, SLC47A1 | |
| Brompheniramine | CHRM1, CHRM2, CHRM3, CHRM4, CHRM5, HRH1 | CYP2B6, CYP2C19, CYP2C8, CYP2C9, CYP2D6, CYP2E1, CYP3A4 | | |
| Buclizine | CHRM1, HRH1 | | | |

TABLE 5-continued

Antihistamines for systemic use [R06]

| Drugs | Target protein | Enzyme protein | Carrier protein | Transporter protein |
|---|---|---|---|---|
| Carbinoxamine | HRH1 | CYP2B6, CYP2C19, CYP2C8, CYP2C9, CYP2D6, CYP2E1, CYP3A4 | | |
| Cetirizine | HRH1 | | | |
| Chloropyramine | HRH1 | | | |
| Chlorpheniramine | HRH1, SLC6A2, SLC6A3, SLC6A4 | CYP2D6, CYP3A4, CYP3A5, CYP3A7 | SLC22A1, SLC22A2 | |
| Clemastine | HRH1 | CYP2D6, CYP3A4 | | |
| Cyclizine | HRH1, SULT1E1 | CYP2C9 | | |
| Cyproheptadine | CHRM1, CHRM2, CHRM3, HRH1, HTR2A, HTR2C | | | |
| Desloratadine | HRH1 | CYP1A2, CYP2C19, CYP2C9, CYP2D6 | ABCB1 | |
| Dimethindene | CHRM2, HRH1 | | | |
| Diphenhydramine | HRH1, SLC6A3 | CYP1A2, CYP2B6, CYP2C18, CYP2C19, CYP2C9, CYP2D6, PTGS1 | SLC22A1, SLC22A2, SLC22A5 | |
| Doxylamine | CHRM1, HRH1 | | | |
| Epinastine | ADRA1A, ADRA2A, HRH1, HRH2, HTR2A, HTR7 | CYP2B6, CYP2D6, CYP3A4 | ABCB1 | |
| Fexofenadine | HRH1 | CYP2D6 | ABCB1, ABCC3, SLCO1A2, SLCO1B3, SLCO2B1 | |
| Isothipendyl | HRH1 | | | |
| Ketotifen | HRH1, PDE4A, PDE4B, PDE4C, PDE4D, PDE7A, PDE7B, PDE8A, PDE8B, PGD | | | |
| Loratadine | HRH1 | CYP2C19, CYP2C8, CYP2C9, CYP2D6, CYP3A4 | ABCB1 | |
| Meclizine | HRH1 | CYP1A2 | | |
| Mepyramine | HRH1 | CYP2D6 | | |
| Mequitazine | HRH1 | CYP2D6, CYP3A4 | | |
| Methdilazine | HRH1 | | | |
| Phenindamine | HRH1 | | | |
| Pheniramine | HRH1 | | | |
| Promethazine | ADRA1A, CALM1, CHRM1, CHRM2, CHRM3, CHRM4, CHRM5, DRD2, HRH1, HTR2A | CYP2B6, CYP2C9, CYP2D6 | ABCB1 | |
| Terfenadine | CHRM3, HRH1, KCNH2 | CYP2C8, CYP2C9, CYP2D6, CYP2J2, CYP3A4, CYP3A5, CYP3A7 | ABCB1 | |
| Thiethylperazine | DRD1, DRD2, DRD4 | | | |

TABLE 5-continued

| Antihistamines for systemic use [R06] | | | | |
|---|---|---|---|---|
| Drugs | Target protein | Enzyme protein | Carrier protein | Transporter protein |
| Trimeprazine | HRH1 | CYP3A4 | | |
| Tripelennamine | HRH1 | CYP2D6 | | |
| Triprolidine | HRH1 | CYP2D6 | | |

TABLE 6

| Antihypertensives [C02] | | | | |
|---|---|---|---|---|
| Drugs | Target protein | Enzyme protein | Carrier protein | Transporter protein |
| Ambrisentan | EDNRA | | | |
| Bethanidine | ADRA2A, ADRA2B, ADRA2C, KCNJ1 | | | |
| Bosentan | EDNRA, EDNRB | CYP2C19, CYP2C9, CYP3A4 | ABCB11 | |
| Debrisoquin | SLC6A2 | CYP1A1, CYP2D6 | ABCB1 | |
| Deserpidine | SLC18A2 | | | |
| Diazoxide | ABCC8, ATP1A1, CA1, CA2, KCNJ11, KCNMA1, SLC12A3 | | | |
| Doxazosin | ADRA1A, ADRA1B, ADRA1D, KCNH2, KCNH6, KCNH7 | CYP2C19, CYP2D6 | ABCB1 | ORM1 |
| Guanethidine | SLC6A2 | CYP3A4 | | |
| Guanfacine | ADRA2A, ADRA2B, ADRA2C | CYP2C19, CYP2C9, CYP3A4 | | |
| Hydralazine | AOC3, P4HA1 | CYP3A4 | | |
| Mecamylamine | CHRNA1, CHRNA10, CHRNA2, CHRNA3, CHRNA4, CHRNA5, CHRNA6, CHRNA7, CHRNA9, CHRNB1, CHRNB2, CHRNB3, CHRNB4, CHRND, CHRNE, CHRNG | | | |
| Methyldopa | ADRA2A, ADRA2B, ADRA2C, DDC | COMT | SLC15A1 | |
| Metyrosine | TH | | | |
| Minoxidil | ABCC8, KCNJ1, PTGS1 | | | |
| Nitroprusside | NPR1 | CYP1A1, CYP1A2 | | |
| Pargyline | MAOA, MAOB | | | |
| Prazosin | ADRA1A, ADRA1B, ADRA1D, KCNH2, KCNH6, KCNH7 | CYP1A1 | ABCB1, ABCG2, SLC22A1, SLC22A2, SLC22A3 | ORM1 |
| Rescinnamine | ACE | | | |
| Reserpine | SLC18A1, SLC18A2 | CYP3A5 | ABCB1, ABCB11, ABCC2, SLC22A1, SLC22A2 | |

TABLE 6-continued

| Antihypertensives [C02] | | | | |
|---|---|---|---|---|
| Drugs | Target protein | Enzyme protein | Carrier protein | Transporter protein |
| Sitaxentan | EDNRA, EDNRB | CYP2C19, CYP2C9, CYP3A4 | | |
| Trimethaphan | CHRNA10 | BCHE | | |

TABLE 7

| Anxiolytics and Hypnotics/sedatives [N05B|N05C] | | | | |
|---|---|---|---|---|
| Drugs | Target protein | Enzyme protein | Carrier protein | Transporter protein |
| Adinazolam | GABRA1, GABRA2, GABRA3, GABRA5, GABRB1, GABRB2, GABRB3, GABRD, GABRE, GABRG1, GABRG2, GABRG3, GABRP, GABRR1, GABRR2, GABRR3 | CYP2C19, CYP3A4 | | |
| Alprazolam | GABRA1, GABRA2, GABRA3, GABRA4, GABRA5, GABRA6, GABRB1, GABRB2, GABRB3, GABRD, GABRE, GABRG1, GABRG2, GABRG3, GABRP, GABRQ, GABRR1, GABRR2, GABRR3, TSPO | CYP2C9, CYP3A4, CYP3A5, CYP3A7 | | |
| Amobarbital | CHRNA4, CHRNA7, GABRA1, GABRA2, GABRA3, GABRA4, GABRA5, GABRA6, GABRB1, GABRB2, GABRB3, GABRD, GABRE, GABRG1, GABRG2, GABRG3, GABRP, GABRQ, GRIA2, GRIK2 | CYP2A6 | | |
| Aprobarbital | CHRNA4, CHRNA7, GABRA1, GABRA2, GABRA3, GABRA4, GABRA5, | | | |

TABLE 7-continued

Anxiolytics and Hypnotics/sedatives [N05B|N05C]

| Drugs | Target protein | Enzyme protein | Carrier protein | Transporter protein |
|---|---|---|---|---|
| | GABRA6, GRIA2, GRIK2 | | | |
| Bromazepam | GABRA1, GABRA2, GABRA3, GABRA4, GABRA5, GABRA6, GABRB1, GABRB2, GABRB3, GABRD, GABRE, GABRG1, GABRG2, GABRG3, GABRP, GABRQ, GABRR1, GABRR2, GABRR3 | CYP1A2, CYP2C19, CYP2E1, CYP3A4 | | |
| Buspirone | DRD2, HTR1A | CYP2D6, CYP3A4, CYP3A5, CYP3A7 | ABCB1 | |
| Butethal | CHRNA4, CHRNA7, GABRA1, GABRA2, GABRA3, GABRA4, GABRA5, GABRA6, GRIA2, GRIK2 | | | |
| Chlordiazepoxide | GABRA1, GABRA2, GABRA3, GABRA4, GABRA5, GABRA6, GABRB1, GABRB2, GABRB3, GABRD, GABRE, GABRG1, GABRG2, GABRG3, GABRP, GABRQ, GABRR1, GABRR2, GABRR3 | CYP2D6, CYP3A4 | | |
| Cinolazepam | GABRA1, GABRA2, GABRA3, GABRA5, GABRB1, GABRB2, GABRB3, GABRD, GABRE, GABRG1, GABRG2, GABRG3, GABRP, GABRR1, GABRR2, GABRR3 | | | |
| Clobazam | GABRA1, GABRA2, GABRA3, GABRA4, GABRA5, GABRA6, GABRB1, GABRB2, | CYP2B6, CYP2C18, CYP2C19, CYP3A4 | | |

TABLE 7-continued

Anxiolytics and Hypnotics/sedatives [N05B|N05C]

| Drugs | Target protein | Enzyme protein | Carrier protein | Transporter protein |
|---|---|---|---|---|
| | GABRB3, GABRD, GABRE, GABRG1, GABRG2, GABRG3, GABRP, GABRQ, GABRR1, GABRR2, GABRR3 | | | |
| Clorazepate | GABRA1, GABRA2, GABRA3, GABRA4, GABRA5, GABRA6, GABRB1, GABRB2, GABRB3, GABRD, GABRE, GABRG1, GABRG2, GABRG3, GABRP, GABRQ, GABRR1, GABRR2, GABRR3, TSPO | CYP3A4 | | |
| Clotiazepam | GABRA1, GABRA2, GABRA3, GABRA4, GABRA5, GABRA6, GABRB1, GABRB2, GABRB3, GABRD, GABRE, GABRG1, GABRG2, GABRG3, GABRP, GABRQ, GABRR1, GABRR2, GABRR3 | CYP2B6, CYP2C18, CYP2C19, CYP3A4 | | |
| Dexmedetomidine | ADRA2A, ADRA2B, ADRA2C | | | |
| Diazepam | GABRA1, GABRA2, GABRA3, GABRA4, GABRA5, GABRA6, GABRB1, GABRB2, GABRB3, GABRD, GABRE, GABRG1, GABRG2, GABRG3, GABRP, GABRQ, GABRR1, GABRR2, GABRR3, TSPO | CYP1A2, CYP2B6, CYP2C18, CYP2C19, CYP2C8, CYP2C9, CYP3A4, CYP3A5, CYP3A7, PTGS1 | ABCB1 | ALB |
| Estazolam | GABRA1, GABRA2, GABRA3, GABRA4, | CYP3A4 | | |

TABLE 7-continued

| Anxiolytics and Hypnotics/sedatives [N05B|N05C] | | | | |
|---|---|---|---|---|
| Drugs | Target protein | Enzyme protein | Carrier protein | Transporter protein |
| | GABRA5, GABRA6, GABRB1, GABRB2, GABRB3, GABRD, GABRE, GABRG1, GABRG2, GABRG3, GABRP, GABRQ, GABRR1, GABRR2, GABRR3 | | | |
| Ethchlorvynol | GABRA1, GABRA2, GABRA3, GABRA4, GABRA5, GABRA6, GABRB1, GABRB2, GABRB3 | | | |
| Fludiazepam | GABRA1, GABRA2, GABRA3, GABRA4, GABRA5, GABRA6, GABRB1, GABRB2, GABRB3, GABRD, GABRE, GABRG1, GABRG2, GABRG3, GABRP, GABRQ, GABRR1, GABRR2, GABRR3 | | | |
| Flunitrazepam | GABRA1, GABRA2, GABRA3, GABRA4, GABRA5, GABRA6, GABRB1, GABRB2, GABRB3, GABRD, GABRE, GABRG1, GABRG2, GABRG3, GABRP, GABRQ, TSPO | CYP1A2, CYP2A6, CYP2B6, CYP2C19, CYP2C9, CYP3A4, UGT2B7 | | |
| Flurazepam | GABRA1, GABRA2, GABRA3, GABRA4, GABRA5, GABRA6, GABRB1, GABRB2, GABRB3, GABRD, GABRE, GABRG1, GABRG2, GABRG3, GABRP, GABRQ, | CYP2A6, CYP2C19, CYP2E1, CYP3A4 | | ABCB1 |

TABLE 7-continued

Anxiolytics and Hypnotics/sedatives [N05B|N05C]

| Drugs | Target protein | Enzyme protein | Carrier protein | Transporter protein |
|---|---|---|---|---|
| | GABRR1, GABRR2, GABRR3 | | | |
| Glutethimide | GABRA1, GABRA2, GABRA3, GABRA4, GABRA5, GABRA6, GABRB1, GABRB2, GABRB3, GABRD, GABRE, GABRG1, GABRG2, GABRG3, GABRP, GABRQ | CYP11A1, CYP2D6 | | |
| Halazepam | GABRA1, GABRA2, GABRA3, GABRA5, GABRB1, GABRB2, GABRB3, GABRD, GABRE, GABRG1, GABRG2, GABRG3, GABRP, GABRR1, GABRR2, GABRR3 | | | |
| Heptabarbital | CHRNA4, CHRNA7, GABRA1, GABRA2, GABRA3, GABRA4, GABRA5, GABRA6, GRIA2, GRIK2 | | | |
| Hexobarbital | CHRNA4, CHRNA7, GABRA1, GABRA2, GABRA3, GABRA4, GABRA5, GABRA6, GABRB1, GABRB2, GABRB3, GABRD, GABRE, GABRG1, GABRG2, GABRG3, GABRP, GABRQ, GRIA2, GRIK2 | CYP1A2, CYP2C19, CYP2C9, CYP2E1, CYP3A4, PTGS1 | | |
| Hydroxyzine | HRH1 | CYP2D6, CYP3A4, CYP3A5 | | |
| Ketazolam | GABRA1, GABRB1, GABRD, GABRE, GABRG1, TSPO | CYP3A4 | ABCB1 | ALB |
| Lorazepam | GABRA1, GABRA2, GABRA3, GABRA4, GABRA5, | | | |

TABLE 7-continued

Anxiolytics and Hypnotics/sedatives [N05B|N05C]

| Drugs | Target protein | Enzyme protein | Carrier protein | Transporter protein |
|---|---|---|---|---|
| | GABRA6, GABRB1, GABRB2, GABRB3, GABRD, GABRE, GABRG1, GABRG2, GABRG3, GABRP, GABRQ, GABRR1, GABRR2, GABRR3, TSPO | | | |
| Melatonin | ASMT, CALM1, CALR, EPX, ESR1, MPO, MTNR1A, MTNR1B, NQO2, RORB | ASMT, CYP19A1, CYP1A1, CYP1A2, CYP1B1, CYP2C19, CYP2C9, IDO1, MPO | SLC22A8 | |
| Meprobamate | GABRA1, GABRA2, GABRA3, GABRA4, GABRA5, GABRA6, GABRB1, GABRB2, GABRB3, GABRD, GABRE, GABRG1, GABRG2, GABRG3, GABRP, GABRQ | CYP2C19, CYP2E1 | ABCB1 | |
| Methaqualone | GABRA1, GABRA2, GABRA3, GABRA4, GABRA5, GABRA6, GABRB1, GABRB2, GABRB3, GABRD, GABRE, GABRG1, GABRG2, GABRG3, GABRP, GABRQ | CYP3A4 | | |
| Methohexital | GABRA1 | | | |
| Methyprylon | GABRA1 | CYP2D6 | | |
| Midazolam | GABRA1, GABRA2, GABRA3, GABRA4, GABRA5, GABRA6, GABRB1, GABRB2, GABRB3, GABRD, GABRE, GABRG1, GABRG2, GABRG3, GABRP, GABRQ, GABRR1, GABRR2, GABRR3 | CYP2B6, CYP3A4, CYP3A5, CYP3A7, CYP4B1 | ABCB1, SLC22A1 | |

TABLE 7-continued

Anxiolytics and Hypnotics/sedatives [N05B|N05C]

| Drugs | Target protein | Enzyme protein | Carrier protein | Transporter protein |
|---|---|---|---|---|
| Nitrazepam | GABRA1, GABRA2, GABRA3, GABRA4, GABRA5, GABRA6, GABRB1, GABRB2, GABRB3, GABRD, GABRE, GABRG1, GABRG2, GABRG3, GABRP, GABRQ, GABRR1, GABRR2, GABRR3, SCN1A | CYP3A4 | | ABCB1 |
| Oxazepam | GABRA1, GABRA2, GABRA3, GABRA4, GABRA5, GABRA6, GABRB1, GABRB2, GABRB3, GABRD, GABRE, GABRG1, GABRG2, GABRG3, GABRP, GABRQ, GABRR1, GABRR2, GABRR3 | CYP3A4, CYP3A43, CYP3A5, CYP3A7 | | |

TABLE 8

Beta blocking agents [C07]

| Drugs | Target protein | Enzyme protein | Carrier protein | Transporter protein |
|---|---|---|---|---|
| Acebutolol | ADRB1, ADRB2 | CYP2D6 | | ABCB1, SLC22A1 |
| Alprenolol | ADRB1, ADRB2, ADRB3, HTR1A | CYP2D6 | | |
| Atenolol | ADRB1, LTF, PLA2G2E | | | ABCB1 |
| Betaxolol | ADRB1, ADRB2 | CYP1A2, CYP2D6 | | |
| Bevantolol | ADRA1A, ADRA1B, ADRA1D, ADRB1, ADRB2 | | | |
| Bisoprolol | ADRB1, ADRB2 | CYP2D6, CYP3A4 | | |
| Bopindolol | ADRB1, ADRB2, ADRB3, HTR1A, HTR1B | | | |
| Bupranolol | ADRB1, ADRB2, ADRB3 | | | |
| Carteolol | ADRB1, ADRB2, ADRB3 | CYP2D6 | | |
| Carvedilol | ADRA1A, ADRA1B, ADRA1D, ADRB1, ADRB2, ADRB3, GJA1, KCNH2, NDUFC2, NPPB, VCAM1, VEGFA | CYP1A1, CYP1A2, CYP2C9, CYP2D6, CYP2E1, CYP3A4, PTGS1, XDH | ABCB1 | |
| Esmolol | ADRB1 | | | |
| Labetalol | ADRA1A, ADRA1B, ADRA1D, ADRB1, ADRB2, ADRB3 | CYP2D6 | | |
| Metoprolol | ADRB1, ADRB2 | CYP2C19, CYP2D6 | | ABCB1, SLC22A2 |
| Nadolol | ADRB1, ADRB2, ADRB3 | | | ABCB1 |
| Nebivolol | ADRB1, ADRB2 | CYP2D6 | | |
| Oxprenolol | ADRB1, ADRB2, ADRB3 | CYP2D6 | | SLC22A2 |
| Penbutolol | ADRB1, ADRB2, ADRB3 | | ORM1 | |
| Pindolol | ADRB1, ADRB2, ADRB3, HTR1A, HTR1B | CYP2D6 | | SLC22A2 |
| Practolol | ADRB1 | | | |
| Propranolol | ADRB1, ADRB2, ADRB3, HTR1A | CYP1A1, CYP1A2, | ABCB1, ORM1 | SLC22A2 |

TABLE 8-continued

Beta blocking agents [C07]

| Drugs | Target protein | Enzyme protein | Carrier protein | Transporter protein |
|---|---|---|---|---|
| | HTR1B | CYP2C19, CYP2D6, CYP3A4, CYP3A5, CYP3A7 | | |
| Sotalol | ADRB1, ADRB2, KCNH2 | | | |
| Timolol | ADRB1, ADRB2, ADRB3, LYZ | CYP2C19, CYP2D6 | ABCB1 | |

TABLE 9

Calcium channel blockers [C08]

| Drugs | Target protein | Enzyme protein | Carrier protein | Transporter protein |
|---|---|---|---|---|
| Amlodipine | CA1, CACNA1B, CACNA1C, CACNA1D, CACNA1F, CACNA1S, CACNA2D1, CACNA2D3, CACNB1, CACNB2 | CYP1A1, CYP1A2, CYP2A6, CYP2B6, CYP2C8, CYP2C9, CYP2D6, CYP3A4, CYP3A5, CYP3A7 | ABCB1 | |
| Bepridil | ATP1A1, CACNA1A, CACNA1C, CACNA1D, CACNA1F, CACNA1G, CACNA1H, CACNA1I, CACNA1S, CACNA2D2, CALM1, KCNA5, KCND3, KCNH2, KCNJ12, KCNJ3, KCNJ5, KCNJ8, KCNQ1, PDE1A, PDE1B, TNNC1 | CYP2C9, CYP2D6, CYP3A4 | ABCB1 | |
| Diltiazem | CACNA1C, CACNA1D, CACNA1F, CACNA1S, CACNG1 | CYP2C19, CYP2C8, CYP2C9, CYP2D6, CYP3A4, CYP3A5, CYP3A7 | ABCB1 | |
| Felodipine | CACNA1C, CACNA1D, CACNA1F, CACNA1H, CACNA1S, CACNA2D1, CACNA2D2, CACNB2, CALM1, NR3C2, PDE1A, PDE1B, TNNC1, TNNC2 | CYP2C8, CYP2C9, CYP2D6, CYP3A4, CYP3A5, CYP3A7 | ABCB1 | |
| Isradipine | CACNA1C, CACNA1D, CACNA1F, CACNA1H, CACNA1S, CACNA2D1, CACNA2D2, CACNB2 | CYP3A4 | | |
| Lercanidipine | CACNG1 | CYP2D6, CYP3A4, CYP3A5, CYP3A7 | | |
| Losartan | AGTR1 | CYP1A2, CYP2C19, CYP2C8, CYP2C9, CYP3A4, CYP3A5, UGT1A1, UGT1A10, UGT1A3, UGT2B17, UGT2B7 | ABCB1, SLC22A6 | |
| Mibefradil | CACNA1C, CACNA1D, CACNA1F, | CYP11B1, CYP11B2, CYP1A1, CYP1A2, CYP2D6, CYP3A4, | ABCB1 | |

TABLE 9-continued

Calcium channel blockers [C08]

| Drugs | Target protein | Enzyme protein | Carrier protein | Transporter protein |
|---|---|---|---|---|
| | CACNA1G, CACNA1H, CACNA1I, CACNA1S, CACNB1, CACNB2, CACNB3, CACNB4 | CYP3A5, CYP3A7 | | |
| Nicardipine | ADRA1A, ADRA1B, ADRA1D, CACNA1C, CACNA1D, CACNA1F, CACNA1S, CACNA2D1, CACNB2, CALM1, CHRM1, CHRM2, CHRM3, CHRM4, CHRM5, PDE1A, PDE1B | CYP2B6, CYP2C19, CYP2C8, CYP2C9, CYP2D6, CYP2E1, CYP3A4, CYP3A5 | ABCB1 | |
| Nifedipine | CACNA1C, CACNA1D, CACNA1F, CACNA1H, CACNA1S, CACNA2D1, CACNB2, CALM1, KCNA1 | CYP1A1, CYP1A2, CYP2A6, CYP2B6, CYP2C8, CYP2C9, CYP2D6, CYP2E1, CYP3A4, CYP3A5, CYP3A7 | ABCB1, ABCC2, ABCC3 | |
| Nilvadipine | CACNA1C, CACNA1D CACNA1F, CACNA1S, CACNA2D1, CACNA2D3, CACNB2 | CYP1A2, CYP2A6, CYP2C19, CYP2C8, CYP2C9, CYP2E1, CYP3A4 | | |
| Nimodipine | AHR, CACNA1C, CACNA1D, CACNA1F, CACNA1S, CACNB1, CACNB2, CACNB3, CACNB4, NR3C2 | CYP3A4, CYP3A5 | | |
| Nisoldipine | CACNA1C, CACNA1D, CACNA1S, CACNA2D1, CACNB2 | CYP1A2, CYP3A4 CYP3A5, CYP3A7, | ABCB1 | |
| Nitrendipine | CACNA1C, CACNA1D, CACNA1F, CACNA1H CACNA1S, CACNA2D1, CACNA2D2, CACNB2, CACNG1 | CYP3A4, CYP3A5 CYP3A7 | ABCB1 | |
| Perhexiline | CPT1A, CPT2 | CYP2B6, CYP2D6 CYP3A4 | | |
| Verapamil | CACNA1A, CACNA1B, CACNA1C, CACNA1D, CACNA1F, CACNA1G, CACNA1I, CACNA1S, CACNB1, CACNB2, CACNB3, CACNB4, | CYP1A2, CYP2B6, CYP2C18, CYP2C19, CYP2C8, CYP2C9, CYP2D6, CYP3A4, CYP3A5, CYP3A7 | ABCB1, ABCB11, ABCC1, ABCC10, ABCC2, ABCC3, ABCC4, ABCG2, SLC22A1, SLC22A4, SLC22A5, SLCO1A2, SLCO1B1 | |

TABLE 9-continued

| Calcium channel blockers [C08] | | | |
|---|---|---|---|
| Drugs | Target protein | Enzyme protein | Carrier protein | Transporter protein |
| | KCNA10, KCNA3, KCNA7, KCNC2, KCNH2, KCNJ11, KCNJ6, SCN5A, SLC6A4 | | | |

TABLE 10

| Diuretics [C03] | | | | |
|---|---|---|---|---|
| Drugs | Target protein | Enzyme protein | Carrier protein | Transporter protein |
| Amiloride | ABP1, ASIC1, ASIC2, PLAU, SCNN1A, SCNN1B, SCNN1D, SCNN1G, SLC9A1 | ABP1 | SLC22A1, SLC22A2, SLC22A4 | |
| Bendroflumethiazide | CA1, CA2, CA4, KCNMA1, SLC12A3 | | | |
| Bumetanide | CFTR, SLC12A1, SLC12A2, SLC12A4, SLC12A5 | | SLC10A1, SLC22A11, SLC22A6, SLC22A7, SLC22A8, SLCO1A2 | |
| Chlorothiazide | CA1, CA2, CA4, SLC12A3 | | SLC22A6 | |
| Chlorthalidone | CA2, SLC12A1, SLC12A3 | | | |
| Conivaptan | AVPR1A, AVPR2 | CYP3A4 | | |
| Cyclothiazide | CA1, CA2, CA4, FXYD2 | | SLC22A6 | |
| Eplerenone | NR3C2 | CYP11B2, CYP3A4, CYP3A5, CYP3A7 | | |
| Ethacrynic acid | ATP1A1, SLC12A1, SLC12A2 | GSTA2 | SLC22A6 | ALB |
| Furosemide | CA2, GABRA1, GABRA2, GABRA3, GABRA4, GABRA5, GABRA6, SLC12A1, SLC12A2 | PGD | ABCC2, ABCC4, SLC22A11, SLC22A5, SLC22A6, SLC22A8, SLCO2A1 | ALB |
| Hydrochlorothiazide | CA1, CA12, CA2, CA4, CA9, KCNMA1, SLC12A3 | | SLC22A6 | |
| Hydroflumethiazide | ATP1A1, CA1, CA12, CA2, CA4, CA9, KCNMA1, SLC12A1, SLC12A3 | | | |
| Indapamide | CA2, KCNE1, KCNQ1, SLC12A3 | CYP3A4 | | |
| Methyclothiazide | CA1, CA2, CA4, SLC12A1, SLC12A3 | | | |
| Metolazone | SLC12A3 | | | |
| Polythiazide | SLC12A3 | | | |
| Quinethazone | CA1, CA2, SLC12A1, SLC12A2, SLC12A3 | | | |

TABLE 10-continued

Diuretics [C03]

| Drugs | Target protein | Enzyme protein | Carrier protein | Transporter protein |
|---|---|---|---|---|
| Spironolactone | AR, NR3C2 | CYP11B1, CYP2C8 | ABCB1, ABCC2, SLCO1A2 | |
| Tolvaptan | AVPR2 | | | |
| Torasemide | SLC12A1, SLC12A2 | CYP2C19, CYP2C8, CYP2C9, PTGS1 | | |
| Triamterene | SCNN1A, SCNN1B, SCNN1D, SCNN1G | CYP1A2 | | |
| Trichlormethiazide | ATP1A1, CA1, CA2, CA4, SLC12A1, SLC12A3 | | | |
| Theobromine | ADORA1, ADORA2A, PDE4B | CYP1A2, CYP2E1 | | |

TABLE 11

Drugs for obstructive airway diseases [R03]

| Drugs | Target protein | Enzyme protein | Carrier protein | Transporter protein |
|---|---|---|---|---|
| Aminophylline | ADORA1, ADORA2A, ADORA3, PDE3A, PDE3B | CYP1A2, CYP2E1, CYP3A4 | | |
| Amlexanox | FGF1, IL3, S100A12, S100A13 | | | |
| Bambuterol | ADRB2 | BCHE | | |
| Beclomethasone | NR3C1 | CYP3A5 | | SERPINA6 |
| Betamethasone | ANXA1, NOS2, NR0B1, NR3C1 | CYP11A1, CYP17A1, CYP19A1, CYP1A1, CYP1B1, CYP2A6, CYP2B6, CYP2C19, CYP2C8, CYP2C9, CYP2D6, CYP2E1, CYP3A4, CYP3A43, CYP3A5, CYP3A7, CYP4A11 | ABCB1, ABCB11, ABCC2, ABCG2, SLCO1A2 | |
| Betamethasone valerate | NR3C1 | | | |
| Bitolterol | ADRB2 | | | |
| Budesonide | NR3C1 | CYP3A4 | | |
| Ciclesonide | NR3C1 | CES1, CYP2D6, CYP3A4 | | SERPINA6 |
| Clenbuterol | ADRB1, ADRB2, ADRB3, NGF, TNF | CYP1A1, CYP1A2 | | |
| Cromoglicate | KCNMA1, S100P | | | |
| Dexamethasone propionate | NR3C1 | | | |
| Dyphylline | ADORA1, ADORA2A, PDE4A, PDE4B, PDE4C, PDE4D, PDE7A, PDE7B | | | |
| Ephedrine | ACHE, ADRA1A, ADRA1B, ADRA1D, ADRA2A, ADRA2B, ADRA2C, ADRB1, ADRB2, | CYP2D6, MAOA | | |

TABLE 11-continued

Drugs for obstructive airway diseases [R03]

| Drugs | Target protein | Enzyme protein | Carrier protein | Transporter protein |
|---|---|---|---|---|
| Epinephrine | ADRB3, SLC18A2, SLC6A2, SLC6A3, SLC6A4 ADRA1A, ADRA1B, ADRA1D, ADRA2A, ADRA2B, ADRA2C, ADRB1, ADRB2, ADRB3, PAH | CYP1A2 CYP2C9, CYP3A4 | SLC22A1, SLC22A2, SLC22A5 | |
| Fenoterol | ADRB1, ADRB2, ADRB3 | | | |
| Flunisolide | NR3C1 | CYP3A4 | | SERPINA6 |
| Fluticasone Propionate | NR3C1, NR3C2, PGR, PLA2G4A | CYP3A4, CYP3A5, CYP3A7 | | SERPINA6 |
| Fluticasone furoate | NR3C1 | CYP3A4 | | |
| Formoterol | ADRB2 | CYP2A6, CYP2C19, CYP2C9, CYP2D6 | | |
| Ibudilast | CYSLTR1, PDE3A, PDE3B, PDE4A, PDE4B, PDE4C, PDE4D, PTGIR | | | |
| Indacaterol | ADRB2 | | | |
| Ipratropium | CHRM1, CHRM2, CHRM3, CHRM4, CHRM5 | CYP2D6, CYP3A4 | SLC22A4, SLC22A5 | |
| Isoetharine | ADRB1, ADRB2 | | | |
| Isoproterenol | ADRB1, ADRB2, ADRB3, MAPK1, PIK3R1, PIK3R2, PIK3R3 | CYP1A1 | | |
| Mometasone | NR3C1 | CYP2C8, CYP3A4 | | |
| Mometasone furoate | NR3C1 | CYP3A4 | | |
| Montelukast | ALOX5, CYSLTR1 | CYP2A6, CYP2C8, CYP2C9, CYP3A4, PTGS1 | SLCO2B1 | |
| Nedocromil | CYSLTR1, CYSLTR2, FPR1, HSP90AA1, PTGDR | | | |
| Omalizumab | FCER1A, MS4A2 | | | |
| Orciprenaline | ADRB2 | | | |
| Oxtriphylline | ADORA1, ADORA2A, PDE3A, PDE4A | CYP1A2 | SLC22A7 | |
| Pirbuterol | ADRB1, ADRB2 | | | |
| Pranlukast | CYSLTR1, CYSLTR2, IL5, MUC2, NFKB1, RNASE3, TNF | CYP2C9, CYP3A4 | ABCC2 | |
| Procaterol | ADRB2 | | | |
| Roflumilast | PDE4A, PDE4B, PDE4C, PDE4D | | | |
| Salbutamol | ADRB1, ADRB2 | CYP3A4 | | |
| Salmeterol | ADRB2 | CYP2C8, CYP3A4, CYP3A5, CYP3A7 | | |

TABLE 11-continued

Drugs for obstructive airway diseases [R03]

| Drugs | Target protein | Enzyme protein | Carrier protein | Transporter protein |
|---|---|---|---|---|
| Salmeterol xinafoate | ADRB2 | CYP3A4 | | |
| Salmeterol xinafoate-fluticasone propionate mixt | | CYP3A4 | | |
| Terbutaline | ADRB2 | BCHE | | |
| Theophylline | ADORA1, ADORA2A, ADORA2B, PDE3A, PDE4A, PDE4B, PDE5A | ADA, CYP1A1, CYP1A2, CYP1B1, CYP2C8, CYP2C9, CYP2D6, CYP2E1, CYP3A4 | SLC22A7 | |
| Tiotropium | CHRM1, CHRM2, CHRM3 | CYP2D6, CYP3A4 | SLC22A4, SLC22A5 | |
| Triamcinolone | NR3C1 | | | SERPINA6 |
| Zafirlukast | CYSLTR1 | CYP1A2, CYP2C19, CYP2C8, CYP2C9, CYP2D6, CYP2E1, CYP3A4, PTGS1 | | |

TABLE 12

Lipid modifying agents [C10]

| Drugs | Target protein | Enzyme protein | Carrier protein | Transporter protein |
|---|---|---|---|---|
| Atorvastatin | AHR, DPP4, HMGCR | CYP2B6, CYP2C19, CYP2C8, CYP2C9, CYP2D6, CYP3A4, CYP3A5, CYP3A7 | ABCB1, ABCC1, ABCC4, ABCC5, SLCO1A2, SLCO1B1 | |
| Bezafibrate | PPARA, PPARD, PPARG | CYP1A1, CYP2C8, CYP3A4 | SLCO1B1 | |
| Cerivastatin | HMGCR | CYP2B6, CYP2C19, CYP2C8, CYP2C9, CYP2D6, CYP3A4, CYP3A5, CYP3A7 | ABCB1, ABCC2, ABCG2, SLCO1B1 | |
| Clofibrate | PPARA | CYP1A1, CYP2A6, CYP2B6, CYP2E1, CYP3A4, CYP4A11, GSTA2 | | |
| Ezetimibe | ANPEP, NPC1L1, SOAT1 | CYP3A4, UGT1A1, UGT1A3, UGT2B7 | ABCB1, ABCC2, SLCO1B1 | |
| Fenofibrate | MMP20, PPARA | CYP2C8, CYP2C9, CYP3A4 | | |
| Fluvastatin | HMGCR | CYP1A1, CYP1A2, CYP2B6, CYP2C19, CYP2C8, CYP2C9, CYP2D6, CYP3A4 | | |
| Gemfibrozil | PPARA | CYP1A2, CYP2C19, CYP2C8, CYP2C9, CYP3A4 | SLCO1B1 | |
| Lovastatin | HDAC2, HMGCR, ITGAL | CYP2C19, CYP2C8, CYP2C9, CYP2D6, CYP3A4, CYP3A5, CYP3A7, PON3 | ABCB1, SLCO1A2, SLCO1B1 | |
| Niacin | HCAR2, HCAR3, NNMT, QPRT | CYP2D6 | SLC16A1, SLC22A5, SLCO2B1 | |
| Pravastatin | HMGCR | CYP2C8, CYP2C9, CYP2D6, CYP3A4, CYP3A5 | ABCB1, ABCB11, ABCC2, ABCG2, SLC22A11, SLC22A6, SLC22A7, SLC22A8, | |

TABLE 12-continued

Lipid modifying agents [C10]

| Drugs | Target protein | Enzyme protein | Carrier protein | Transporter protein |
|---|---|---|---|---|
| | | | SLCO1A2, SLCO1B1, SLCO2B1 | |
| Probucol | ABCA1 | | | |
| Rosuvastatin | HMGCR | CYP2C19, CYP2C9, CYP3A4, CYP3A5 | ABCC1, ABCC4 | |
| Simvastatin | HMGCR, ITGB2 | CYP2B6, CYP2C19, CYP2C8, CYP2C9, CYP2D6, CYP3A4, CYP3A5, CYP3A7 | ABCB1, SLCO1A2, SLCO1B1 | |
| Levothyroxine | THRA, THRB, TPO | CYP2C8, CYP3A4 | ABCB1, SLC16A2, SLCO1C1 | ALB, SERPINA7, TTR |

TABLE 13

Proton Pump Inhibitors [A02BC]

| Drugs | Target protein | Enzyme protein | Carrier protein | Transporter protein |
|---|---|---|---|---|
| Lansoprazole | ATP4A, ATP4B | CYP1A1, CYP1A2, CYP1B1, CYP2C18, CYP2C19, CYP2C8, CYP2C9, CYP2D6, CYP3A4, CYP4A11 | ABCB1, ABCG2 | |
| Omeprazole | ATP4A, ATP4B | CYP11A1, CYP1A1, CYP1A2, CYP1B1, CYP2C18, CYP2C19, CYP2C8, CYP2C9, CYP2D6, CYP3A4 | ABCB1, ABCC3, ABCG2 | |
| Pantoprazole | ATP4A, ATP4B | CYP1A2, CYP2C19, CYP2C9, CYP3A4 | ABCB1, ABCG2, SLCO1B1 | |
| Rabeprazole | ATP4A, ATP4B | CYP1A1, CYP1A2, CYP2C19, CYP2C9, CYP2D6, CYP3A4 | ABCG2 | |

TABLE 14

Sex hormones and modulators of the genital system [G03]

| Drugs | Target protein | Enzyme protein | Carrier protein | Transporter protein |
|---|---|---|---|---|
| Allylestrenol | ESR1, PGR | CYP3A4 | | |
| Chlorotrianisene | ESR1 | | | |
| Choriogonadotropin alfa | FSHR, LHCGR | | | |
| Clomifene | ESR1, ESR2 | CYP11A1, CYP19A1, CYP1A1, CYP1A2, CYP2A6, CYP2E1, CYP3A4 | ABCB1 | |
| Conjugated estrogens | ESR1, ESR2 | | | |
| Cyproterone | AR | CYP19A1 | | |
| Danazol | AR, CCL2, ESR1, GNRHR, GNRHR2, PGR | CYP19A1, CYP3A4 | | SHBG |
| Desogestrel | ESR1, PGR | | | |
| Dienestrol | ESR1, ESR2 | | | |
| Diethylstilbestrol | AKR1C1, ESR1, ESR2, ESRRG | COMT, CYP19A1, CYP2A6, CYP2C8, CYP2C9, CYP2E1, CYP3A4 | ABCB1, ABCG2 | TTR |
| Dydrogesterone | PGR | | | |
| Estradiol | ESR1, ESR2, NR1I2 | CYP1A1, CYP1A2, CYP1B1, CYP2C19, CYP2C8, CYP2C9, | ABCB1, ABCC10, ABCG2, | ALB, FABP2, SHBG |

TABLE 14-continued

Sex hormones and modulators of the genital system [G03]

| Drugs | Target protein | Enzyme protein | Carrier protein | Transporter protein |
|---|---|---|---|---|
| | | CYP3A4, CYP3A5, CYP3A7, UGT1A1 | SLC22A1, SLC22A11, SLC22A2, SLC22A3, SLCO1A2, SLCO1B1, SLCO2B1 | |
| Estradiol-levonorgestrel mixt | | CYP3A4 | | |
| Estriol | ESR1, ESR2, NCOA5 | | ABCB1, SLCO1A2 | |
| Estrone | ESR1, ESR2 | COMT, CYP1A1, CYP1A2, CYP1B1, CYP2B6, CYP2C9, CYP2E1, CYP3A4, CYP3A5, CYP4A11 | ABCB1, ABCC1, ABCC11, ABCC2, ABCC3, ABCC4, ABCG2, SLC10A1, SLC22A10, SLC22A11, SLC22A6, SLC22A8, SLCO1A2, SLCO1B1, SLCO1B3, SLCO1C1, SLCO2B1, SLCO3A1, SLCO4A1 | ALB |
| Ethinyl Estradiol | ESR1, ESR2, NR1I2 | CYP2C8, CYP3A4 | ABCB1, ABCB11, ABCC2, SLC10A1 | |
| Ethynodiol | ESR1, PGR | | | |
| Etonogestrel | ESR1, PGR | CYP3A4 | | |
| Fluoxymesterone | AR, ESR1, NR3C1, PRLR | | | SHBG |
| Follitropin alfa (genetical recombination) | FSHR | | | |
| Follitropin beta | FSHR | | | |
| Follitropin beta (genetical recombination) | FSHR | | | |
| Hydroxyprogesterone caproate | PGR | | | |
| Levonorgestrel | AR, ESR1, PGR, SRD5A1 | CYP19A1, CYP3A4 | | |
| Lutropin alfa | LHCGR | | | |
| Medroxyprogesterone | ESR1, PGR | CYP2C8, CYP2C9, CYP3A4, HSD3B2 | | |
| Megestrol | NR3C1, PGR | | ABCB1 | |
| Methyltestosterone | AR | CYP19A1, CYP2B6, CYP3A4 | SLC22A8, SLCO1A2 | ALB, SHBG |
| Mifepristone | NR3C1, PGR | CYP2D6, CYP3A4, CYP3A5, CYP3A7 | ABCB1, ABCC1 | |
| Nandrolone phenpropionate | AR | CYP19A1 | | |
| Norethindrone | PGR | CYP2C19, CYP3A4, CYP3A5, CYP3A7 | ABCB1 | |
| Progesterone | CYP17A1, ESR1, NR3C2, PGR | CYP17A1, CYP1A1, CYP1A2, CYP1B1, CYP2A6, CYP2C19, CYP2C8, CYP2C9, CYP2D6, CYP3A4, CYP3A5, CYP3A7 | ABCB1, ABCB11, ABCC1, SLC10A1, SLC22A1, SLC22A2, SLC22A3 | |
| Raloxifene | ESR1, ESR2 | AOX1, CYP19A1, CYP2B6, CYP2C8, CYP3A4 | | |
| Synthetic conjugated estrogens, B | ESR1, ESR2 | | | |

TABLE 14-continued

Sex hormones and modulators of the genital system [G03]

| Drugs | Target protein | Enzyme protein | Carrier protein | Transporter protein |
|---|---|---|---|---|
| Testosterone | AKR1C1, AKR1C2, AR | CYP11A1, CYP19A1, CYP1A1, CYP1B1, CYP2A13, CYP2B6, CYP2C19, CYP2C8, CYP2C9, CYP3A4, CYP3A43, CYP3A5, CYP3A7, MAOA | ABCB1, ABCG2, SLC10A1, SLC22A1, SLC22A3, SLC22A4, SLC22A7, SLC22A8, SLCO1A2 | ALB, SHBG |
| Testosterone Propionate | AR | | | |
| Urofollitropin | FSHR | | | |

TABLE 15

Thyroid therapy [H03]

| Drugs | Target protein | Enzyme protein | Carrier protein | Transporter protein |
|---|---|---|---|---|
| Carbimazole | TPO | | | |
| Liotrix | THRA, THRB | CYP2C8 | ABCB1, SLC10A1, SLC16A10, SLC16A2, SLC22A8, SLCO1A2, SLCO1B1, SLCO1B3, SLCO1C1, SLCO4A1, SLCO4C1 | ALB, SERPINA7, TTR |
| Methimazole | TPO | CYP1A2, CYP2A6, CYP2B6, CYP2C19, CYP2C9, CYP2D6, CYP2E1, CYP3A4 | | |
| Propylthiouracil | DIO1, DIO2, TPO | | | |

The individual genome sequence information used herein may be determined by using a well-known sequencing method. Further, services such as Complete Genomics, BGI (Beijing Genome Institute), Knome, Macrogen, and DNA-Link which provide commercialized services may be used, but the present invention is not limited thereto.

In the present invention, gene sequence variation information present in an individual genome sequence may be extracted by using various methods, and may be acquired through sequence comparison analysis by using a program, for example, ANNOVAR (Wang et al., Nucleic Acids Research, 2010; 38(16): e164), SVA (Sequence Variant Analyzer) (Ge et al., Bioinformatics. 2011; 27(14): 1998-2000), BreakDancer (Chen et al., Nat Methods. 2009 September; 6(9):677-81), and the like, which compare a sequence to a reference group, for example, the genome sequence of HG19.

The gene sequence variation information may be received/acquired through a computer system: In this aspect, the method of the present invention may further include receiving the gene sequence variation information through a computer system. The computer system used in the present invention may include or access one or more databases including information about the gene involved in the pharmacodynamics or pharmacokinetics of a specific drug or drug group, for example, a gene encoding a target protein relevant to a drug, an enzyme protein involved in drug metabolism, a transporter protein, a carrier protein, or the like. These databases may include a public or non-public database or a knowledge base, which provides information about gene/protein/drug-protein interaction, and the like, including such as DrugBank (http://www.drugbank.ca/), KEGG Drug (http://www.genome.jp/kegg/drug/), and PharmGKB (http://www.pharmgkb.org/), but are not limited thereto.

In the present invention, the predetermined drug or drug group may be information input by a user, information input from a prescription, or information input from a database including information about a drug effective in treating a specific disease. The prescription may include an electronic prescription, but is not limited thereto.

The term "gene sequence variation score" used herein refers to a numerical score of a degree of the individual genome sequence variation that causes an amino acid sequence variation (substitution, addition, or deletion) of a protein encoded by a gene or a transcription control variation and thus causes a significant change or damage to a structure and/or function of the protein when the genome sequence variation is found in an exon region of the gene encoding the protein. The gene sequence variation score can be calculated considering a degree of evolutionary conservation of amino acid in a genome sequence, a degree of an effect of a physical characteristic of modified amino acid on a structure or function of the corresponding protein.

The gene sequence variation score used for calculating the individual protein damage score and the individual drug score according to the present invention can be calculated by using a method known in the art. For example, the gene sequence variation score can be calculated from the gene sequence variation information by using an algorithm such as SIFT (Sorting Intolerant From Tolerant, Pauline C et al., Genome Res. 2001 May; 11(5): 863-874; Pauline C et al., Genome Res. 2002 March; 12(3): 436-446; Jing Hul et al., Genome Biol. 2012; 13(2): R9), PolyPhen, PolyPhen-2 (Polymorphism Phenotyping, Ramensky V et al., Nucleic Acids Res. 2002 September 1; 30(17): 3894-3900; Adzhubei I A et al., Nat Methods 7(4):248-249 (2010)), MAPP (Eric A. et al., Multivariate Analysis of Protein Polymorphism, Genome Research 2005; 15:978-986), Logre (Log R Pfam E-value, Clifford R. J et al., Bioinformatics 2004; 20:1006-1014), Mutation Assessor (Reva B et al., Genome Biol.

2007; 8:R232, http://mutationassessor.org/), Condel (Gonzalez-Perez A et al., The American Journal of Human Genetics 2011; 88:440-449, http://bg.upf.edu/fannsdb/), GERP (Cooper et al., Genomic Evolutionary Rate Profiling, Genome Res. 2005; 15:901-913, http://mendel.stanford.edu/SidowLab/downloads/gerp/), CADD (Combined Annotation-Dependent Depletion, http://cadd.gs.washington.edu/), MutationTaster, MutationTaster2 (Schwarz et al., MutationTaster2: mutation prediction for the deep-sequencing age. Nature Methods 2014; 11:361-362, http://www.mutationtaster.org/), PROVEAN (Choi et al., PLoS One. 2012; 7(10): e46688), PMut (Ferrer-Costa et al., Proteins 2004; 57(4): 811-819, http://mmb.pcb.ub.es/PMut/), CEO (Combinatorial Entropy Optimization, Reva et al., Genome Biol 2007; 8(11):R232), SNPeffect (Reumers et al., Bioinformatics. 2006; 22(17):2183-2185, http://snpeffect.vib.be), fathmm (Shihab et al., Functional Analysis through Hidden Markov Models, Hum Mutat 2013; 34:57-65, http://fathmm.biocompute.org.uk/), and the like, but the present invention is not limited thereto.

The above-described algorithms are configured to identify how much each gene sequence variation has an effect on a protein function, how much the effect damage the protein, or whether or not there are any other effects. These algorithms are basically configured to consider an amino acid sequence of a protein encoded by a corresponding gene and its relevant change caused by an individual gene sequence variation and thereby to determine an effect on a structure and/or function of the corresponding protein.

In an exemplary embodiment of the present invention, a SIFT (Sorting Intolerant From Tolerant) algorithm is used to calculate an individual gene sequence variation score. In the case of the SIFT algorithm, gene sequence variation information is input in the form of a VCF (Variant Call Format) file, and a degree of damage caused by each gene sequence variation to the corresponding gene is scored. In the case of the SIFT algorithm, as a calculated score is closer to 0, it is considered that a protein encoded by a corresponding gene is severely damaged and thus its function is damaged, and as the calculated score is closer to 1, it is considered that the protein encoded by the corresponding gene maintains its normal function.

In the case of another algorithm PolyPhen-2, the higher a calculated score is, it is considered that the more damaged a function of a protein encoded by a corresponding gene is.

Recently, a study (Gonzalez-Perez, A. & Lopez-Bigas, N. Improving the assessment of the outcome of nonsynonymous SNVs with a consensus deleteriousness score, Condel. The American Journal of Human Genetics, 2011; 88(4). 440-449) suggesting a Condel algorithm by comparing and combining SIFT, Polyphen2, MAPP, Logre, and Mutation Assessor was reported. In this study, the above-described five algorithms are compared by using HumVar and HumDiv (Adzhubei, I A et al., A method and server for predicting damaging missense mutations. Nature methods, 2010; 7(4): 248-249) as set of known data relating to gene sequence variations damaging a protein and gene sequence variations with less effect. As a result, 97.9% of the gene sequence variations damaging a protein and 97.3% of the gene sequence variations with less effect of HumVar were identically detected by at least three of the above-described five algorithms, and 99.7% of the gene sequence variations damaging a protein and the 98.8% of gene sequence variations with less effect of HumDiv were identically detected by at least three of the above-described five algorithms. Further, as a result of drawing an ROC (Receiver Operating Curve) showing accuracy of calculation results of the five algorithms and a combination of the algorithms utilzing the HumDiv and HumVar, it was confirmed that an AUC (Area Under the Receiver Operating Curve) consistency is considerably high (69% to 88.2%). That is, the above-described algorithms are different in calculation method but the calculated gene sequence variation scores are significantly correlated to each other. Therefore, it is included in the scope of the present invention regardless of kinds of algorithms calculating gene sequence variation scores to apply a gene sequence variation score calculated by applying the above-described algorithms or a method employing the algorithms to the steps of calculating an individual protein damage score and an individual drug score according to the present invention.

When a gene sequence variation occurs in an exon region of a gene encoding a protein, the gene sequence variation may directly affect a structure and/or function of the protein. Therefore, the gene sequence variation information may be associated with a degree of damage to a protein function. In this aspect, the method of the present invention calculates an individual protein damage score on the basis of the above-described gene sequence variation score in the following step.

The "protein damage score" used herein refers to a score calculated by summarizing gene sequence variation scores when two or more significant sequence variations are found in a gene region encoding a single protein so that the single protein has two or more gene sequence variation scores. If there is a single significant sequence variation in the gene region encoding the protein, a gene sequence variation score is identical to a protein damage score. Herein, if there are two or more gene sequence variations encoding a protein, a protein damage score is calculated as a mean of gene sequence variation scores calculated for the respective variations. Such a mean can be calculated by, for example, but not limited to, measuring a geometric mean, an arithmetic mean, a harmonic mean, an arithmetic geometric mean, an arithmetic harmonic mean, a geometric harmonic mean, Pythagorean means, an interquartile mean, a quadratic mean, a truncated mean, a Winsorized mean, a weighted mean, a weighted geometric mean, a weighted arithmetic mean, a weighted harmonic mean, a mean of a function, a generalized mean, a generalized f-mean, a percentile, a maximum value, a minimum value, a mode, a median, a mid-range, a central tendency, simple multiplication or weighted multiplication, or by a functional operation of the calculated values.

In an exemplary embodiment of the present invention, the protein damage score is calculated by the following Equation 1. The following Equation 1 can be modified in various ways, and, thus, the present invention is not limited thereto.

$$S_g(v_1, \ldots, v_n) = \left(\frac{1}{n}\sum_{i=1}^{n} v_i^p\right)^{\frac{1}{p}} \qquad \text{[Equation 1]}$$

In Equation 1, $S_g$ is a protein damage score of a protein encoded by a gene g, n is the number of target sequence variations for analysis among sequence variations of the gene g, $v_i$ is a gene sequence variation score of an gene sequence variation, and p is a real number other than 0. In Equation 1, when a value of the p is 1, the protein damage score is an arithmetic mean, if the value of the p is −1, the protein damage score is a harmonic mean, and if the value of the p is close to the limit 0, the protein damage score is a geometric mean.

In another exemplary embodiment of the present invention, the protein damage score is calculated by the following Equation 2.

$$S_g(v_1, \ldots, v_n) = \left(\prod_{i=1}^{n} v_i^{w_i}\right)^{1/\Sigma_{i=1}^{n} w_i} \quad \text{[Equation 2]}$$

In Equation 2, $S_g$ is a protein damage score of a protein encoded by a gene g, n is the number of target sequence variations for analysis among sequence variations of the gene g, $v_i$ is a gene sequence variation score of an ith gene sequence variation, and $w_i$ is a weighting assigned to the $v_i$. If all weightings $w_i$ have the same value, the protein damage score $S_g$ is a geometric mean of the gene sequence variation scores $v_i$. The weighting may be assigned considering a class of the corresponding protein, pharmacodynamic or pharmacokinetic classification of the corresponding protein, pharmacokinetic parameters of the enzyme protein of a corresponding drug, a population group, or a race distribution.

The term "pharmacokinetic parameters of the enzyme protein of a corresponding drug" used herein includes Vmax, Km, Kcat/Km, and the like. Vmax is a maximum enzyme reaction rate when a substrate concentration is very high, and Km is a substrate concentration that causes the reaction to reach ½ Vmax. Km may be regarded as affinity between the corresponding enzyme and the corresponding substrate. As the Km is decreased, a bonding force between the corresponding enzyme and the corresponding substrate is increased. Kcat called the turnover number of an enzyme refers to the number of substrate molecules metabolized for 1 second in each enzyme active site when the enzyme is activated at a maximum rate, and means how fast the enzyme reaction actually occurs.

According to the method of the present invention, an individual drug score is calculated in the following step by associating the above-described protein damage score with a drug-protein relation.

The term "drug score" used herein refers to a value calculated with respect to a predetermined drug by finding out a target protein involved in the pharmacodynamics or pharmacokinetics of the drug, an enzyme protein involved in drug metabolism, a transporter protein, or a carrier protein when the predetermined drug is given, calculating protein damage scores of the proteins, and summarizing the scores.

In the present invention, if two or more proteins involved in the pharmacodynamics or pharmacokinetics of a predetermined drug or drug group are damaged, a drug score is calculated as a mean of the protein damage scores. Such a mean can be calculated by, for example, but not limited to, measuring a geometric mean, an arithmetic mean, a harmonic mean, an arithmetic geometric mean, an arithmetic harmonic mean, a geometric harmonic mean, Pythagorean means, an interquartile mean, a quadratic mean, a truncated mean, a Winsorized mean, a weighted mean, a weighted geometric mean, a weighted arithmetic mean, a weighted harmonic mean, a mean of a function, a generalized mean, a generalized f-mean, a percentile, a maximum value, a minimum value, a mode, a median, a mid-range, a central tendency, simple multiplication or weighted multiplication, or by a functional operation of the calculated values.

The drug score may be calculated by adjusting weightings of a target protein involved in the pharmacodynamics or pharmacokinetics of the corresponding drug, an enzyme protein involved in drug metabolism, a transporter protein, or a carrier protein in consideration of pharmacological characteristics, and the weighting may be assigned considering pharmacokinetic parameters of the enzyme protein of a corresponding drug, a population group, a race distribution, or the like. Further, although not directly interacting with the corresponding drug, proteins interacting with a precursor of the corresponding drug and metabolic products of the corresponding drug, for example, proteins involved in a pharmacological pathway, may be considered, and protein damage scores thereof may be combined to calculate the drug score. Further, protein damage scores of proteins significantly interacting with the proteins involved in the pharmacodynamics or pharmacokinetics of the corresponding drug may also be considered and combined to calculate the drug score. Information about proteins involved in a pharmacological pathway of the corresponding drug, significantly interacting with the proteins in the pathway, or involved in a signal transduction pathway thereof can be searched in publicly known biological databases such as PharmGKB (Whirl-Carrillo et al., Clinical Pharmacology & Therapeutics 2012; 92(4):414-4171), The MIPS Mammalian Protein-Protein Interaction Database (Pagel et al., Bioinformatics 2005; 21(6):832-834), BIND (Bader et al., Biomolecular Interaction Network Database, Nucleic Acids Res. 2003 Jan. 1; 31(1):248-50), Reactome (Joshi-Tope et al., Nucleic Acids Res. 2005 Jan. 1; 33(Database issue):D428-32), and the like.

In an exemplary embodiment of the present invention, the drug score is calculated by the following Equation 3. The following Equation 3 can be modified in various ways, and, thus, the present invention is not limited thereto.

$$S_d(g_1, \ldots, g_n) = \left(\frac{1}{n}\sum_{i=1}^{n} g_i^p\right)^{\frac{1}{p}} \quad \text{[Equation 3]}$$

In Equation 3, $S_d$ is a drug score of a drug d, n is the number of proteins directly involved in the pharmacodynamics or pharmacokinetics of the drug d or interacting with a precursor of the corresponding drug or metabolic products of the corresponding drug, for example, proteins encoded by one or more genes selected from a gene group involved in a pharmacological pathway, $g_i$ is a protein damage score of a protein directly involved in the pharmacodynamics or pharmacokinetics of the drug d or interacting with a precursor of the corresponding drug or metabolic products of the corresponding drug, for example, a protein encoded by one or more genes selected from a gene group involved in a pharmacological pathway, and p is a real number other than 0. In Equation 3, when a value of the p is 1, the drug score is an arithmetic mean, if the value of the p is −1, the drug score is a harmonic mean, and if the value of the p is close to the limit 0, the drug score is a geometric mean.

In yet another exemplary embodiment of the present invention, the drug score is calculated by the following Equation 4.

$$S_d(g_1, \ldots, g_n) = \left(\prod_{i=1}^{n} g_i^{w_i}\right)^{1/\Sigma_{i=1}^{n} w_i} \quad \text{[Equation 4]}$$

In Equation 4, $S_d$ is a drug score of a drug d, n is the number of proteins directly involved in the pharmacodynamics or pharmacokinetics of the drug d or interacting with a precursor of the corresponding drug or metabolic products of the corresponding drug, for example, proteins encoded by one or more genes selected from a gene group involved in a pharmacological pathway, $g_i$ is a protein damage score of a protein directly involved in the pharmacodynamics or pharmacokinetics of the drug d or interacting with a precursor of the corresponding drug or metabolic products of the corresponding drug, for example, a protein encoded by one or more genes selected from a gene group involved in a pharmacological pathway, and $w_i$ is a weighting assigned to the $g_i$. If all weightings $w_i$ have the same value, the drug score $S_d$ is a geometric mean of the protein damage scores $g_i$. The weighting may be assigned considering a kind of the protein, pharmacodynamic or pharmacokinetic classification of the protein, pharmacokinetic parameters of the enzyme protein of a corresponding drug, a population group, or a race distribution.

In the case of a geometric mean calculation method used in an exemplary embodiment of the present invention, weightings are equally assigned regardless of a characteristic of a drug-protein relation. However, it is possible to calculate a drug score by assigning weightings considering each characteristic of a drug-protein relation as described in yet another exemplary embodiment. For example, different scores may be assigned to a target protein of a drug and a transporter protein related to the drug. Further, it is possible to calculate a drug score by assigning pharmacokinetic parameters Km, Vmax, and Kcat/Km as weightings to the enzyme protein of a corresponding drug. Furthermore, for example, since a target protein is regarded more important than a transporter protein in terms of pharmacological action, it may be assigned a higher weighting, or a transporter protein or a carrier protein may be assigned high weightings with respect to a drug whose effectiveness is sensitive to a concentration, but the present invention is not limited thereto. The weighting may be minutely adjusted according to characteristics of a relation between a drug and a protein related to the drug and characteristics of an interaction between the drug and the protein. A sophisticated algorithm configured to assign a weighting of a characteristic of an interaction between a drug and a protein can be use, for example, a target protein and a transporter protein may be assigned 2 points and 1 point, respectively.

In the above description, only the protein directly interacting with a drug has been exemplified. However, as described in an exemplary embodiment of the present invention, the predictive ability of the above Equation can be improved by using information about the protein interacting with a precursor of the corresponding drug or metabolic products of the corresponding drug, the protein significantly interacting with proteins involved in the pharmacodynamics or pharmacokinetics of the corresponding drug, and the protein involved in a signal transduction pathway thereof. That is, by using information about a protein-protein interaction network or pharmacological pathway, it is possible to use information about various proteins relevant thereto. That is, even if a significant variation is not found in the protein directly interacting with the drug so that there is no protein damage score calculated with respect to the protein or there is no damage (for example, 1.0 point when a SIFT algorithm is applied), a mean (for example, a geometric mean) of protein damage scores of proteins interacting with the protein or involved in the same signal transduction pathway of the protein may be used as a protein damage score of the protein so as to be used for calculating a drug score.

The individual drug score can be calculated with respect to all drugs from which information about one or more associated proteins can be acquired or some drugs selected from the drugs. Further, the individual drug score can be converted into a rank.

The method of the present invention may further include: determining the order of priority among drugs applicable to an individual by using the above-described individual drug score; or determining whether or not to use the drugs applicable to the individual by using the above-described individual drug score.

Although the individual drug score can be applied to each of all drugs, it can be more useful when applied to drugs classified by disease, clinical characteristic or activity, or medically comparable drugs. The drug classification system which can be used in the present invention may include, for example, ATC (Anatomical Therapeutic Chemical Classification System) codes, top 15 frequently prescribed drug classes during 2005 to 2008 in the United States (Health, United States, 2011, Centers for Disease Control and Prevention), a list of drugs with known pharmacogenomical markers which can influence the drug effect information described in the drug label, or a list of drugs withdrawn from the market due to side effects thereof.

The method of the present invention may further include calculating a prescription score.

The term "prescription score" used herein refers to a score calculated by summarizing the drug scores determined with respect to drugs, respectively, when two or more drugs are administered at the same time or at a short distance of time sufficient to significantly affect pharmacological actions thereof. In the present invention, when two or more drugs are determined on the basis of the order of priority among drugs and need to be administered at the same time, the prescription score may be calculated by summarizing drug scores determined with respect to the respective drugs. For example, if there is no protein commonly interacting with the drugs, the prescription score may be calculated by simply averaging, or summing up or multiplying drug scores of the drugs. If there is a protein commonly interacting with the drugs, the prescription score may be calculated by assigning, for example, a double weighting to a protein damage score of the corresponding commonly interacting protein to calculate drug scores of the respective drugs and then summing up the corresponding drug scores.

The prescription score is provided to determine appropriateness or risk of the drugs included in a prescription applied to an individual over the effects of the respective drugs. In this aspect, the method of the present invention may further include determining appropriateness or risk of a prescription applied to an individual.

The invention of the present invention may be performed for the purpose of preventing side effects of a drug, but is not limited thereto.

FIG. 1 is a flowchart illustrating each step of a method for providing information for personalizing drug selection using individual genome sequence variations according to an exemplary embodiment of the present invention. In an exemplary embodiment of the present invention, the method for providing information for personalizing drug selection is performed by sequentially (1) inputting or receiving genome sequence information of an individual user (S100), (2) inputting or receiving information relevant to a predetermined drug or drug group (S110), (3) determining genome sequence variation information of the individual user (S120), (4) calculating an individual protein damage score with respect to the predetermined drug or drug group (S130), (5) calculating an individual drug score with respect to the predetermined drug or drug group (S140), (6) marking the drug score and sort drugs by ranking or determining the order of priority among drugs according to drug score rankings (S150), and (7) selecting a drug in consideration of the drug score and the priority and calculating a prescription score (S160).

Figure 3:
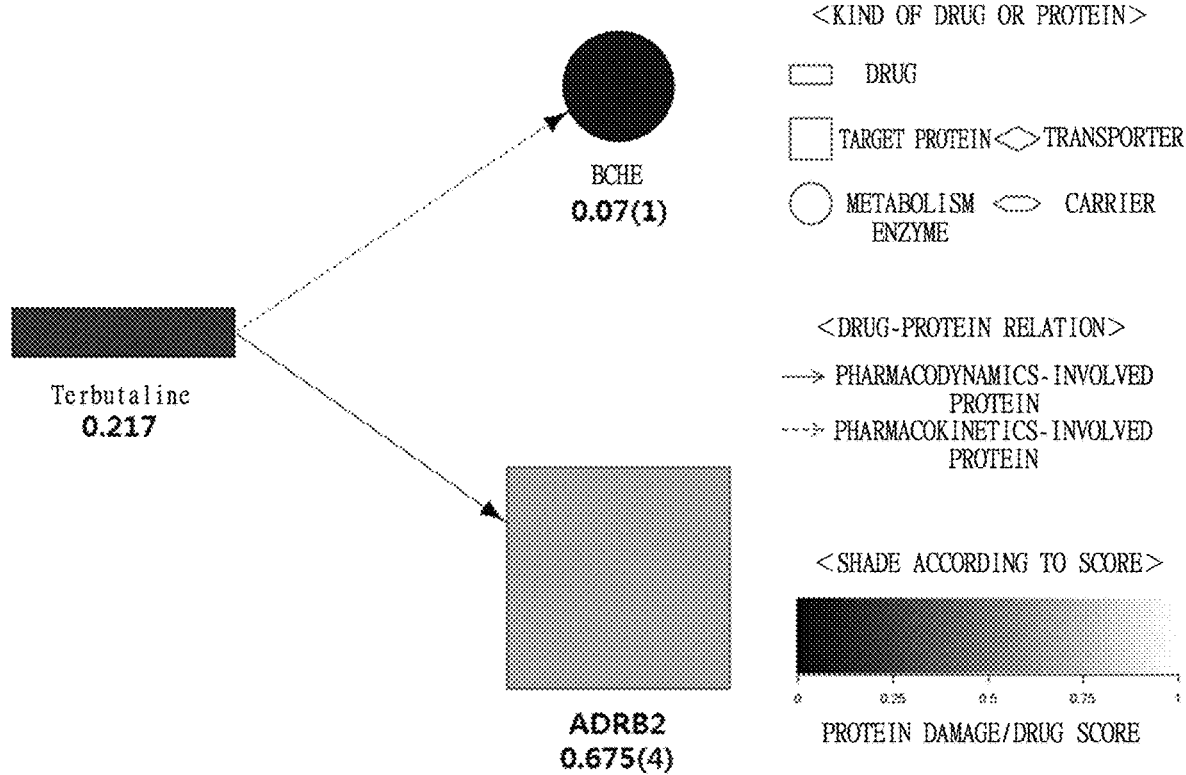
FIG. 3 is a diagram illustrating the number of gene variations for each protein, a protein damage score, and a drug score of a corresponding individual as calculated with respect to a drug Terbutaline, by using a method according to the present invention on the basis of individual genome sequence variation information.

If a drug score sorted by ranking as described above is selected, the method of the present invention may further include assisting a doctor in charge of prescription in making a decision by providing a pharmacogenomic calculation process and a ground for calculating the drug score as information in the form of a diagram, a chart, explanation, and the like. That is, the invention according to the present invention may further include providing one or more information among gene sequence variation information, a gene sequence variation score, a protein damage score, a drug score, and information used for calculation thereof, which are grounds for determining the order of priority among drugs of the present invention. For example, as illustrated in FIG. 3, when a user selects a specific drug Terbutaline, it is possible to provide a diagram, a chart, explanation, and the like, regarding pharmacogenomil grounds for calculating a drug score of the corresponding drug.

In another aspect, the present invention relates to a system for personalizing drug selection using individual genome sequence variations, the system including: a database from which information relevant to a gene or protein related to a drug or drug group applicable to an individual can be searched or extracted; a communication unit accessible to the database; a first calculation module configured to calculate one or more gene sequence variation information involved in the pharmacodynamics or pharmacokinetics of the drug or drug group on the basis of the information; a second calculation module configured to calculate an individual protein damage score by using the gene sequence variation information; a third calculation module configured to calculate an individual drug score by associating the individual protein damage score with a drug-protein relation; and a display unit configured to display the values calculated by the calculation modules.

In the present invention, a module may represent a functional or structural combination of hardware for implementing the technical spirit of the present invention and software for driving the hardware. For example, the module may be a predetermined code and a logical unit of a hardware resource by which the predetermined code is executed. It is obvious to those skilled in the art that the module does not necessarily mean physically connected codes or one kind of hardware.

The term "calculation module" used herein may represent a predetermined code and a logical unit of a hardware resource by which the predetermined code is executed for calculating each score on the basis of the gene sequence variation score, protein damage score, drug score, and information as grounds for calculation thereof with respect to a drug and a gene of analysis target according to the present invention, but does not necessarily mean physically connected codes or one kind of hardware.

The system according to the present invention may further include a fourth calculation module configured to calculate the order of priority among drugs applicable to the individual by using the individual drug score calculated by the third calculation module; or determine whether or not to use the drugs applicable to the individual by using the above-described individual drug score.

The system according to the present invention may further include a fifth calculation module configured to calculate a prescription score by summarizing drug scores determined with respect to respective drugs if two or more drugs are determined on the basis of the order of priority among drugs and need to be administered at the same time.

The system according to the present invention may further include a user interface configured to input a list of drugs or drug groups by the user, or access a database including information about a drug or drug group effective in treating a specific disease and extract relevant information, and thereby calculate and provide a drug score of the drug.

The system according to the present invention may further include a display unit configured to display the values calculated by the respective calculation modules or a calculation process for determining the order of priority among drugs and information as a ground for the calculation or determination.

In the system according to the present invention, the database or a server including access information, the calculated information, and the user interface connected thereto may be used as being linked to one another.

If new pharmacological/biochemical information regarding a drug-protein relation is produced, the system according to the present invention is immediately updated so as to be used for further improved personalization of drug selection. In an exemplary embodiment of the present invention, when the database or knowledge base is updated, the gene sequence variation information, gene sequence variation score, protein damage score, drug score, and the information as grounds for the calculation thereof stored in the respective calculation modules are updated.

Figure 2:
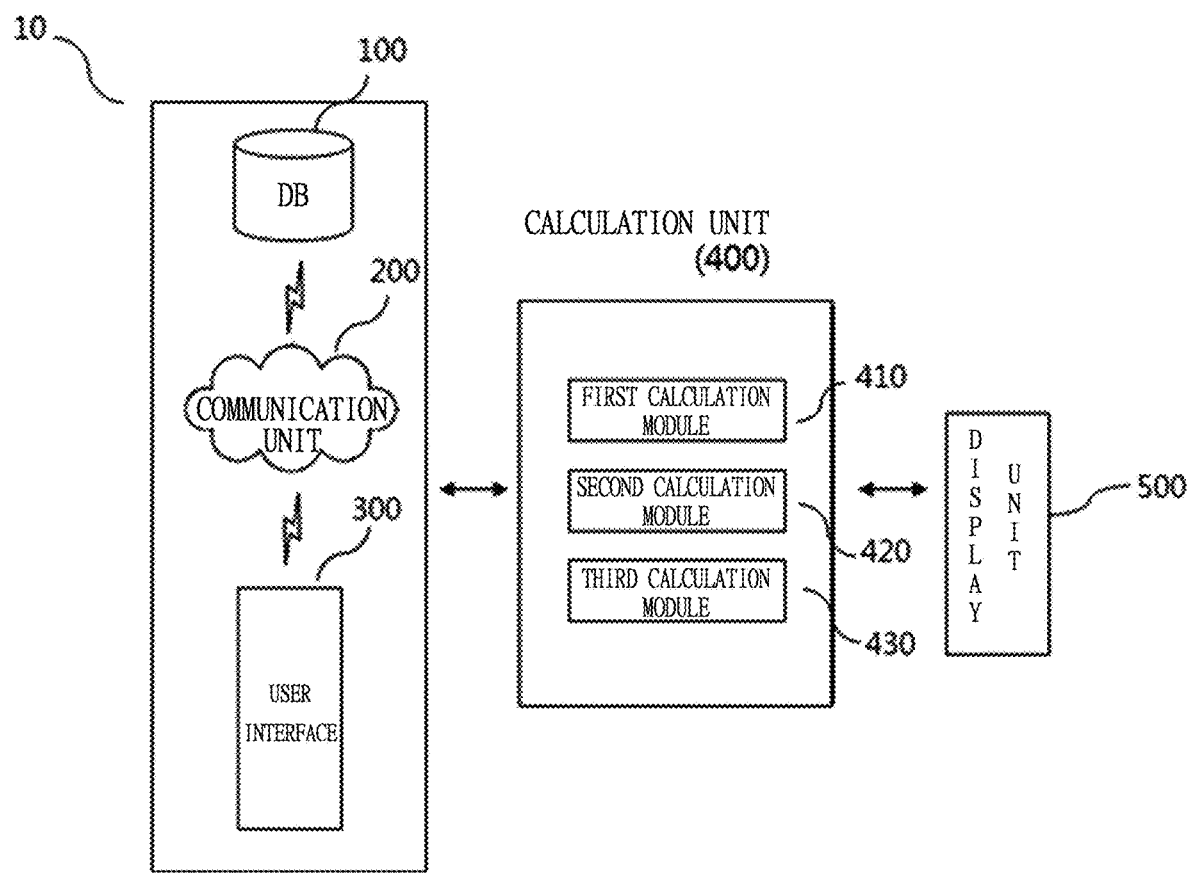
FIG. 2 is a schematic configuration view of a system for personalizing drug selection using individual genome sequence variations according to an exemplary embodiment of the present invention (DB: Database).

FIG. 2 is a schematic configuration view of a system for personalizing drug selection using individual genome sequence variations according to an exemplary embodiment of the present invention. A system 10 of the present invention may include a database (DB) 100 from which information relevant to a gene or protein related to a drug or drug group can be searched or extracted, a communication unit 200, a user interface or terminal 300, a calculation unit 400, and a display unit 500.

In the system according to the present invention, the user interface or terminal 300 may be configured to request a processing for personalizing drug selection using individual genome sequence variations to a server and receive a result from a server and/or store it. And the user interface or terminal 300 may consists of a terminal, such as a smart phone, a PC (Personal Computer), a tablet PC, a personal digital assistant (PDA), and a web pad, which includes a memory means and has a mobile communication function with a calculation ability using a microprocessor.

In the system according to the present invention, the server is a means for providing an access to the database 100 with respect to a drug, a gene variation, or a drug-protein relation and is connected to the user interface or terminal 300 through the communication unit 200 so as to exchange various kinds of information. Herein, the communication unit 200 may include not only communication in the same hardware but also a local area network (LAN), a metropolitan area network (MAN), a wide area network (WAN), the Internet, 2G, 3G and 4G mobile communication networks, Wi-Fi, Wibro, and the like, and may use any communication method regardless of whether it is wired or wireless. The database 100 may be directly installed in the server and may also be connected to various life science databases accessible via the Internet depending on a purpose.

In the system according to the present invention, the calculation unit 400 may include a first calculation module 410 configured to calculate one or more gene sequence variation information involved in the pharmacodynamics or pharmacokinetics of the drug or drug group using the collected/inputted information, a second calculation module 420 configured to calculate an individual protein damage score, and a third calculation module 430 configured to calculate an individual drug score, as described above.

The method according to the present invention can be implemented by hardware, firmware, software, or combinations thereof. If the method is implemented by software, a storage medium may include any storage or transmission medium readable by a device such as a computer. For example, the computer-readable medium may include a ROM (read only memory); a RAM (random access memory); a magnetic disc storage medium; an optical storage medium; a flash memory device; and other electric, optical or acoustic signal transmission medium.

In this aspect, the present invention provides a computer-readable medium including an execution module for executing a processor that performs an operation including: acquiring gene sequence variation information involved in the pharmacodynamics or pharmacokinetics of a predetermined drug or drug group from individual genome sequence information; calculating an individual protein damage score by using the gene sequence variation information; and associating the individual protein damage score with a drug-protein relation to thereby calculate an individual drug score.

The processor may further include: determining the order of priority among drugs applicable to an individual by using the above-described individual drug score; or determining whether or not to use the drugs applicable to the individual by using the above-described individual drug score.

Hereinafter, the present invention will be described in more detail with reference to the following Examples. The following Examples are provided to explain the present invention in detail but do not limit the scope of the present invention.

The following Examples are divided as follows.

First group: Examples show actual cases of the present invention, and illustrate a process of providing a method for personalizing drug selection of the present invention with a selected one drug (Example 1), two drugs in need of selection (Example 2), or various comparable drugs belonging to the same drug group which can be used in a specific medical condition (Example 3).

Second group: Examples are provided to demonstrate validity of the present invention, and include demonstration of data-based validity on the basis of disclosed large-scale individual genome sequence variation information (Example 4), individual genome sequence analysis on 12 pediatric leukemia patients showing warning signs of serious side effects during a treatment with Busulfan as an anticancer drug and bone-marrow inhibitor and demonstration of actual clinical validity on the basis of the analysis (Example 5), and demonstration of the validity in a view of population genetics for suggesting that the method for personalizing drug selection of the present invention can be used for individual personalized prevention of drug side effects by showing a high correlation between an individual drug score calculated according to the present invention and the drug's withdrawal from the market and restriction to use (Example 6).

Third group: Example shows various application cases of the present invention, and suggests usefulness of a method for personalizing drug selection of the present invention by contemplating a clinical significance of individual genome sequence variations found in a target protein of a specific drug with a predicted risk for an individual (Example 7).

Example 1. Providing Method for Personalizing Drug Selection with Respect to Selected One Drug (Terbutaline)

In order to provide a method for personalizing drug selection with respect to Terbutaline as one of drugs used for treating asthma, the following analysis was conducted using the method and the system of the present invention.

To be more specific, a gene sequence analysis was conducted on an individual sg01 which was healthy but determined as having a high medical risk of getting asthma since his/her mother was undergoing treatment for asthma. Gene sequence variation scores of BCHE (butyrylcholinesterase) and ADRB2 (adrenoceptor beta 2, surface) known as genes involved in the pharmacodynamics or pharmacokinetics of Terbutaline were calculated for each variant by using a SIFT algorithm, and protein damage scores and drug scores were calculated. The results thereof were as listed in Table 16 and illustrated in FIG. 3.

TABLE 16

| Drug name (Drug score) | Gene/protein | Protein damage score | Protein group | Variation score | Variation information Chromosomal location | Reference genotype | Variant genotype |
|---|---|---|---|---|---|---|---|
| Terbutaline (0.22) | Adrenoceptor beta 2, surface (ADRB2) | 0.68 | Target (PD) | 0.46 | chr5: 148206440 | G | A |
| | | | | 0.45 | chr5: 148206473 | G | C |
| | | | | 1.00 | chr5: 148207447 | G | C |
| | | | | 1.00 | chr5: 148207633 | G | A |
| | Butyrylcholinesterase (BCHE) | 0.07 | Enzyme (PK) | 0.07 | chr3: 165491280 | C | T |

As listed in Table 16, according to the result of the gene sequence analysis on the individual sg01, a gene sequence variation score of a single variant (chr3:165491280) found in BCHE was 0.07, and gene sequence variation scores of four variants (chr5:148206440, chr5:148206473, chr5:148207447, chr5:148207633) found in ADRB2 were 0.46, 0.45, 1, and 1, respectively. Based on the gene sequence variation scores, individual protein damage scores with respect to BCHE and ADRB2 were calculated using Equation 2; and the results were 0.07 and 0.68 (=$(0.46 \times 0.45 \times 1 \times 1)^{1/4}$), respectively. Based on the protein damage scores, an individual drug score with respect to Terbutaline was calculated using Equation 4, and the result was 0.22 (=$(0.07 \times 0.68)^{1/2}$).

By the method according to the present invention, it was observed that the individual sg01 had moderate (protein damage score: 0.68) to severe (protein damage score: 0.07) damage with respect to ADRB2 and BCHE as representative target protein and enzyme protein, respectively, of Terbutaline, and overall, the individual drug score of the individual sg01 with respect to Terbutaline was at a severe level (0.22) (FIG. 3). Therefore, it was determined that it was preferable to recommend avoiding prescription of Terbutaline with a low drug score of 0.22 to the individual sg01 and substituting Terbutaline with another drug.

Example 2. Providing Method for Personalizing Drug Selection with Respect to Two Drugs (Aspirin and Tylenol) in Need of Selection In order to provide a method for personalizing drug selection with respect to Aspirin and Tylenol as drugs used for treating pain, the following analysis was conducted using the method and the system of the present invention.

Both of Aspirin (Acetylsalicylic acid) and Tylenol (Acetaminophen) have been widely used as painkillers, but show individual differences in responsiveness and sometimes cause severe side effects. In particular, it has been impossible to predict which of two drugs would provide a better medicinal effect or cause a more severe adverse drug reaction. Therefore, hereinafter, it will be described that the method and the system of the present invention can be used to help in making a difficult determination, which frequently occurs in clinical practice.

A gene sequence analysis was conducted on an individual sg09 which had felt discomfort when taking an antipyretics and a pain killer commercially available without a prescription and thus took half the recommended dose thereof. Gene sequence variation score of genes involved in the pharmacodynamics or pharmacokinetics of Aspirin and Tylenol, protein damage scores, and drug scores were calculated. The results thereof were as listed in Table 17, Table 18, and illustrated in FIG. 4.

TABLE 17

| Drug name (Drug score) | Gene/protein | Protein damage score | Protein group | Variation score | Chromosomal location | Reference genotype | Variant genotype |
|---|---|---|---|---|---|---|---|
| Acetylsalicylic acid (0.76) | Aldo-keto reductase family 1, member C1 (AKR1C1) | 1.00 | Target (PD) | 1.00 | chr10: 5010572 | A | G |
| | Cyclooxygenase 1 (PTGS1) | 0.38 | Target (PD) | 0.38 | chr9: 125133479 | T | C |
| | Cyclooxygenase 2 (PTGS2) | 1.00 | Target (PD) | | | | |
| | Cytochrome P450 2C19 (CYP2C19) | 1.00 | Enzyme (PK) | 1.00 | chr10: 96602622 | C | T |
| | Cytochrome P450 2C8 (CYP2C8) | 1.00 | Enzyme (PK) | 1.00 | chr10: 96827178 | T | C |
| | Cytochrome P450 2C9 (CYP2C9) | 1.00 | Enzyme (PK) | | | | |
| | ATP-binding cassette, sub-family B, member 1 (ABCB1) | 1.00 | Transporter (PK) | 1.00<br>1.00 | chr7: 87138645<br>chr7: 87179601 | A<br>A | G<br>G |
| | Solute carrier family 16, member 1 (SLC16A1) | 1.00 | Transporter (PK) | 1.00 | chr1: 113456546 | A | T |
| | Solute carrier family 22, member 10 (SLC22A10) | 0.17 | Transporter (PK) | 1.00<br>0.03 | chr11: 63066500<br>chr11: 63072226 | A<br>C | G<br>A |
| | Solute carrier family 22, member 11 (SLC22A11) | 1.00 | Transporter (PK) | | | | |
| | Solute carrier family 22, member 6 (SLC22A6) | 1.00 | Transporter (PK) | | | | |
| | Solute carrier family 22, member 7 (SLC22A7) | 0.89 | Transporter (PK) | 1.00<br>0.79 | chr6: 43270097<br>chr6: 43270151 | T<br>C | C<br>T |
| | Solute carrier family 22, member 8 (SLC22A8) | 0.32 | Transporter (PK) | 0.32 | chr11: 62766431 | A | T |

TABLE 17-continued

| Drug name (Drug score) | Gene/protein | Protein damage score | Protein group | Variation score | Chromosomal location | Reference genotype | Variant genotype |
|---|---|---|---|---|---|---|---|
| | Solute carrier organic anion transporter family, member 2B1 (SLCO2B1) | 0.84 | Transporter (PK) | 1.00<br>0.71 | chr11: 74904362<br>chr11: 74907582 | T<br>C | C<br>T |
| | Albumin (ALB) | 1.00 | Carrier (PK) | 1.00 | chr4: 74285239 | C | T |

TABLE 18

| Drug name (Drug score) | Gene/protein | Protein damage score | Protein group | Variation score | Chromosomal location | Reference genotype | Variant genotype |
|---|---|---|---|---|---|---|---|
| Acetaminophen (0.31) | Cyclooxygenase 1 (PTGS1) | 0.38 | Target (PD) | 0.38 | chr9: 125133479 | T | C |
| | Cyclooxygenase 2 (PTGS2) | 1.00 | Target (PD) | | | | |
| | Cytochrome P450 1A1 (CYP1A1) | $2.8 \times 10^{-5}$ | Enzyme (PK) | 0.08<br>$1 \times 10^{-8}$ | chr15: 75015305<br>chr15: 75015215 | C<br>T | T<br>G |
| | Cytochrome P450 1A2 (CYP1A2) | 1.00 | Enzyme (PK) | | | | |
| | Cytochrome P450 2A6 (CYP2A6) | 0.52 | Enzyme (PK) | 0.55<br>0.49 | chr19: 41350664<br>chr19: 41356281 | A<br>T | T<br>C |
| | Cytochrome P450 2C8 (CYP2C8) | 1.00 | Enzyme (PK) | 1.00 | chr10: 96827178 | T | C |
| | Cytochrome P450 2C9 (CYP2C9) | 1.00 | Enzyme (PK) | | | | |
| | Cytochrome P450 2D6 (CYP2D6) | 0.20 | Enzyme (PK) | 0.98<br>0.39<br>0.02 | chr22: 42525182<br>chr22: 42525756<br>chr22: 42526694 | A<br>G<br>G | T<br>A<br>A |
| | Cytochrome P450 2E1 (CYP2E1) | 0.76 | Enzyme (PK) | 0.57<br>1.00 | chr10: 135347397<br>chr10: 135351362 | T<br>T | C<br>C |
| | Cytochrome P450 3A4 (CYP3A4) | 1.00 | Enzyme (PK) | | | | |
| | ATP-binding cassette, sub-family B, member 1 (ABCB1) | 1.00 | Transporter (PK) | 1.00<br>1.00 | chr7: 87138645<br>chr7: 87179601 | A<br>A | G<br>G |
| | Solute carrier family 22, member 6 (SLC22A6) | 1.00 | Transporter (PK) | | | | |

As listed in Table 17, by using gene sequence variation information of sg09 involved in the pharmacodynamics or pharmacokinetics of a total of 15 proteins, including 3 target proteins, 3 enzyme proteins, 8 transporter proteins, and 1 carrier protein, of Aspirin (Acetylsalicylic acid), an individual drug score was obtained. Firstly, gene sequence variation information of a gene involved in the pharmacodynamics or pharmacokinetics of Aspirin was determined, and a gene sequence variation score was calculated by using a SIFT algorithm. Since each of PTGS1 as a target protein of Aspirin and SLC22A8 as a transporter protein had a single variant (chr9:125133479 and chr11:62766431, respectively), gene sequence variation scores (0.38, 0.32, respectively) were determined as protein damage scores. Since SLC22A10 as another transporter protein had two variants (chr11:63066500, chr11: 63072226), gene sequence variation scores of the respective variants were calculated as 1.0 and 0.03, respectively, and a protein damage score was calculated using Equation 2 $(0.17=(1.0\times0.03)^{1/2})$. After summarization of a total of 15 protein damage scores including the above-described three protein damage scores, a drug score was calculated using Equation 4. As a result, it was confirmed that the drug score of the individual sg09 with respect to Aspirin was 0.76 $(=(1.0\times0.38\times1.0\times1.0\times1.0\times 1.0\times1.0\times1.0\times0.17\times1.0\times1.0\times0.89\times0.32\times0.84\times1.0)^{1/15})$ Further, as listed in Table 18, by using gene sequence variation information of sg09 involved in the pharmacodynamics or pharmacokinetics of a total of 12 proteins, including 2 target proteins, 8 enzyme proteins, and 2 transporter proteins of Tylenol (Acetaminophen), an individual drug score was obtained. Firstly, gene sequence variation information of a gene involved in the pharmacodynamics or pharmacokinetics of Tylenol was determined, and a gene sequence variation score was calculated by using a SIFT algorithm. Since PTGS1 as a target protein of Tylenol had a single variant (chr9:125133479), a gene sequence variation score was determined as a protein damage score. Further, with respect to CYP1A1 (chr15:75015305, chr15:75015215) and CYP2A6 (chr19:41350664, chr19:41356281) as the enzyme proteins having two variants and CYP2D6 (chr22:42525182, chr22:42525756, chr22:42526694) as the enzyme protein having three variants, protein damage scores were calculated as $2.8 \times 10^{-5}$ ($=(0.08 \times (1 \times 10-8))^{1/2}$), 0.52 ($=(0.55 \times 0.49)^{1/2}$), and 0.2 ($=(0.98 \times 0.39 \times 0.02)^{1/3}$), respectively, by obtaining a geometric mean (using Equation 2) of gene sequence variation scores. After summarization of a total of 12 protein damage scores including the above-described four protein damage scores, a drug score was calculated using a geometric mean (using Equation 4). As a result, it was confirmed that the drug score of the individual sg09 with respect to Tylenol was 0.31 ($=(0.38 \times 1.0 \times (2.8 \times 10^{-5}) \times 1.0 \times 0.52 \times 1.0 \times 1.0 \times 0.2 \times 0.76 \times 1.0 \times 1.0 \times 1.0)^{1/12}$).

Figure 4:
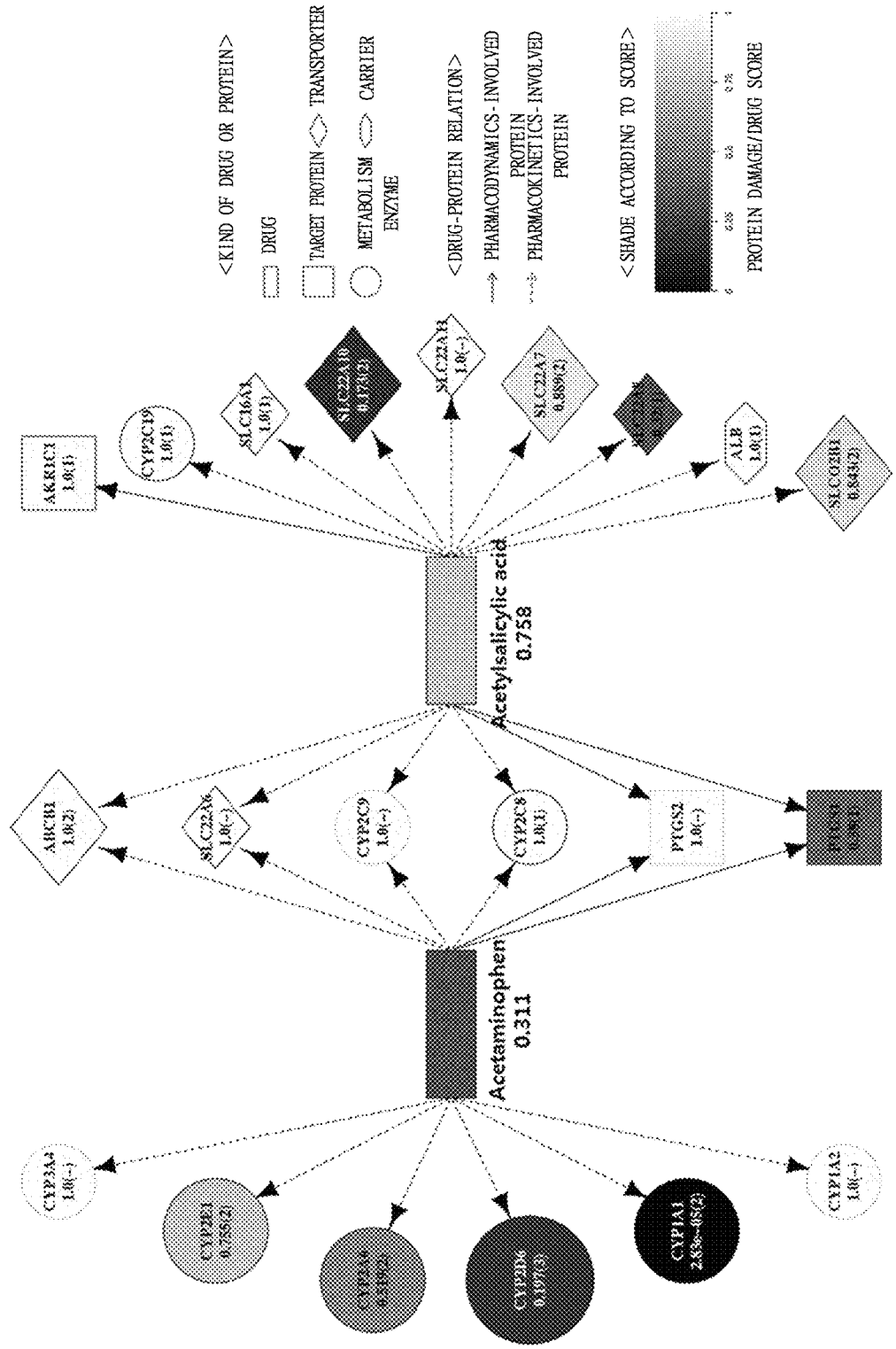
FIG. 4 is a diagram illustrating the number of gene variations for each protein, a protein damage score, and a drug score of a corresponding individual as calculated with respect to a plurality of drugs (Aspirin (acetylsalicylic acid) and Tylenol (acetaminophen)) as comparison targets, by using a method according to the present invention on the basis of individual genome sequence variation information.

Further, as illustrated in FIG. 4, the combined individual drug score of the individual sg09 with respect to Aspirin was calculated as 0.76, which was higher than the individual drug score of 0.31 with respect to Tylenol. Therefore, it was determined that it was preferable to recommend selecting Aspirin to the individual sg09 in order to reduce discomfort caused by a drug when clinically selecting one of Aspirin and Tylenol unless there is a particular reason to the contrary.

Example 3. Providing Method for Personalizing Drug Selection to Assist in Selecting Highly Safe Drug Among Various Comparable Drugs Belonging to Same Drug Group (Same ATC Code Group)

In order to provide a method for personalizing drug selection to assist in selecting a drug with high safety among various comparable drugs belonging to the same drug group (same ATC code group), the following experiment was conducted using the method and the system of the present invention.

Among 22 drugs belonging to C07 beta blockers according to the internally certified ATC code, 11 drugs are specific beta blockers [C07AB], 9 drugs are non-specific beta blockers [C07AA], and two drugs are alpha and beta blockers [C07AG]. For individual genome sequence variation analysis on 14 individuals (sg01, sg02, sg03, sg04, sg05, sg07, sg09, sg11, sg12, sg13, sg14, sg16, sg17, sg19), HISEQ-2000 as an NGS (Next Generation Sequencing) device manufactured by Illumina was used to conduct a 30× whole genome sequencing. In this case, alternatively, a whole exome sequencing (WES) as a part of the whole genome sequencing or a targeted exome sequencing with respect to main 500 to 1000 genes relevant to 500 to 1000 drug may be conducted. The sequenced sequence fragments underwent data cleaning and quality check and outputted in the form of SAM (Sequence Alignment Map) and BAM (Binary Alignment Map) files aligned with a human reference group sequence (for example, HG19). The cleaned alignment result was outputted in the form of VCF (Variation Calling Format) file while detecting variations such as single nucleotide variations (SNVs) and Indels by using software tools such as SAMTools:pileup, SAMTools:mpileup, GATK:recalibration, GATK:realignment, and the like.

After the VCF file including the gene sequence variation information was inputted and the above-described gene sequence variation score $v_i$ was calculated for each variant, an individual protein damage score Sg was calculated using Equation 2. Then, an individual drug score $S_d$ was calculated using Equation 4. Then, a profile of drug scores and a profile of the order of priority of drugs were calculated, respectively. The results thereof were as listed in Table 19 and illustrated in FIG. 5.

TABLE 19

| Drug name | sg01 | sg02 | sg03 | sg04 | sg05 | sg07 | sg09 | sg11 | sg12 | sg13 | sg14 | sg16 | sg17 | sg19 |
|---|---|---|---|---|---|---|---|---|---|---|---|---|---|---|
| Alprenolol | 0.53 | 0.64 | 0.60 | 0.60 | 0.54 | 0.71 | 0.51 | 0.65 | 1.00 | 1.00 | 0.69 | 0.81 | 0.82 | 0.59 |
| Bopindolol | 0.87 | 0.85 | 0.97 | 0.97 | 0.72 | 0.95 | 0.71 | 0.87 | 1.00 | 1.00 | 1.00 | 0.81 | 0.82 | 0.85 |
| Bupranolol | 0.88 | 0.77 | 0.95 | 0.95 | 0.68 | 0.92 | 0.57 | 0.79 | 1.00 | 1.00 | 1.00 | 0.70 | 0.72 | 0.77 |
| Carteolol | 0.49 | 0.57 | 0.52 | 0.52 | 0.52 | 0.65 | 0.44 | 0.59 | 1.00 | 1.00 | 0.63 | 0.76 | 0.78 | 0.52 |
| Nadolol | 0.91 | 0.61 | 0.96 | 0.96 | 0.74 | 0.94 | 0.65 | 0.84 | 1.00 | 1.00 | 1.00 | 0.76 | 0.74 | 0.82 |
| Oxprenolol | 0.49 | 0.55 | 0.47 | 0.47 | 0.47 | 0.56 | 0.41 | 0.56 | 0.79 | 1.00 | 0.55 | 0.69 | 0.65 | 0.47 |
| Penbutolol | 0.80 | 0.82 | 0.96 | 0.96 | 0.74 | 0.94 | 0.65 | 0.84 | 1.00 | 1.00 | 1.00 | 0.76 | 0.78 | 0.82 |
| Pindolol | 0.57 | 0.65 | 0.59 | 0.59 | 0.54 | 0.66 | 0.53 | 0.66 | 0.85 | 1.00 | 0.65 | 0.77 | 0.74 | 0.58 |
| Propranolol | 0.49 | 0.49 | 0.64 | 0.05 | 0.53 | 0.53 | 0.33 | 0.72 | 0.77 | 1.00 | 0.57 | 0.66 | 0.51 | 0.54 |
| Sotalol | 0.88 | 0.77 | 0.95 | 0.95 | 0.68 | 0.92 | 0.57 | 0.79 | 1.00 | 1.00 | 1.00 | 0.70 | 0.72 | 0.77 |
| Timolol | 0.67 | 0.62 | 0.69 | 0.69 | 0.69 | 0.78 | 0.62 | 0.74 | 1.00 | 1.00 | 0.77 | 0.86 | 0.84 | 0.69 |
| Acebutolol | 0.54 | 0.31 | 0.57 | 0.57 | 0.45 | 0.50 | 0.49 | 0.67 | 0.71 | 0.40 | 0.66 | 0.57 | 0.74 | 0.56 |
| Atenolol | 1.00 | 0.72 | 0.95 | 0.90 | 0.77 | 0.94 | 0.43 | 1.00 | 0.79 | 0.95 | 0.87 | 0.40 | 0.80 | 0.95 |
| Betaxolol | 0.49 | 0.57 | 0.39 | 0.01 | 0.52 | 0.49 | 0.44 | 0.49 | 1.00 | 1.00 | 0.63 | 0.76 | 0.58 | 0.52 |
| Bevantolol | 0.71 | 0.85 | 0.74 | 0.74 | 0.78 | 0.73 | 0.55 | 0.73 | 0.99 | 1.00 | 0.99 | 0.79 | 0.81 | 0.84 |
| Bisoprolol | 0.49 | 0.57 | 0.52 | 0.52 | 0.52 | 0.65 | 0.44 | 0.65 | 1.00 | 1.00 | 0.63 | 0.76 | 0.78 | 0.52 |
| Esmolol | 1.00 | 1.00 | 1.00 | 1.00 | 0.40 | 1.00 | 0.40 | 1.00 | 1.00 | 1.00 | 1.00 | 0.40 | 0.63 | 1.00 |
| Metoprolol | 0.55 | 0.50 | 0.54 | 0.54 | 0.53 | 0.62 | 0.47 | 0.66 | 0.83 | 1.00 | 0.61 | 0.74 | 0.68 | 0.53 |
| Nebivolol | 0.39 | 0.48 | 0.42 | 0.42 | 0.42 | 0.57 | 0.33 | 0.57 | 1.00 | 1.00 | 0.54 | 0.70 | 0.72 | 0.42 |
| Practolol | 1.00 | 1.00 | 1.00 | 1.00 | 0.40 | 1.00 | 0.40 | 1.00 | 1.00 | 1.00 | 1.00 | 0.40 | 0.63 | 1.00 |
| Carvedilol | 0.54 | 0.61 | 0.73 | 0.22 | 0.71 | 0.62 | 0.45 | 0.73 | 0.43 | 0.90 | 0.70 | 0.75 | 0.65 | 0.63 |
| Labetalol | 0.55 | 0.72 | 0.57 | 0.57 | 0.68 | 0.65 | 0.51 | 0.61 | 0.99 | 1.00 | 0.76 | 0.85 | 0.86 | 0.68 |

Figure 5:
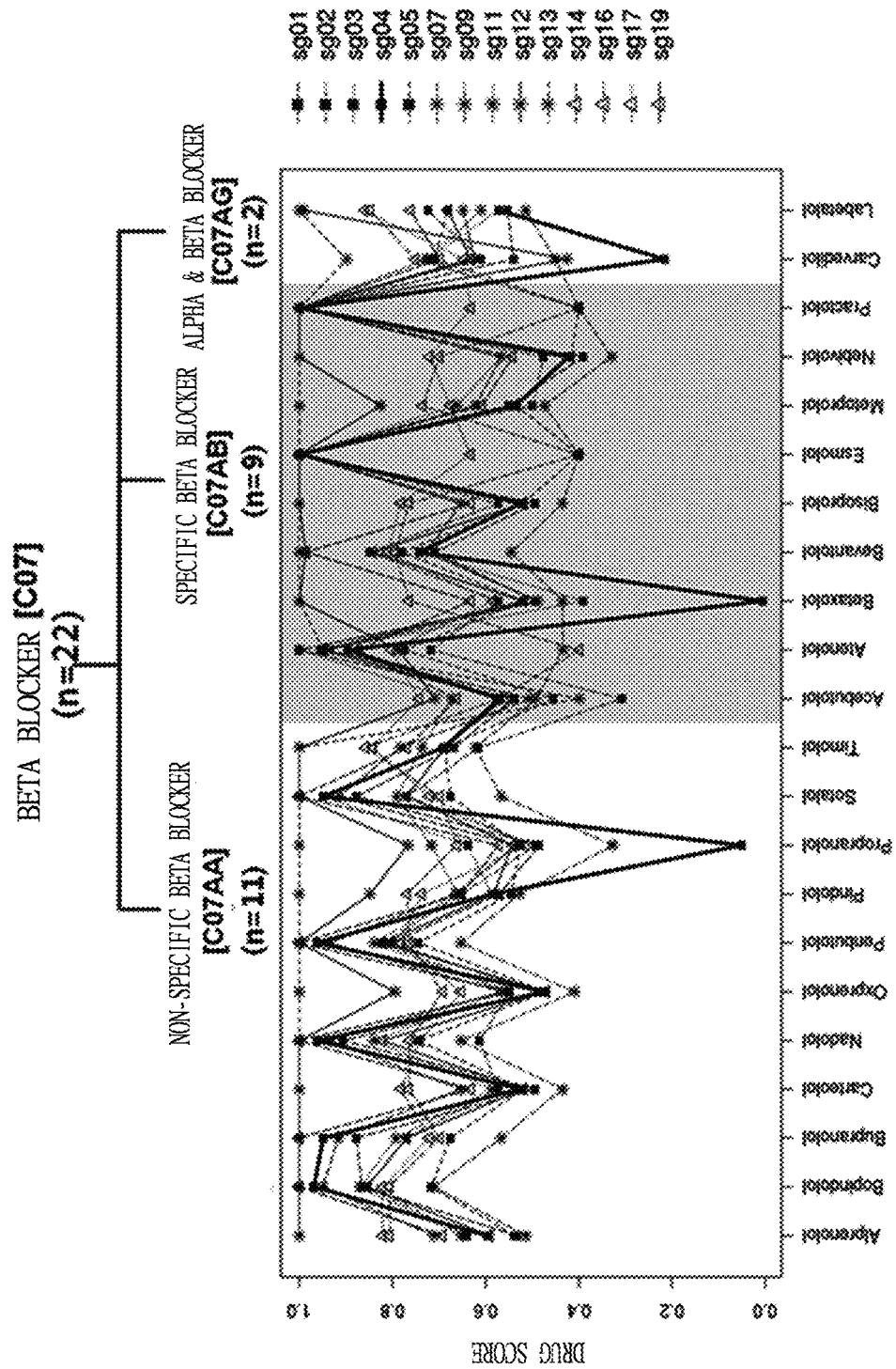
FIG. 5 is a diagram illustrating a calculated individual drug score profile of 14 persons with respect to 22 drugs belonging to ATC (Anatomical Therapeutic Chemical Classification System) Code C07 beta blockers, by using a method according to the present invention on the basis of individual genome sequence variation information.

As listed in Table 19 and illustrated in FIG. 5, it was observed that the individual sg04 had remarkably low individual drug scores with respect to Propranolol among the non-specific beta blockers [C07AA] and Betaxolol among the specific beta blockers [C07A13]. To be more specific, as for the individual sg04, the individual drug scores with respect to Betaxolol and Propranolol were as low as 0.005 and 0.05, respectively. Therefore, if the above drugs were prescribed for the individual sg04 without consideration of such low drug scores, both of the two drugs are highly likely to cause considerable side effects. Meanwhile, the individual sg04 had individual drug scores of higher than 0.9 with respect to Atenolol, Sotalol, Bupranolol, Nadolol, Penbutolol, Bopindolol, Practolol, and Esmolol among the same drug group and thus did not have currently known protein damage relevant to the drugs described above. Therefore, it can be seen that these drugs can be determined as relatively safe drugs and recommended when selecting. Further, such analysis has an advantage of displaying weakness of a specific individual with respect to a certain drug in a specific drug group so as to be recognized at a glance.

Meanwhile, it can be seen from FIG. 5 that except the individual sg04 having a tendency to show extremely low scores with respect to Betaxolol and Propranolol, most of the 14 individuals had drugs scores of 0.3 or more with respect to the 22 beta blockers. Considering this point, if a specific individual has an individual drug score of lower than 0.3 with respect to a beta blocker, the score is not in the general range. Therefore, it is possible to recommend attention to the drug with consideration for the likelihood of side effects of the drug. When information for determining whether or not to use a drug is provided as described above, a criteria of a drug score may be different for each drug or may varies depending on a clinical situation of using a drug, i.e., predicted gains and losses when using a drug.

In order to additionally analyze the reason why the individual sg04 shows a low individual drug score with respect to a specific drug as described above, by using gene sequence variation information relevant to a total of 15 proteins including target proteins, enzyme proteins, transporter proteins, and carrier proteins involved in the pharmacodynamics or pharmacokinetics of Betaxolol and Propranolol, an individual protein damage score and an individual drug score were obtained. The results thereof were as listed in Table 20, Table 21, and illustrated in FIG. 6.

TABLE 20

| Drug name (Drug score) | Gene/protein | Protein damage score | Protein group | Variation score | Chromosomal location | Reference genotype | Variant genotype |
|---|---|---|---|---|---|---|---|
| Betaxolol (0.005) | Adrenoceptor beta 1 (ADRB1) | 1.00 | Target (PD) | | | | |
| | Adrenoceptor beta 2, surface (ADRB2) | 0.85 | Target (PD) | 0.45 | chr5: 148206473 | G | C |
| | | | | 1.00 | chr5: 148206646 | G | A |
| | | | | 1.00 | chr5: 148206917 | C | A |
| | | | | 1.00 | chr5: 148207447 | G | C |
| | | | | 1.00 | chr5: 148207633 | G | A |
| | Cytochrome P450 1A2 (CYP1A2) | $1.0 \times 10^{-8}$ | Enzyme (PK) | $1.0 \times 10^{-8}$ | chr15: 75047221 | T | C |
| | Cytochrome P450 2D6 (CYP2D6) | 0.088 | Enzyme (PK) | 0.39 | chr22: 42525756 | G | A |
| | | | | 0.02 | chr22: 42526694 | G | A |

TABLE 21

| Drug name (Drug score) | Gene/protein | Protein damage score | Protein group | Variation score | Chromosomal location | Reference genotype | Variant genotype |
|---|---|---|---|---|---|---|---|
| Propranolol (0.05) | Adrenoceptor beta 1 (ADRB1) | 1.00 | Target (PD) | | | | |
| | Adrenoceptor beta 2, surface (ADRB2) | 0.85 | Target (PD) | 0.45 | chr5: 148206473 | G | C |
| | | | | 1.00 | chr5: 148206646 | G | A |
| | | | | 1.00 | chr5: 148206917 | C | A |
| | | | | 1.00 | chr5: 148207447 | G | C |
| | | | | 1.00 | chr5: 148207633 | G | A |
| | Adrenoceptor beta 3 (ADRB3) | 1.00 | Target (PD) | | | | |
| | Serotonin receptor 1A (HTR1A) | 1.00 | Target (PD) | | | | |
| | Serotonin receptor 1B (HTR1B) | 1.00 | Target (PD) | | | | |
| | Cytochrome P450 1A1 (CYP1A1) | 0.08 | Enzyme (PK) | 0.08 | chr15: 75015305 | C | T |

TABLE 21-continued

| Drug name (Drug score) | Gene/protein | Protein damage score | Protein group | Variation score | Chromosomal location | Reference genotype | Variant genotype |
|---|---|---|---|---|---|---|---|
| | Cytochrome P450 1A2 (CYP1A2) | $1.0 \times 10^{-8}$ | Enzyme (PK) | $1.0 \times 10^{-8}$ | chr15: 75047221 | T | C |
| | Cytochrome P450 2C19 (CYP2C19) | 1.00 | Enzyme (PK) | 1.00 | chr10: 96602622 | C | T |
| | Cytochrome P450 2D6 (CYP2D6) | 0.088 | Enzyme (PK) | 0.39<br>0.02 | chr22: 42525756<br>chr22: 42526694 | G<br>G | A<br>A |
| | Cytochrome P450 3A4 (CYP3A4) | 1.00 | Enzyme (PK) | | | | |
| | Cytochrome P450 3A5 (CYP3A5) | $1.0 \times 10^{-8}$ | Enzyme (PK) | $1.0 \times 10^{-8}$ | chr7: 99245974 | A | G |
| | Cytochrome P450 3A7 (CYP3A7) | 0.16 | Enzyme (PK) | 0.16 | chr7: 99306685 | C | G |
| | ATP-binding cassette, sub-family B, member 1 (ABCB1) | 1.00 | Transporter (PK) | 1.00<br>1.00 | chr7: 87138645<br>chr7: 87179601 | A<br>A | G<br>G |
| | Solute carrier family 22, member 2 (SLC22A2) | 0.32 | Transporter (PK) | 1.00<br>0.10 | chr6: 160645832<br>chr6: 160670282 | C<br>A | T<br>C |
| | Alpha-1-acid glycoprotein (ORM1) | 1.00 | Carrier (PK) | | | | |

As listed in Table 20, the individual sg04 had one variant (chr15:75047221) and two variants (chr22:42525756, chr22:42526694) with respect to CYP1A2 and CYP2D6, respectively, as two main enzyme proteins that degrade Betaxolol, and had low gene sequence variation scores corresponding thereto (1e-08. 0.39, 0.02, respectively). With respect to the enzyme proteins CYP1A2 and CYP2D6, individual protein damage scores calculated using Equation 2 were as low as 1.0e-8 and 0.088, respectively, and an individual drug score calculated using Equation 4 with respect to Betaxolol was as low as 0.005. Meanwhile, the individual sg04 had no gene sequence variant in ADRB1 as a target protein of Betaxolol, and 5 gene sequence variants (chr5:148206917, chr5:148206473, chr5:148206646, chr5:148207447, chr5:148207633) were found in ADRB2 but scores thereof were not low. An individual protein damage score calculated using Equation 2 with respect to ADRB2 was 0.85.

Further, as listed in Table 21, the individual sg04 had one or more severe gene sequence variations in each of 5 enzymes CYP1A1, CYP1A2, CYP2D6, CYP3A5, CYP3A7, and the like among 7 enzymes that degrade Propranolol, and had low gene sequence variation scores corresponding thereto: CYP1A1 (0.08 (chr15:75015305)); CY1A2 (1e-08 (chr15:75047221)); CYP2D6 (0.39 (chr22: 42525756); 0.02 (chr22:42526694)); CYP3A5 (1e-08 (chr7: 99245974)); and CYP3A7 (0.16 (chr7:99306685)). Further, individual protein damage scores calculated using Equation 2 with respect to CYP1A1, CYP1A2, CYP2D6, CYP3A5, and CYP3A7 were as low as 0.08, 1.0e-8, 0.088, 1.0e-8, and 0.16, respectively, and an individual drug score calculated using Equation 4 with respect to Propranolol was as seriously low as 0.05.

Figure 6:
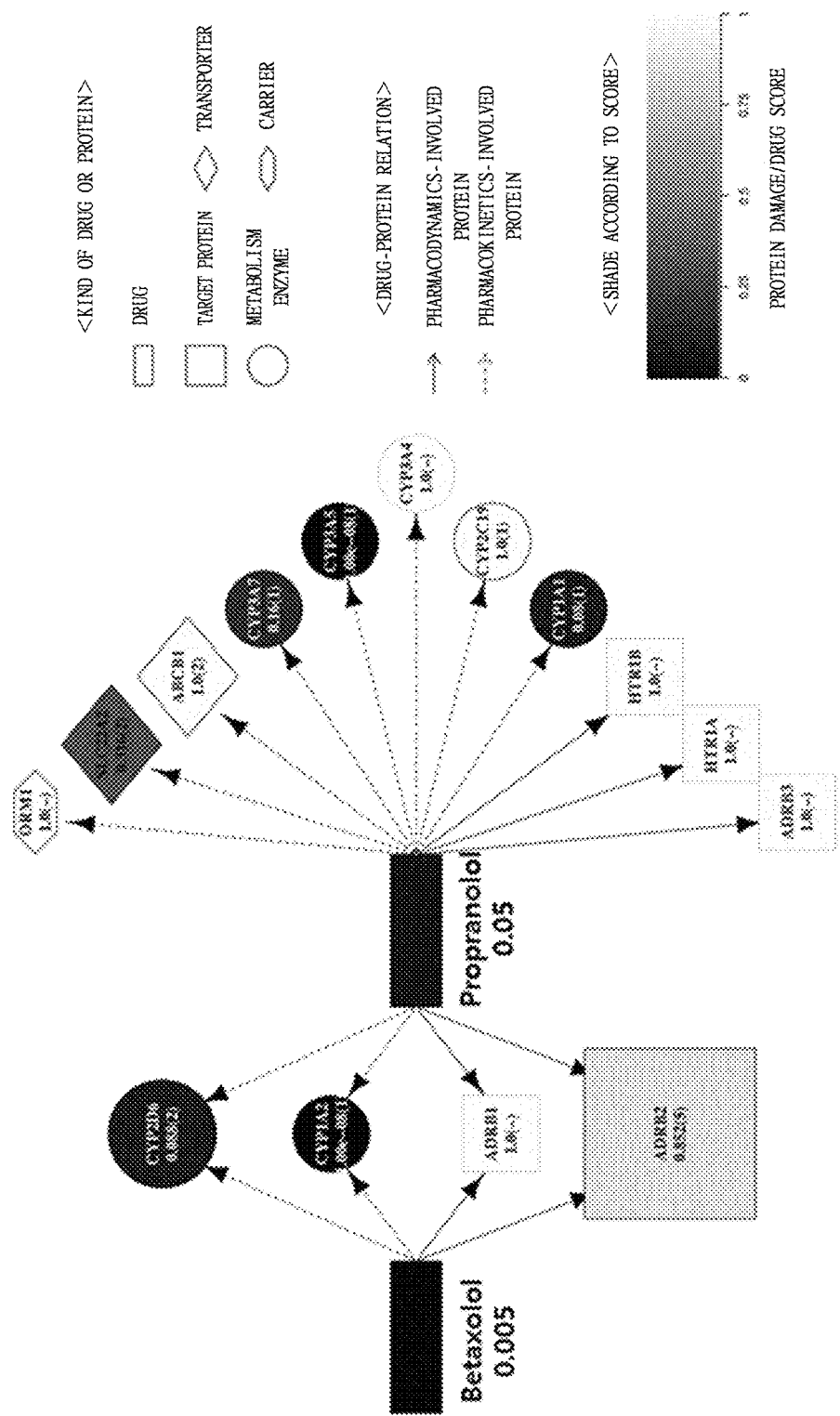
FIG. 6 is a diagram illustrating the number of gene variations for each protein, a protein damage score, and a drug score of an individual as calculated with respect to propranolol as a non-specific beta blocker and betaxolol as a specific beta blocker, by using a method according to the present invention on the basis of individual genome sequence variation information.

Further, as illustrated in FIG. 6, it was observed that the individual sg04 had significant damages in many proteins involved in drug metabolism of Betaxolol and Propranolol, and the individual drug scores of the individual sg04 with respect to Betaxolol and Propranolol were at severe levels of 0.005 and 0.05, respectively.

Therefore, in a clinical situation where it is recommended for the individual sg04 to use a beta blocker, preferably, a clinician may be provided with information so as to use drugs with a high drug score calculated according to the method of the present invention, i.e., Bopindolol (0.97), Bupranolol (0.95), Nadolol (0.96), Penbutolol (0.96), and Sotalol (0.95) among the non-specific beta blockers and Atenolol (0.9), Bevantolol (0.74), Esmolol (1.0), and Practolol (1.0) among the specific beta blockers, Labetalol (0.57) with a relatively high score among the alpha and beta blockers and so as not to prescribe Betaxolol and Propranolol, and, thus, any risk of drug side effects in the individual sg04 can be reduced.

Example 4. Demonstration of Validity of Method for Personalizing Drug Selection Based on Individual Genome Sequence Variation Information Reliable study results about individual genome sequence variation information and an individual difference in pharmacodynamics response have been very limited so far. The studies conducted so far have followed a paradigm of a case-control study in which an individual difference in responsiveness is studied by comparing a group with a specific variation with a group without the specific variation for each drug. In this study paradigm, a costly case-control study needs to be conducted to each of all combinations of pairs of numerous sequence variants and numerous drugs, which is practically impossible. Meanwhile, the method for personalizing drug selection according to the present invention is applicable to all of gene sequence variations but does not require a costly case-control study. Further, the method can calculate an individual protein damage score and an individual drug score just by calculating a genome sequence variation and suggests a method of application thereof. Therefore, the method has an advantage of being able to make a deduction for personalizing drug selection with respect to combinations between all genome sequence variations and all drugs.

In order to evaluate validity of a result of personalized drug selection according to the method of the present invention, 497 frequently prescribed drugs were selected on the basis of the following criteria; (1) drugs, of which at least one gene involved in the pharmacodynamics or pharmacokinetics is known, among drugs included in the ATC codes of top 15 frequently prescribed drug classes during 2005 to 2008 in the United States (Health, United States, 2011, Centers for Disease Control and Prevention), (2) drugs with information on the established effects of pharmacogenomic genome sequence variation markers in US FDA drug labels, and (3) drugs disclosed in the database of DrugBank as having been withdrawn from the market due to drug side effects, and the like.

As data for evaluating validity, among the established knowledge about 987 gene sequence variation-drug interaction pairs provided by PharmGKB, 650 pairs (65.9%) having at least one link to the 497 drugs were extracted. Considering that a target of the present invention is a sequence variation in an exon region, an overlapped part between data of a verification target and data of evaluation standard were removed for a fair evaluation. To be more specific, a fairer evaluation was conducted by removing pairs with all of 36 sequence variations positioned in the exon region among the 650 pairs and selecting only a sequence variation in a non-coding region. As a result, 614 pairs were selected as a final gold standard for evaluation.

Then, whole genome sequences of 1092 persons provided by the 1000 Genomes Project were analyzed, and the method according to the present invention was applied to each of the 1092 persons to thereby calculate individual pharmacogenomic risk and pharmacogenomic risk of each gene sequence variation registered at PharmGKB.

For validity evaluation, sensitivity, specificity, and an area under the Receiver Operating Curve (ROC) were used. 497 drugs were ranked on the basis of individual drug scores and threshold values were set for each ranking at 496 segment positions between ranks. Then, (1) when a ranking of a drug score of a corresponding drug was higher than a threshold and a PharmGKB variation was present in an individual genome variation, it was determined as true positive, (2) when a ranking of a drug score of a corresponding drug was lower than a threshold and a PharmGKB variation was not present in an individual genome variation, it was determined as true negative, (3) when a ranking of a drug score of a corresponding drug was higher than a threshold but a PharmGKB variation was not present in an individual genome variation, it was determined as false positive, and (4) when a ranking of a drug score of a corresponding drug was lower than a threshold but a PharmGKB variation was present in an individual genome variation, it was determined as false negative. The numbers of true positive, true negative, false positive, and false negative cases of each individual with respect to each ranking threshold L were calculated, and the sensitivity and the specificity were calculated as illustrated in the following equations.

$$\text{Sensitivity} = \frac{|D_L \cap GS|}{|DS|}$$

$$\text{Specificity} = 1 - \frac{|D_L - GS|}{|D - GS|}$$

The D is a set of all 497 drugs, the GS is a set of personalized PharmGKB drugs used as an individual gold standard since an individual gene sequence variation in each individual is identical with a risk allele of PharmGKB, the DL is a set of drugs with high ranking thresholds, and the vertical bar parenthesis means the number of elements of a corresponding set.

As a result of calculation, 18 persons had no variation identical to a variation of PharmGKB, and, thus, a set of personalized PharmGKB drugs used as an individual gold standard could not be defined. Therefore, the 18 persons were excluded from the present validity test. The sensitivity and specificity were calculated with respect to all of the thresholds, and a ROC was drawn to thereby calculate an AUC. To be more specific, gene sequence variation scores of 1092 persons in the total population group were calculated using a SIFT algorithm, and then, protein damage scores and drugs scores were calculated using Equation 2 and Equation 4, respectively. Further, in order to determine the usefulness of application of weightings according to a race distribution, race-specific sensitivity and specificity and a value of AUC based on the sensitivity and specificity were calculated in the same manner for each of four races (African (AFR, n=246), American (AMR, n=181), Asian (ASN, n=286), European (EUR, n=379)) clearly stated in the 1000 Genomes Project, so that race-specific sensitivity and specificity and an AUC were obtained. The results thereof were as listed in Table 22, Table 23, and illustrated in FIG. 7.

TABLE 22

Distribution of each protein group and Calculation of an average protein damage score

| Protein group | Number of proteins | Number of relevant drugs | Number of protein-drug pairs | Mean protein damage score |
|---|---|---|---|---|
| Target protein | 440 | 486 | 2357 | 0.798 |
| Carrier protein | 10 | 50 | 65 | 0.728 |
| Enzyme protein | 74 | 330 | 1347 | 0.733 |
| Transporter protein | 54 | 176 | 457 | 0.733 |
| Total | 545 | 497 | 4201 | 0.783 |

TABLE 23

Calculation of the valididty(AUC) of the drug score calculation for each protein group and each race using The 1000 Genomes Project data

| | Total | AFR | AMR | ASN | EUR |
|---|---|---|---|---|---|
| Validity (AUC) of the drug score calculation | | | | | |
| Target protein | 0.617 | 0.634 | 0.608 | 0.614 | 0.614 |
| Carrier protein | 0.554 | 0.511 | 0.599 | 0.485 | 0.594 |
| Enzyme protein | 0.587 | 0.642 | 0.580 | 0.558 | 0.579 |
| Transporter protein | 0.497 | 0.492 | 0.488 | 0.489 | 0.512 |
| Validity (AUC) of the drug score calculation in the case where weightings are not applied to each protein group or the case where weightings are applied to each protein group | | | | | |
| Simple geometric mean | 0.666 | 0.744 | 0.650 | 0.634 | 0.653 |
| Weighted geometric mean | 0.667 | 0.742 | 0.652 | 0.633 | 0.654 |

Table 22 lists a distribution of proteins relating to 497 drugs used in the present Example for each protein group, and indicates the number of protein-drug pairs together with an average protein damage score for each group.

Table 23 lists validity of individual drug score calculation (AUC) respectively calculated in the case where weightings are not applied to each protein group (simple geometric mean) and the case where weightings are applied to each protein group (weighted geometric mean) when calculating a drug score using Equation 4 with respect to each protein group and each race.

To be more specific, for example, in the total population group, AUC values calculated for protein groups such as target proteins, carrier proteins, metabolism enzyme proteins, and transporter enzymes were 0.617, 0.554, 0.587, and 0.497, respectively. These values were used as weightings for the respective protein groups (each value was substituted for the weighting wi of Equation 4) to thereby obtain the validity of individual drug score calculation using weighted geometric mean (AUC=0.667) (refer to FIG. 7b). As a result, it was confirmed that the validity of individual drug score calculation using weighted geometric mean in the case of assigning the weightings for the respective protein groups were increased by 0.001 point as compared with the validity of individual drug score calculation using simple geometric mean (AUC=0.666) calculated by applying a simple geometric mean calculation formula without assigning a weighting (weighting wi=1) (refer to FIG. 7a).

Figure 7A:
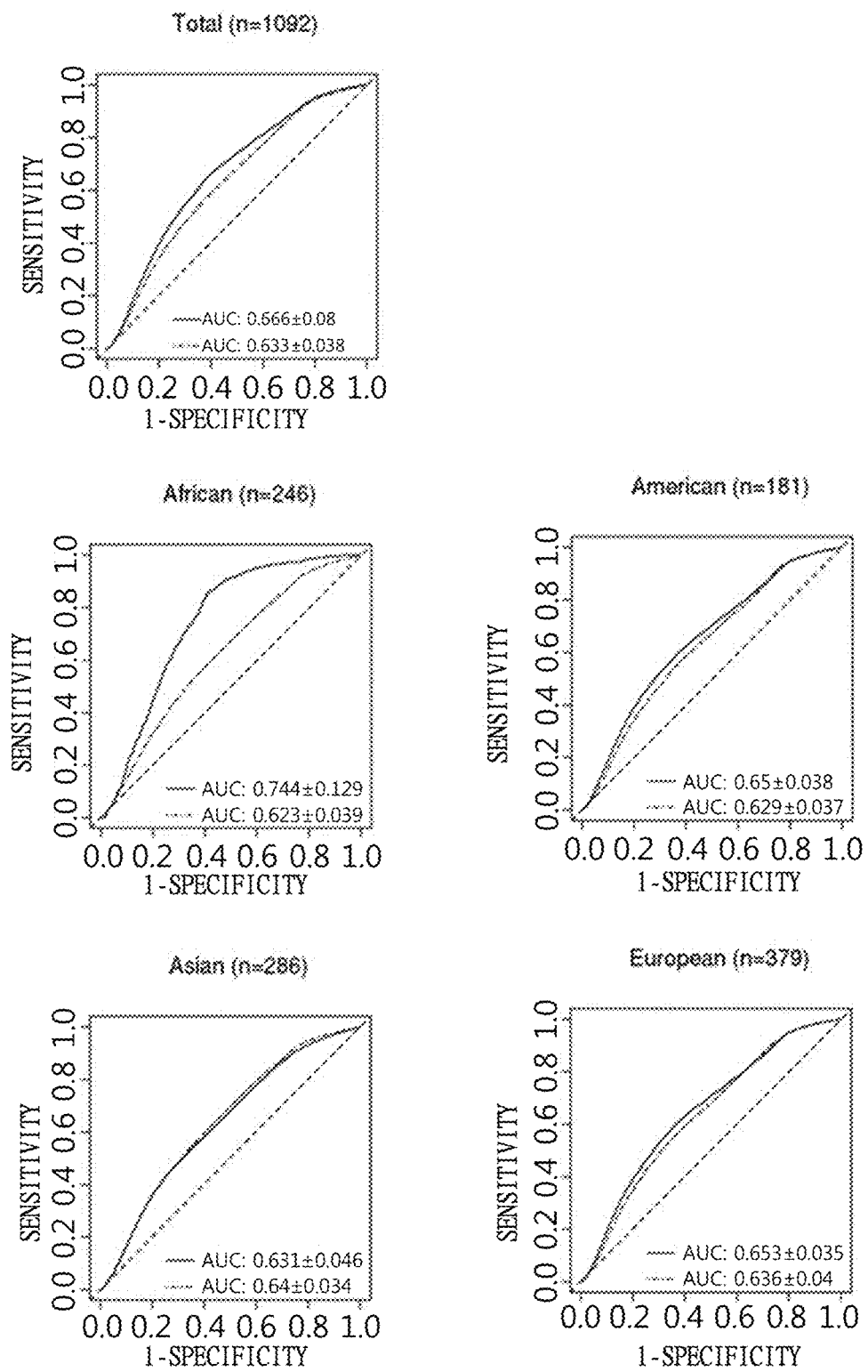
FIG. 7 illustrates the validity of drug score calculation (AUC (Area Under Curve) calculated on the basis of a comparison analysis with gene-drug pairs provided by PharmGKB Knowledge Base and individual genome sequence variation information of 1092 persons provided by the 1000 Genomes Project, by using a method according to the present invention (FIG. 7a: validity of individual drug score calculation (AUC) calculated by a simple geometric mean formula to which a weighting for each protein class is not applied, FIG. 7b: validity of individual drug score calculation (AUC) calculated by a weighted geometric mean formula to which a weighting for each protein class is applied).

Further, as illustrated in FIG. 7a, as another example of application of weightings, weightings were assigned according to the number of people per race and a validity of individual drug score calculation (AUC) was analyzed. As a result, in the case of considering a race specificity (bold line), the AUC value of the total population group (Total) was 0.666 (African: 0.744, American: 0.650, Asian: 0.631, and European: 0.653), and in the case of not considering a race specificity (dotted line), the AUC value of the total population group was 0.633 (African: 0.623, American: 0.629, Asian: 0.64, and European: 0.636). Accordingly, it was confirmed that the validity of individual drug score calculation in the case of considering a race specificity was improved as compared with the case of not considering a race specificity.

Figure 7B:
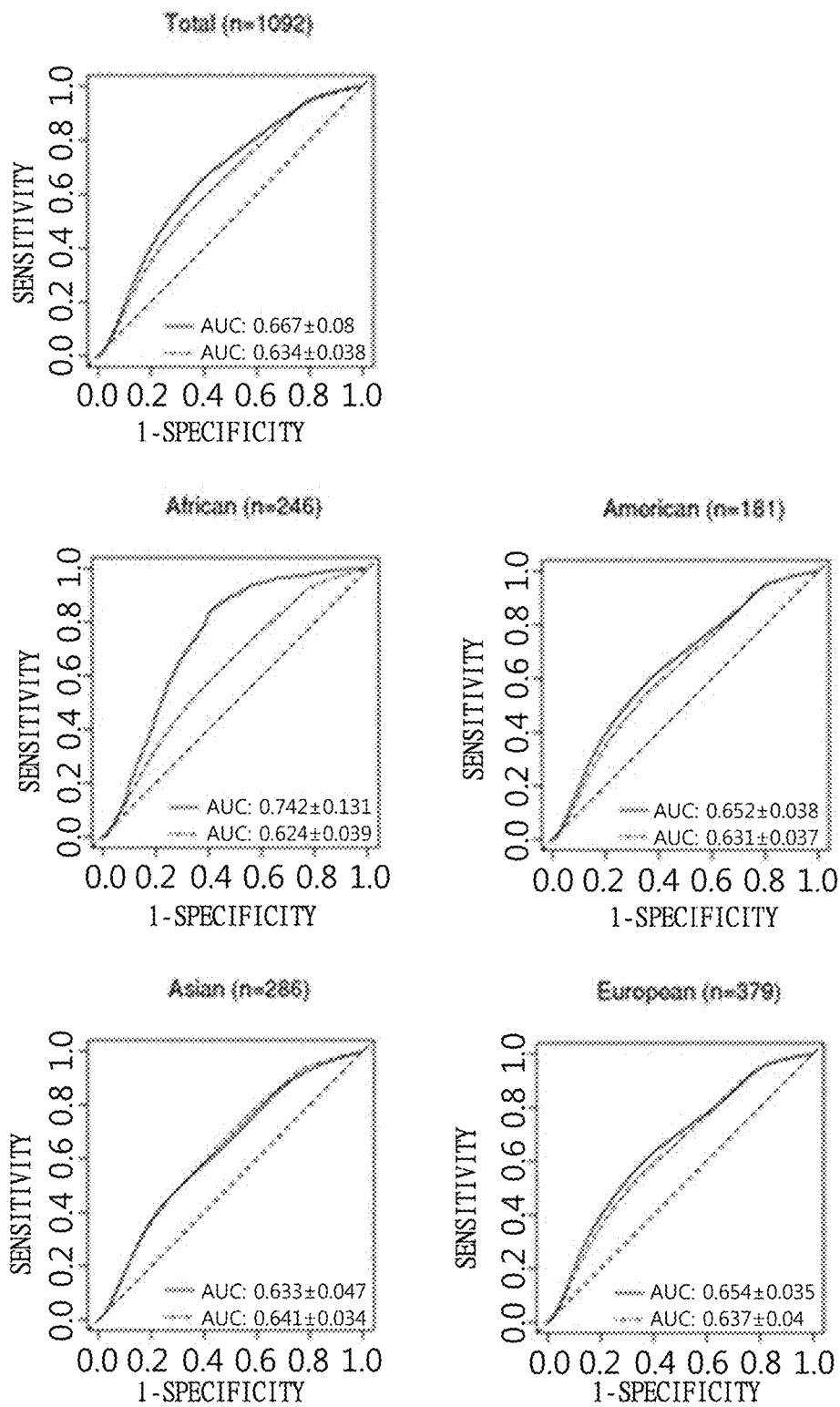

Further, as illustrated in FIG. 7b, in the case of assigning weightings for the respective protein groups without considering a race specificity (dotted line), validity of individual drug score calculation (AUC) of the present invention was 0.634, and in the case of assigning weightings for the respective protein groups while considering a race specificity (bold line), validity of individual drug score calculation (AUC) of the present invention was 0.667. Accordingly, it can be seen that different weightings are useful.

Example 5. Demonstration of Validity of the Present Invention Through Individual Genome Sequence Variation Information Analysis on Pediatric Leukemia Patients Showing Warning Signs of Serious Side Effects During Treatment with Anticancer Drug Busulfan Bone marrow transplantation is one of the most important treatment method for treating blood tumor such as leukemia. For bone marrow transplantation, bone marrow of a patient needs to be removed first by using two methods: total body irradiation (TBI); and a pharmacological treatment using drugs such as Busulfan. Busulfan is a representative alkylating agent and can substitute for total body irradiation. However, it has a relatively narrow therapeutic range. Thus, if a drug concentration is higher than the therapeutic range, hepatic veno-occlusive disease (VOD) and severe toxicity, such as neurotoxicity, relevant to the drug occurs, and if a drug concentration is lower than the therapeutic range: the likelihood of graft failure or recurrence is increased. Particularly, pediatrics are greatly different from each other in the pharamacokinetics of Busulfan. Therefore, Busulfan is used under therapeutic drug monitoring (TDM). Toxicity of Busulfan includes interstitial lung fibrosis commonly called "Busulfan Lung", hyperpigmentation, epilepsy, veno-occlusive disease (VOD), nausea, thrombocytopenia, and the like. The IARC (International Agency for Research on Cancer) classifies Busulfan as one of Group 1 carcinogens.

In order to check whether it is possible to identify a risk group with respect to the Busulfan treatment through the method for personalizing drug selection using individual genome sequence variations of the present invention, the following experiment was conducted. Firstly, an analysis was conducted on 12 pediatric leukemia patients showing warning signs of serious side effects with a high AUC (AUC 6-hour) after administration according to an opinion under TDM (therapeutic drug monitoring) during a treatment with an anticancer drug Busulfan (Myleran, GlaxoSmithKline, Busulfex IV, Otsuka America Pharmaceutical, Inc.) to remove bone marrow as a pre-treatment for bone marrow transplantation. For objective comparison, gene sequence comparison analysis was conducted on 14 cases in a normal control group and 286 Asians provided by the 1000 Genomes Project (http://www.1000genomes.org/). Firstly, genes involved in the pharmacodynamics or pharmacokinetics of Busulfan and its metabolic product were searched, and then, 12 genes (CTH, GGT1, GGT5, GGT6, GGT7, GSTA1, GSTA2, GSTM1, GSTP1, MGMT, MGST2, MSH2) were selected.

From gene sequence variation information of the 12 pediatric leukemia patients and the 14 cases in the normal control group with respect to the 12 genes, gene sequence variation scores were calculated using a SIFT algorithm. Then, from the gene sequence variation scores, individual protein damage scores and individual drug scores were calculated according to the present invention. To be more specific, on the basis of individual gene sequence variation information, individual protein damage scores with respect to the 12 genes were calculated using Equation 2, and individual drug scores were calculated using Equation 4. The results thereof were as listed in Table 24. The Asians were divided into sub-population groups CHB (Han Chinese in Beijing, China) (n=97), CHS (Southern Han Chinese) (n=100), and JPT (Japanese in Tokyo, Japan) (n=89), and the same analysis was conducted on these groups. Each of individual protein damage scores and drug scores was calculated using a geometric mean, a harmonic mean or a product.

TABLE 24

|  | Busulfan (n = 12) | Normal Control (n = 14) | Asian (n = 286) | CHB (n = 97) | CHS (n = 100) | JPT (n = 89) |
|---|---|---|---|---|---|---|
| Individual Drug score | | | | | | |
| Geometric mean | 0.507 ± .065 | 0.589 ± .079[§] | 0.576 ± .084[§] | 0.566 ± .068* | 0.588 ± .082[§] | 0.575 ± .101[§] |
| Harmonic mean | 0.282 ± .049 | 0.327 ± .087 | 0.331 ± .076[§] | 0.326 ± .065* | 0.332 ± .067[§] | 0.336 ± .094[§] |
| Product | 2.83e−5 ± 5.75e−5 | 2.00e−3 ± 4.43e−3 | 2.92e−4 ± 9.75 ± e−4[§] | 3.94e−4 ± 1.17e−3[§] | 2.69e−4 ± 1.05e−3* | 2.06e−4 ± 5.77e−4[§] |
| Individual Protein damage score | | | | | | |
| *Geometric mean* | | | | | | |
| CTH | 0.3429 | 0.3714 | 0.6647 | 0.6645 | 0.6689 | 0.6638 |
| GGT1 | 1.0000 | 1.0000 | 0.9264 | 0.8914 | 0.9569 | 0.9201 |
| GGT5 | 0.3598 | 0.4800 | 0.6265 | 0.6071 | 0.6600 | 0.6139 |
| GGT6 | 0.1826 | 0.2171 | 0.2061 | 0.1953 | 0.2069 | 0.2174 |
| GGT7 | 0.8692 | 1.0000 | 0.9741 | 0.9718 | 0.9636 | 0.9889 |
| GSTA1 | 1.0000 | 1.0000 | 0.9968 | 1.0000 | 1.0000 | 0.9897 |
| GSTA2 | 0.3688 | 0.5132 | 0.4916 | 0.5067 | 0.4740 | 0.4955 |
| GSTM1 | 0.6654 | 0.6371 | 0.3513 | 0.3448 | 0.3347 | 0.3752 |
| GSTP1 | 1.0000 | 0.9665 | 1.0000 | 1.0000 | 1.0000 | 1.0000 |
| MGMT | 0.8230 | 0.9621 | 0.8754 | 0.8736 | 0.9078 | 0.8361 |
| MGST1 | 1.0000 | 1.0000 | 0.9968 | 0.9939 | 0.9968 | 1.0000 |
| MSH2 | 0.2677 | 0.7793 | 0.3615 | 0.3605 | 0.3793 | 0.3412 |
| *Harmonic mean* | | | | | | |
| CTH | 0.3425 | 0.3714 | 0.6647 | 0.6645 | 0.6689 | 0.6638 |
| GGT1 | 1.0000 | 1.0000 | 0.9252 | 0.8899 | 0.9557 | 0.9189 |
| GGT5 | 0.3042 | 0.4664 | 0.6225 | 0.6015 | 0.6561 | 0.6115 |
| GGT6 | 0.0859 | 0.1437 | 0.0942 | 0.0903 | 0.0943 | 0.0985 |
| GGT7 | 0.8692 | 1.0000 | 0.9739 | 0.9718 | 0.9630 | 0.9889 |
| GSTA1 | 1.0000 | 1.0000 | 0.9968 | 1.0000 | 1.0000 | 0.9897 |
| GSTA2 | 0.3386 | 0.4934 | 0.4759 | 0.4948 | 0.4540 | 0.4808 |
| GSTM1 | 0.6554 | 0.6371 | 0.2965 | 0.3011 | 0.2702 | 0.3200 |
| GSTP1 | 1.0000 | 0.9533 | 1.0000 | 1.0000 | 1.0000 | 1.0000 |
| MGMT | 0.7869 | 0.9543 | 0.8512 | 0.8516 | 0.8871 | 0.8045 |
| MGST1 | 1.0000 | 1.0000 | 0.9968 | 0.9939 | 0.9968 | 1.0000 |
| MSH2 | 0.2643 | 0.7793 | 0.3579 | 0.3587 | 0.3737 | 0.3381 |
| *Product* | | | | | | |
| CTH | 0.3320 | 0.3714 | 0.6643 | 0.6633 | 0.6689 | 0.6638 |
| GGT1 | 1.0000 | 1.0000 | 0.9237 | 0.8880 | 0.9537 | 0.9184 |
| GGT5 | 0.2190 | 0.4530 | 0.5942 | 0.5642 | 0.6324 | 0.5882 |
| GGT6 | 0.0423 | 0.1179 | 0.0372 | 0.0413 | 0.0370 | 0.0326 |
| GGT7 | 0.8692 | 1.0000 | 0.9725 | 0.9707 | 0.9600 | 0.9889 |
| GSTA1 | 1.0000 | 1.0000 | 0.9968 | 1.0000 | 1.0000 | 0.9897 |
| GSTA2 | 0.2528 | 0.4039 | 0.3943 | 0.4082 | 0.3728 | 0.4022 |
| GSTM1 | 0.6450 | 0.6371 | 0.2371 | 0.2542 | 0.2101 | 0.2486 |
| GSTP1 | 1.0000 | 0.9393 | 1.0000 | 1.0000 | 1.0000 | 1.0000 |
| MGMT | 0.7400 | 0.9443 | 0.8223 | 0.8247 | 0.8660 | 0.7634 |
| MGST1 | 1.0000 | 1.0000 | 0.9968 | 0.9939 | 0.9968 | 1.0000 |
| MSH2 | 0.2141 | 0.7793 | 0.3375 | 0.3433 | 0.3473 | 0.3194 |

*p-value < 0.05 and
[§]p-value < 0.01 by Student T-test.
Values are mean or mean ± S.D.

As listed in Table 24, according to the calculation result of the individual drug scores using the geometric mean, the harmonic mean or the product, respectively, in the cases of using the geometric mean (p=0.016) and the product (p=0.001), results of an Oneway Analysis of Variance among the pediatric leukemia patients (n=12) exhibiting warning signs of serious side effects after administration of Busulfan, the normal control group (n=14), and the Asians (n=286) were statistically significant, and in the case of using the harmonic mean, results showed a significant tendency (p=0.088).

Meanwhile, as a result of T-test analysis of individual drug scores calculated using the geometric mean, the harmonic mean or the product, it was confirmed that all of the normal persons vs the Asians (n=286) (p=0.579, 0.872, 0.173), the normal persons vs CHB (n=97) (p=0.327, 0.942, 0.20), the normal persons vs CHS (n=100) (p=0.967, 0.837, 0.169), and the normal persons vs JPT (n=89) (p=0.559, 0.735, 0.154) did not show statistical significance based on a p-value. From the above-described result, it was confirmed that it is possible to significantly differentiate a group (a risk group with respect to the Busulfan treatment) illustrating warning signs of serious side effects during a treatment with Busulfan from a no-risk group by using calculation of individual drug scores through analysis of individual genome sequence variation information according to the present invention and also possible to prevent an unwanted side effect.

Further, gene sequence variation information involved in the pharmacodynamics or pharmacokinetics and pharmacological pathway of Busulfan as an anticancer drug and bone-marrow inhibitor was determined by conducting individual gene sequence analysis on the 12 pediatric leukemia patients and the 14 cases in the normal control group, and distribution of means and standard deviations of individual protein damage scores (calculated using Equation 2) and individual drug scores (calculated using Equation 4) calculated from the gene sequence variation information was as illustrated in FIG. 8.

As illustrated in FIG. 8, the two groups did not show a remarkable difference in protein damage scores of the genes GGT1, GSTA1, GSTP1, MGST1, but showed a certain difference in protein damage scores of the genes CTH, GGT5, GGT6, GGT7, GSTA2, MGMT, MSH2. Meanwhile, it was observed that a protein damage score of the gene GSTM1 was slightly higher in the pediatric leukemia patient group (0.665) than the normal control group (0.637). As shown in the above-described result, it is difficult to identify the two groups with the individual gene variation or protein damage scores, but in the case of using the method for personalizing drug selection of the present invention, it is possible to statistically significantly identify the two groups by calculating a summarized drug score (refer to Table 24).

Figure 8A:
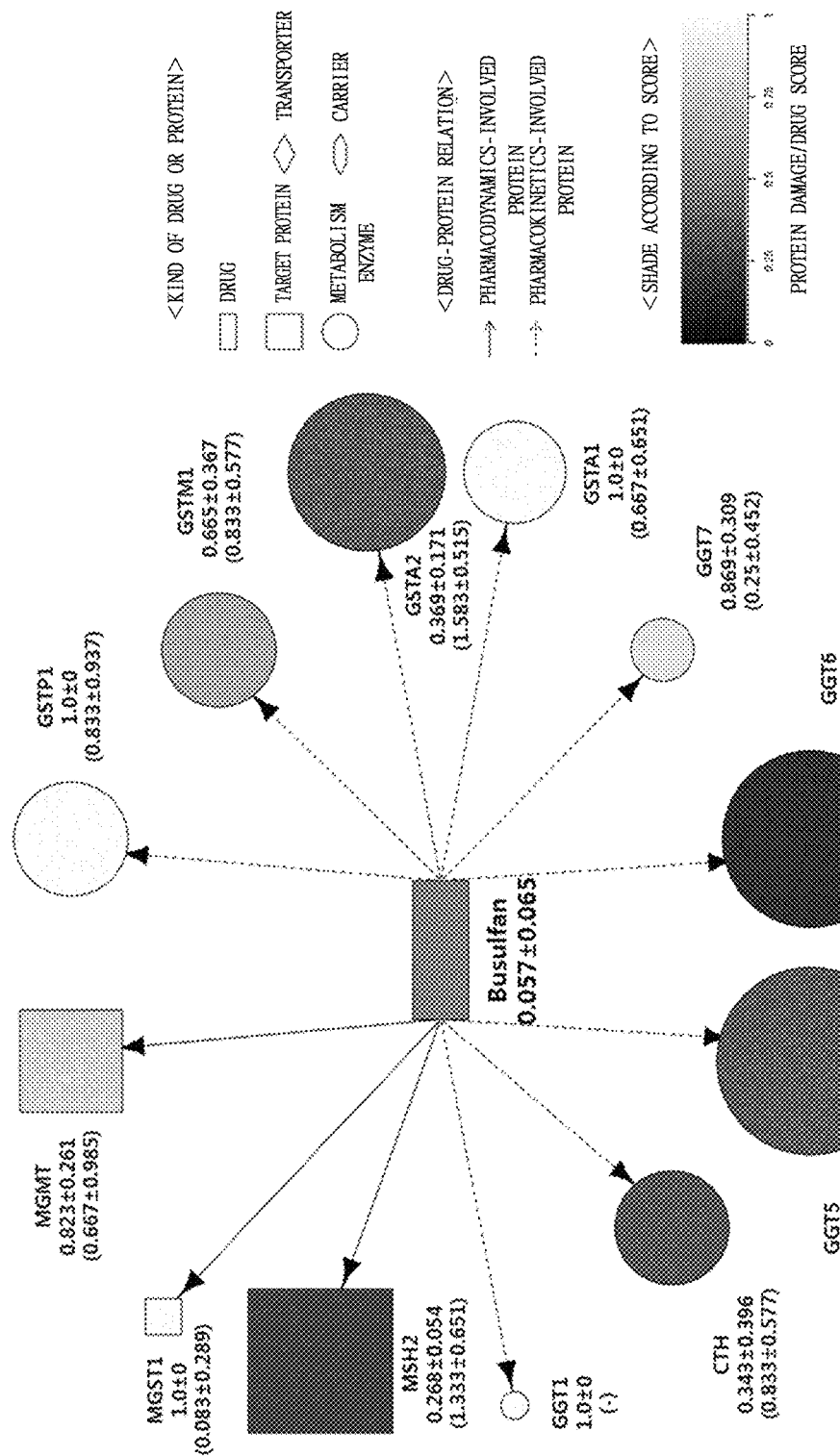
FIG. 8 illustrates distribution of means and standard deviations of individual protein damage scores and drug scores calculated by using a method according to the present invention on the basis of individual genome sequence variation information in 12 pediatric leukemia patients (FIG. 8a) exhibiting warning signs of serious side effects during a treatment with Busulfan as an anticancer drug and bone-marrow inhibitor and 14 cases in a normal control group (FIG. 8b). A size of each shape means the number of gene sequence variations.
Figure 8B:
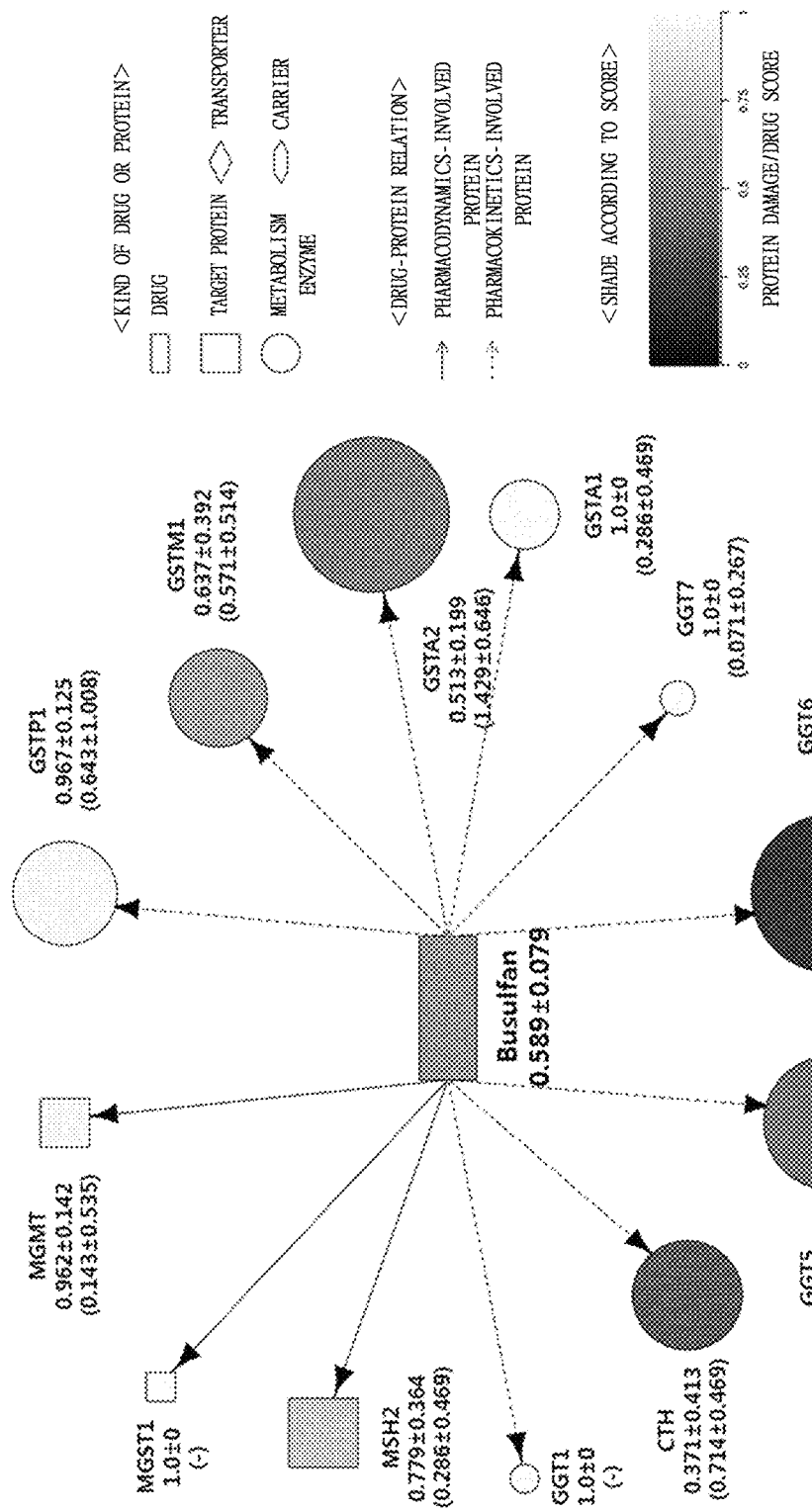

Further, a size of each figure in FIG. 8 means the frequency of gene sequences, and it was confirmed that sizes of figures for the pediatric leukemia patient group (FIG. 8a) are greater than sizes of figures for the normal control group (FIG. 8b). Therefore, it is possible to recognize at a glance that the number of gene sequence variations used for calculating the summarized drug score is greater in the pediatric leukemia patient group.

With the above-described result, it is possible to predict a group with a high likelihood of side effects when Busulfan is administered to a pediatric leukemia patient, according to the method of the present invention, and also possible to induce a high-risk group to adjust a drug concentration or use an alternative treatment method or interventional method.

Example 6. Demonstration of Validity of the Present Invention Through Analysis of Individual Genome Sequence Variation Information Found in Gene Involved in Pharmacodynamics or Pharmacokinetics of Drug Withdrawn from Market Any drug approved by the FDA and sold in the market can be ordered to be withdrawn from the market according to a result of a post-market surveillance (PMS) while being widely used. Such withdrawal of a drug from the market is a medically critical issue. Even a drug approved after the whole process of a strict clinical trial may cause unpredicted side effects in an actual application step with enormous sacrifices of life and economic losses and thus may be withdrawn. An individual difference which cannot be found in a large-scale clinical trial is regarded as one of causes for withdrawal of a drug from the market. The method for personalizing drug selection according to the present invention provides a method for precluding the use of drugs with high risk for each individual in consideration of an individual difference. Accordingly, if it is possible to predict withdrawal of a drug, which causes enormous medical and economic losses, from the market by the method for personalizing drug selection according to the present invention, the validity of the present invention can be demonstrated again.

In order to do so, an analysis was conducted on the same population group (n=1097) as Example 4 and the drug group (n=497) with withdrawn drugs from the market and drugs restricted to use. In order to construct a comprehensive list of withdrawn drugs from the market, the document "List of Withdrawn Drugs" from Wikipedia and "Consolidated List of Products Whose Consumption and/or Sale Have Been Banned, Withdrawn, Severely Restricted, or Not Approved by Governments: Pharmaceuticals" Versions 8, 10, 12, and 14 as the most comprehensive data about the withdrawn drugs from the worldwide market issued by the U.N. were reviewed overall in addition to the already included list of withdrawn drugs from the market from the DrugBank database. Finally, a list of 392 withdrawn drugs from at least one country was constructed, and it was confirmed that 82 drugs of them were included in the above-described 497 drugs. Further, a drug, which has not been withdrawn from the market but severely restricted to use, was extracted from a union of the list of drugs given "Boxed Warning" from the US FDA and the drugs indicated as "severely restricted" in the U.N. report and also included in the above-described 497 drugs, and it was confirmed that the number of drugs in the drug group was 139. An analysis was conducted on the 82 withdrawn drugs from the market, the 139 drugs restricted to use, and the other 276 drugs. A market safety score or a population group drug score of each drug was obtained by calculating gene sequence variation scores using a SIFT algorithm on the basis of genome sequence variations of the 1092 persons and acquiring an arithmetic mean of 1092 individual drug scores calculated from the gene sequence variation scores. As a result, the population group drug scores of the withdrawn group, the restricted group, and the other group were 0.585±0.21, 0.592±0.19, and 0.664±0.19, respectively, and as a result of an Oneway Analysis of Variance, a difference thereof was significant (F=9.282, p<0.001). Further, as a result of a post Tukey analysis, a p-value between the withdrawn drug and the other drug was 0.004 and a p-value between the restricted drug and the other drug was 0.001, and the both values showed a statistical significance. A significant difference between the withdrawn drug and the restricted drug was not found (p-value=0.971). That is, it can be seen that in the population group, as a mean of drug scores suggested by the method for personalizing drug selection of the present invention is decreased, the likelihood of withdrawal and restriction of the drug is significantly increased and the corresponding drug has a high risk.

Figure 9A:
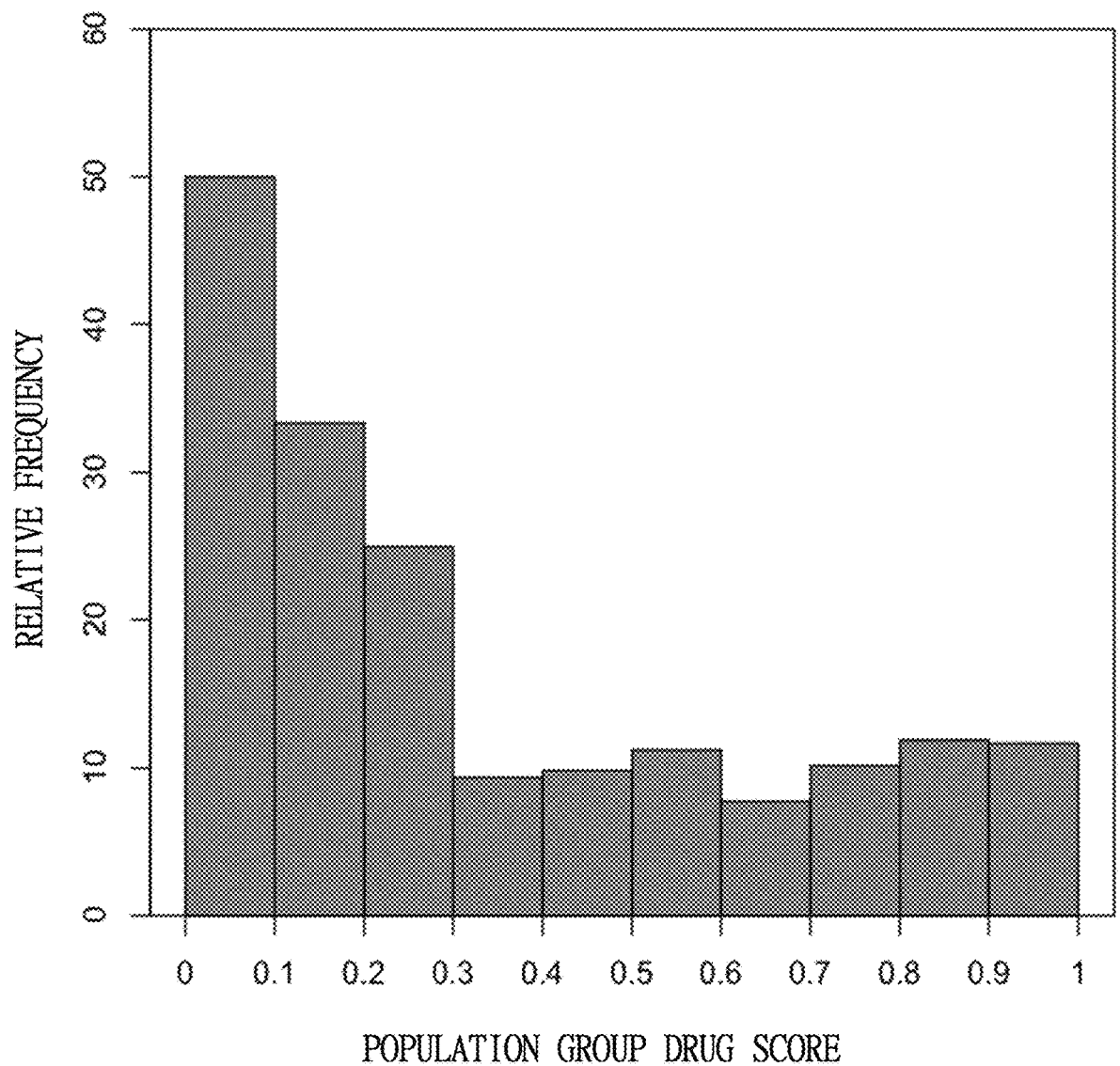
FIG. 9 illustrates a relative frequency histogram displaying a relative frequency of withdrawn drugs from the market as obtained from DrugBank and Wikipedia (FIG. 9a) and withdrawn drugs from the market and drugs restricted to use as obtained from the U.N.
(FIG. 9b) against a population group drug score calculated on the basis of individual genome sequence variation information of 1092 persons provided by the 1000 Genomes Project by using a method according to the present invention.
Figure 9B:
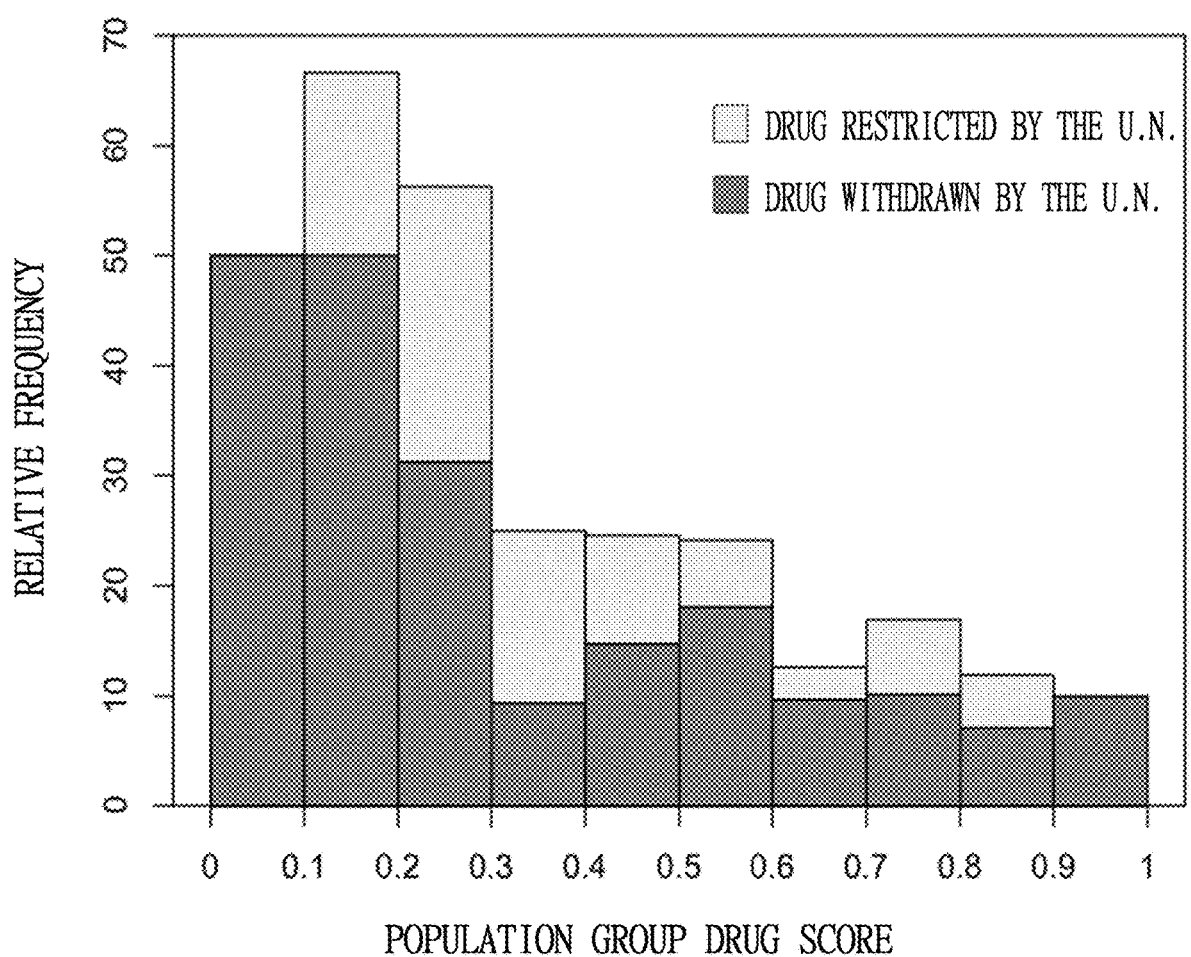

The usefulness of a drug score according to the present invention is clearly visualized with relative frequency histograms as illustrated in FIG. 9. FIG. 9a is a relative frequency histogram according to population group drug scores of withdrawn drugs from the market as obtained from DrugBank and Wikipedia, and FIG. 9b is a relative frequency histogram according to population group drug scores of withdrawn drugs from the market and drugs restricted to use as obtained from the U.N. data.

As illustrated in FIG. 9, drugs were respectively allotted to 10 score sections divided by 0.1 between 0.0 and 1.0 according to a population group drug score of a corresponding drug, and then, withdrawal rates of the drugs corresponding to the respective 0.1 sections were represented by a histogram. It was confirmed that when an arithmetic mean of 1092 individual drug scores calculated according to the present invention on the basis of the population group drug scores or genome sequence variations of the 1092 persons was low, a withdrawal rate was remarkably high. Particularly, it was confirmed that a drug having a population group drug score of 0.3 or less had a remarkably high likelihood of being withdrawn from the market or restricted to use. It can be seen from the above-described result that an individual drug score according to the present invention can suggest a mechanism capable of avoiding a drug with a potential risk of being withdrawn from the market or restricted to use in a personalized manner by using characteristics of individual gene sequence variations.

Example 7. Contemplation of Clinical and Medical Significance Through Analysis of Individual Genome Sequence Variation Relevant to Target Protein of Specific Drug with Predicted Risk In order to verify the usefulness of the method for personalizing drug selection of the present invention by contemplating a clinical and medical significance of an individual genome sequence variation found in a target protein of a specific drug with a predicted risk for an individual, the following experiment was conducted.

A detailed analysis was conducted on the individual sg01 which had a normal blood coagulation ability but had a low individual drug score with respect to an anticoagulant Rivaroxaban calculated according to an analysis of individual gene sequence variation and the present invention. To be more specific, in an individual genome sequence of the individual sg01, two gene sequence variations (13th chromosome 113801737 and 113795262) occurred at a coagulation factor 10 (F10) as a target protein among 5 genes involved in the pharmacodynamics or pharmacokinetics of Rivaroxaban (an individual protein damage score calculated using Equation 2 after calculation of a gene sequence variation score using a SIFT algorithm was 0.0001), and one gene sequence variation (1st chromosome 60392236) occurred at an enzyme protein CYP2J2. As a result of calculating the individual drug score of the individual sg01 with respect to Rivaroxaban using Equation 4 according to the method of the present invention on the basis of the gene sequence variation information, it was confirmed that the individual drug score was as low as 0.148.

A hypofunction of a blood coagulation factor is a very important mechanism as a cause for hemophilia. Hemophilia mainly occurs due to functional deficiency of coagulation factors 8, 9 and 11, but a case caused by the coagulation factor 10 (F10) is hardly known. The F10 is a very important enzyme for converting prothrombin to thrombin. In the case of a homozygote including a pair of severely damaged F10 genes, the individual sg01 may show an extreme tendency such as a high hemorrhagic tendency or cannot survive. However, as a result of the sequence analysis on the individual sg01, the pair of F10 genes was a heterozygote in which only one of the pair of F10 genes had a sequence variation and there was no damage to a function of the other gene.

As such, the individual sg01 having a normal blood coagulation ability did not recognize but had a high likelihood of side effects of Rivaroxaban as a result of calculation of the drug score according to the present invention, which has a clinical and medical significance. Therefore, for additional analysis, detailed analysis was conducted on the blood coagulation ability of the individual sg01. The result thereof was as listed in Table 25.

TABLE 25

| Blood coagulation factor | Activity | Normal range reference |
|---|---|---|
| Factor 2 | 109% | 84-139 |
| Factor 5 | 113% | 63-140 |
| Factor 7 | 127% | 72-141 |

TABLE 25-continued

| Factor 10 | 67% | 74-146 |
| Factor 8 | 87% | 50-184 |
| Factor 9 | 132% | 48-149 |
| Factor 11 | 123% | 72-153 |
| Factor 12 | 68% | 44-142 |

| Bleeding time analysis | Result | Normal range reference |
|---|---|---|
| PT | 12.3 sec | 9.8-12.2 |
| aPTT | 34.9 sec | 26-35.3 |
| Fibrinogen | 235 mg/dl | 180-380 |

As listed in Table 25, activities of blood coagulation factors 2, 5, 7, 8, 9, 11, and 12 of the individual sg01 were in the normal range, but an activity of the blood coagulation factor 10 was as low as 67% out of the normal range of from 74 to 146%. That is, the blood coagulation ability of the individual sg01 was lower than normal at least in view of the blood coagulation factor 10. Therefore, the individual sg01 had a risk of an increase in a hemorrhagic tendency. Further, as a result of PT, aPTT, and fibrinogen tests for directly measuring a hemorrhagic tendency, it was confirmed that the individual sg01 had a hemorrhagic tendency which was slightly high but maintained at an approximately upper end of the normal range. That is, it is deemed that the individual sg01 shows a blood coagulation condition maintained in an approximately normal range by the activity of the other non-damaged F10 of the pair of F10 as the heterozygote and the overall adaptive response of the other blood coagulation mechanisms. However, as can be seen from the activity test result of the blood coagulation factors, the individual sg01 maintains a normal state with difficulty and is highly likely to lack a sufficient buffering capacity. Therefore, if the anticoagulant Rivaroxaban is prescribed for the individual sg01 in the future due to medical necessity, the individual sg01 is highly likely to experience severe side effects such as a high hemorrhagic tendency. Since the blood coagulation factor 10 is a sole and direct target protein of Rivaroxaban, it is deemed that such a deduction is very clinically and medically reasonable. It is confirmed from the above-described result that it is possible to suggest a method for preventing drug side effects by analyzing a relation between novel genome sequence variations, which have not been known, and a use of a drug and the clinical and medical usefulness thereof actually exists.

Although the exemplary embodiments of the present invention have been described in detail, the scope of the right of the present invention is not limited thereto. Various modifications and improvements made by those skilled in the art using the basic concept of the present invention defined in the appended claims are also included in the scope of the right of the present invention.

Unless defined otherwise, all technical terms used herein have the same meaning as those commonly understood to one of ordinary skill in the art to which this invention pertains. All the publications cited as references in the present specification are incorporated herein by reference in their entirety.

The invention claimed is:

1. A method for personalizing selection of a drug for a subject using individual genome sequence variations of the subject, comprising:

obtaining, by a computer system, information regarding gene sequences of the subject for a set of genes involved in pharmacodynamics or pharmacokinetics of a drug group, wherein the drug group consists of a plurality of drugs with a same ATC code, wherein the same ATC code is selected from ATC codes for ACE inhibitors, analgesics, anti-diabetes, antidepressants, antihistamines for systemic use, antihypertensives, anxiolytics and hypnotics/sedatives, beta blocking agents, calcium channel blockers, diuretics, drugs for obstructive airway diseases, lipid modifying agents, proton pump inhibitors, sex hormones and modulators of the genital system, and thyroid therapy;

determining, by the computer system, gene sequence variation information indicating variations present in the gene sequences involved in the pharmacodynamics or pharmacokinetics of the group;

for each gene of the set of genes:
  determining, by the computer system, a gene sequence variation score, the gene sequence variation score being a numerical score indicating degree of variations in the gene that cause an amino acid sequence variation in a protein encoded by the gene or cause a transcription control variation, thereby causing change or damage to a structure or function of the protein;
  storing, by the computer system, the determined gene sequence variation scores for the genes;

for each protein encoded by a gene of the set of genes:
  calculating, by the computer system, an individual protein damage score for the protein by using [Equation 2], wherein [Equation 2] is:

$$S_g(v_1, \ldots, v_n) = \left( \prod_{i=1}^{n} v_i^{w_i} \right)^{1/\sum_{i=1}^{n} w_i}$$

wherein Sg is the individual protein damage score of a protein encoded by a gene g, n is the number of target sequence variations for analysis among sequence variations of the gene g, $v_i$ is a gene sequence variation score of an $i^{th}$ gene sequence variation, and $w_i$ is a weighting assigned to the gene sequence variation score $v_i$ of the $i^{th}$ gene sequence variation;
  storing, by the computer system, the individual protein damage scores for the proteins, each individual protein damage score representing a summary of the gene sequence variation scores for the gene encoding the corresponding protein;

for each drug in the drug group:
  calculating, by the computer system, an individual drug score by using [Equation 4], wherein [Equation 4] is:

$$S_d(g_1, \ldots, g_n) = \left( \prod_{i=1}^{n} g_i^{w_i} \right)^{1/\sum_{i=1}^{n} w_i}$$

wherein $S_d$ is the individual drug score of a drug d, n is a number of proteins encoded by one or more genes involved in the pharmacodynamicsor pharmacokinetics of the drug group d, $g_i$ is a protein damage score of a protein encoded by one or more genes involved in the pharmacodynamics or pharmacokinetics of the drug group d, and $w_i$ is a weighting assigned to the protein damage score $g_i$ of the protein encoded by one or more genes involved in the pharmacodynamics or pharmacokinetics of the drug group d;
  storing, by the computer system, the individual drug scores for the drugs in the drug group;
  ranking, by the computer system, drugs in the drug group by comparing the individual drug scores for the drugs;
  selecting a drug for treatment based on the ranking; and treating the subject with the selected drug.

2. The method according to claim 1, wherein the gene sequence variation information means information about substitution, addition, or deletion of a base constituting an exon of a gene.

3. The method according to claim 2,
  wherein the substitution, addition, or deletion of the base results from structural abnormality including breakage, deletion, duplication, inversion, or translocation of a chromosome.

4. The method according to claim 1, wherein the gene sequence variation score is calculated by applying one or more algorithms selected from the group consisting of SIFT (Sorting Intolerant From Tolerant), PolyPhen (Polymorphism Phenotyping), PolyPhen-2, MAPP (Multivariate Analysis of Protein Polymorphism), Logre (Log R Pfam E-value), MutationAssessor, MutationTaster, MutationTaster2, PROVEAN (Protein Variation Effect Analyzer), PMut, Condel, GERP (Genomic Evolutionary Rate Profiling), GERP++, CEO (Combinatorial Entropy Optimization), SNPeffect, fathmm, and CADD (Combined Annotation-Dependent Depletion) to a gene sequence variation.

5. The method according to claim 1,
  wherein the weighting assigned to the gene sequence variation score or the weighting assigned to the protein damage score is determined considering a class of the protein, pharmacodynamic or pharmacokinetic classification of the protein, pharmacokinetic parameters of the enzyme protein of a corresponding drug, a population group, or a race distribution.

6. The method according to claim 1,
  wherein the ranking step further comprises determining an order of priorities among drugs applicable to the subject by using the individual drug score; or wherein the selecting step further comprises determining whether or not to use the drugs applicable to the subject by using the individual drug score.

7. The method according to claim 1,
  wherein the drug group is information input by a user, information input from a prescription, or information input from a database including information about a drug effective in treating a predetermined disease.

8. The method according to claim 1,
  wherein the gene sequence variation information is acquired by a comparison analysis with a genome sequence of a reference group.

9. The method according to claim 1, further comprising: calculating a prescription score.

10. The method according to claim 9,
  wherein if two or more drugs are determined on the basis of an order of priority among drugs and need to be administered at the same time, the prescription score is calculated by summarizing drug scores determined with respect to the respective drugs.

11. The method according to claim 1, further comprising: providing one or more information selected from the group consisting of gene sequence variation information, a protein damage score, a drug score, and information used for calculation thereof.

12. The method according to claim 1,
  wherein the method is performed to prevent drug side effects.

13. A computer-readable storage medium comprising stored instructions, wherein the instructions when executed by a processor cause the processor to perform steps comprising:
- obtaining information regarding gene sequences of a subject for a set of genes involved in pharmacodynamics or pharmacokinetics of a drug group, wherein the drug group consists of a plurality of drugs with a same ATC code, wherein the same ATC code is selected from ATC codes for ACE inhibitors, analgesics, anti-diabetes, antidepressants, antihistamines for systemic use, antihypertensives, anxiolytics and hypnotics/sedatives, beta blocking agents, calcium channel blockers, diuretics, drugs for obstructive airway diseases, lipid modifying agents, proton pump inhibitors, sex hormones and modulators of the genital system, and thyroid therapy;
- determining gene sequence variation information indicating variations present in the gene sequences involved in the pharmacodynamics or pharmacokinetics of the drug group;
- for each gene of the set of genes:
  - determining, by the computer system, a gene sequence variation score, the gene sequence variation score being a numerical score indicating degree of variations in the gene that cause an amino acid sequence variation in a protein encoded by the gene or cause a transcription control variation, thereby causing change or damage to a structure or function of the protein;
- storing the determined gene sequence variations scores for the genes;
- for each protein encoded by a gene of the set of genes
  - calculating an individual protein damage score for the protein by using [Equation 2], wherein [Equation 2] is:

$$S_g(v_1, \ldots, v_n) = \left(\prod_{i=1}^{n} v_i^{w_i}\right)^{1/\sum_{i=1}^{n} w_i}$$

wherein Sg is the individual protein damage score of a protein encoded by a gene g, n is the number of target sequence variations for analysis among sequence variations of the gene g, $v_i$ is a gene sequence variation score of an $i^{th}$ gene sequence variation, and $w_i$ is a weighting assigned to the gene sequence variation score $v_i$ of the $i^{th}$ gene sequence variation;

- storing the individual protein damage scores for the proteins, each individual protein damage score representing a summary of the gene sequence variation scores for the gene encoding the corresponding protein;
- for each drug in the drug group:
  - calculating an individual drug score by using [Equation 4], wherein [Equation 4] is:

$$S_d(g_1, \ldots, g_n) = \left(\prod_{i=1}^{n} v_i^{w_i}\right)^{1/\sum_{i=1}^{n} w_i}$$

wherein $S_d$ is the individual drug score of a drug d, n is a number of proteins encoded by one or more genes involved in the pharmacodynamics or pharmacokinetics of the drug group d, $g_i$ is a protein damage score of a protein encoded by one or more genes involved in the pharmacodynamics or pharmacokinetics of the drug group d, and $w_i$ is a weighting assigned to the protein damage score $g_i$ of the protein encoded by one or more genes involved in the pharmacodynamics or pharmacokinetics of the drug group d;

- storing the individual drug scores for the drugs in the drug group;
- ranking drugs in the drug group by comparing the individual drug scores for the drugs;
- selecting a drug for treatment based on the ranking; and
- treating the subject with the selected drug.

* * * * *

UNITED STATES PATENT AND TRADEMARK OFFICE
CERTIFICATE OF CORRECTION

PATENT NO. : 10,950,326 B2
APPLICATION NO. : 14/912397
DATED : March 16, 2021
INVENTOR(S) : Ju Han Kim et al.

Page 1 of 1

It is certified that error appears in the above-identified patent and that said Letters Patent is hereby corrected as shown below:

In the Claims

Column 87, Line 59, Claim 1: delete "involved in the pharmacodynamicsor pharmacokinetics" and insert -- involved in the pharmacodynamics or pharmacokinetics --.

Column 90, Lines 18-19, Claim 13: Equation 4, in the large parenthesis, delete "Vi" and insert -- gi --.

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*